US010604548B2

(12) United States Patent
Puckette et al.

(10) Patent No.: US 10,604,548 B2
(45) **Date of Patent: *Mar. 31, 2020**

(54) MINICIRCLE DNA VECTOR VACCINE PLATFORM FOR FOOT-AND-MOUTH DISEASE AND METHODS THEREOF

(71) Applicant: The Government of the United States of America, as Represented by the Secretary, Department of Homeland Security, Washington, DC (US)

(72) Inventors: Michael Puckette, Waterford, CT (US); Max Rasmussen, Guilford, CT (US); John Neilan, Wethersfield, CT (US)

(73) Assignee: The Government of the United States of America, as represented by the Secretary of Homeland Security, Washington, DC (US)

( * ) Notice: Subject to any disclaimer, the term of this patent is extended or adjusted under 35 U.S.C. 154(b) by 61 days.

This patent is subject to a terminal disclaimer.

(21) Appl. No.: 15/958,218

(22) Filed: Apr. 20, 2018

(65) Prior Publication Data

US 2018/0237478 A1 Aug. 23, 2018

Related U.S. Application Data

(62) Division of application No. 14/962,272, filed on Dec. 8, 2015, now Pat. No. 9,975,926.

(51) Int. Cl.
*C07K 14/005* (2006.01)
*G01N 33/569* (2006.01)
*A61K 39/00* (2006.01)

(52) U.S. Cl.
CPC ..... *C07K 14/005* (2013.01); *G01N 33/56983* (2013.01); *A61K 39/00* (2013.01); *C12N 2770/32122* (2013.01); *C12N 2770/32123* (2013.01); *C12N 2770/32134* (2013.01); *G01N 2333/09* (2013.01); *G01N 2469/20* (2013.01); *G01N 2800/26* (2013.01)

(58) Field of Classification Search
None
See application file for complete search history.

(56) References Cited

U.S. PATENT DOCUMENTS

| | | | |
|---|---|---|---|
| 5,354,670 A | 10/1994 | Nickoloff et al. | |
| 8,236,548 B2 | 8/2012 | Chen et al. | |
| 9,975,926 B2 | 5/2018 | Puckette et al. | |
| 2012/0258133 A1 | 10/2012 | Charleston et al. | |
| 2012/0315295 A1 | 12/2012 | Rieder et al. | |
| 2017/0158739 A1 | 6/2017 | Puckette et al. | |
| 2018/0244728 A1* | 8/2018 | Puckette | C07K 14/005 |

FOREIGN PATENT DOCUMENTS

WO 2011/048353 A2 4/2011

OTHER PUBLICATIONS

Terhuja et al. (Biologicals. Oct. 2015; 43: 437-443).*
Yang et al., "A novel minicircle vector based system for inhibiting the replication and gene expression of Enterovirus 71 and Coxsackievirus A16", Antiviral Research 96 (2012), p. 234-244.
Wang et al., "In Vivo Electroporation of Minicircle DNA as a novel method of vaccine delivery to enhance HIV-1-Specific Immune Responses", Journal of Virology, vol. 88, No. 4 (2014), p. 1924-1934.
de Crecy-Lagard, Valerie, "Identification of Genes Encoding tRNA Modification Enzymes by Comparative Genomics", Methods Enzymol, 2007, vol. 425, p. 153-183.
Green et al., "Characterization of the Mechanical unfolding of RNA Pseudoknots", J. Mol. Biol. (2008), vol. 375, p. 511-528.
Kay et al., "A robust system for production of minicircle DNA vectors", Nature Biotechnology, 2010, p. 1-5.
Kim et al., "Superluminescent variants of Marine Luciferases for Bioassays", Analytical Chemistry, 2011, vol. 83, p. 8732-8740.
Mayr et al., "Immune responses and protection against foot-and-mouth disease virus (FMDV) challenge in swine vaccinated with adenovirus-FMDV constructs", Vaccine, 19, 2001, p. 2152-2162.
Moraes et al., "Early protection against homologous challenge after a single dose of replication-defective human adenovirus type 5 expressing capsid proteins of foot-and-mouth disease virus (FMDV) strain A24", Vaccine, 20, 2002, p. 1631-1639.
Pacheco et al., "Rapid protecting of cattle from direct challenge with foot-and-mouth disease virus (FMDV) by a single inoculation with an adenovirus-vectored FMDV subunit vaccine", Virology, 337, 2005, p. 205-209.
Porta et al., "Efficient production of foot-and-mouth disease virus empty capsids in insect cells following down regulation of 3C protease activity", Journal of Virological Methods, 187, 2013, p. 406-412.

(Continued)

*Primary Examiner* — Shanon A. Foley
(74) *Attorney, Agent, or Firm* — Lavanya Ratnam; Kelly G. Hyndman

(57) ABSTRACT

This application is directed generally to minicircle DNA vectors for the vaccination of foot-and-mouth disease (FMD). The transgene expression cassette in the minicircle DNA vector includes: a eukaryotic translation initiation nucleotide sequence, a mutant nucleotide sequence that encodes a foot-and-mouth disease virus (FMDV) capsid polyprotein precursor that contains at least one mutation to eliminate a restriction enzyme recognition site, a nucleotide sequence that encodes a protease that cleaves the MEW capsid polyprotein precursor into plurality of FMDV capsid proteins and a translational regulatory element to regulate the expression of the protease. The minicircle DNA vectors can be transfected directly into the cell of a mammalian host. When transfected into the mammalian host cell, virus-like particles can be produced intrinsically to stimulate the mammalian host's immune system to develop adaptive immunity toward foot-and-mouth disease.

17 Claims, 8 Drawing Sheets

Specification includes a Sequence Listing.

(56) References Cited

OTHER PUBLICATIONS

Rajaskekhar et al., "Rescue of infective virus from a genome-length cDNA clone of the FMDV serotype O (IND-R2/75) vaccine strain and its characterization", Research in Veterinary Science, 95, 2013, p. 291-297.

Montes et al., "Optimizing restriction site placement for synthetic genomes", Information and Computation, 213, 2012, p. 59-69.

Sequence Alignment of SEQ ID No. 4 with GENSEQ Database Access No. AAA13691 by Iadarola et al. WO 20001680 Jul. 2000.

Sequence Alignment of SEQ ID No. 5 with GENSEQ Database Access No. AAC8400 by Prusiner et al. WO 200068382 Nov. 2000.

* cited by examiner

A = mc SGLuc
B = mc O1P1-3C(wt)
C = mc O1P1-HIV-3C(C142T)

mc SGLuc mc O1P1-3C mc O1P1-HIV-3C(C142T)

MINICIRCLE DNA VECTOR VACCINE PLATFORM FOR FOOT-AND-MOUTH DISEASE AND METHODS THEREOF

CROSS-REFERENCE TO RELATED APPLICATIONS

This application is a divisional of U.S. Ser. No. 14/962,272 filed Dec. 8, 2015, which is herein incorporated by reference in its entirety.

GOVERNMENT RIGHTS

This invention was made with government support under HSHQPM-12-X-00013 and HSHQDC-14-F-00035 awarded by the U.S. Department of Homeland Security. The Government has certain rights in this invention.

SEQUENCE LISTING

The instant application contains a Sequence Listing which has been submitted electronically in ASCII format and is hereby incorporated by reference in its entirety. The ASCII copy, created on Apr. 20, 2018, and is 94 KB in size.

BACKGROUND

Technical Field

The present disclosure relates to compositions and methods for the vaccination and diagnosis of foot-and-mouth disease. More specifically, the present disclosure relates to a minicircle vector that is expressed in a mammalian host cell to produce virus-like particles of foot-and-mouth disease virus (FMDV).

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present disclosure.

The foot-and-mouth disease virus (FMDV), a prototypic aphthovirus within the Picornaviridae family, is the causative agent of a highly infectious and sometimes fatal disease that affects cloven-hoofed animals such as cattle, pigs, sheep, goats, deer and other animals with cloven hooves. There are seven major FMDV antigenically distinct virus serotypes (A, O, C, Asia 1 and South African Territories or SAT 1, 2 and 3) and multiple subtypes or topotypes exist within each serotype. Infection with any one serotype does not confer protective immunity against another. Serotype O is the most common serotype worldwide.

After an animal is infected with the FMDV, the first signs of illness usually appear within 2 to 14 days: high fever for 2-3 days followed by blisters inside the mouth and on the feet that may rupture and cause lameness.

FMD outbreaks cause significant agro-economic losses and severe implications for animal farming throughout much of the world. For example, the outbreak of FMD in the U.K. in 2001 was estimated to cost the U.K. £ 8 billion, including 6 million slaughtered livestock. Since the virus causing the disease is highly contagious and can be spread by infected livestock through aerosols, through contact with contaminated farming equipment, vehicles, clothing, or feed, and by domestic and wild predators, the containment of FMD demands considerable efforts in vaccination, strict monitoring, trade restrictions, and quarantines, and sometimes, the culling of animals.

BRIEF SUMMARY

According to a first aspect, the present disclosure provides a mutant nucleotide sequence that encodes a foot-and-mouth disease virus (FMDV) capsid polyprotein precursor, the mutant nucleotide sequence comprising a mutation that removed a restriction enzyme recognition site from a nucleotide sequence from which the mutant nucleotide sequence was formed.

In one or more embodiments, the nucleotide sequence comprises at least one of one through twenty-two (1-22) silent mutations, one through fifteen (1-15) silent mutations, or one through ten (1-10) silent mutations that removed one or more restriction enzyme recognition sites.

In one or more embodiments, the one through twenty-two (1-22) silent mutations, one through fifteen (1-15) silent mutations, or one through ten (1-10) silent mutations are selected from the group consisting of C99, C285, T345, G354, A369, C408, C468, G498, C528, A588, C597, C627, C957, G1170, T1338, T1518, C1578, T1593, C1665, C1836, C2010, A2190 and combinations thereof.

In one or more embodiments, the one through twenty-two (1-22) silent mutations, one through fifteen (1-15) silent mutations, or one through ten (1-10) silent mutations are selected from the group consisting of C99T, C 285T, Y345A, G354A, A369G, C408T, C468A, G498A, C528T, A588T, C597T, C627T, C957A, G1170C, T1338C, T1518C, C1578A, T1593A, C1665G, C1836G, C2010T, A2190T, and combinations thereof.

In one or more embodiments, the mutant nucleotide sequence comprises the nucleotide sequence of SEQ ID NO: 1.

In one or more embodiments, the restriction enzyme recognition site is selected from the group consisting of XbaI, XcmI, BsiWI, XhoI, BstEII, PflMI, AccI, NheI, SacII, PpuMI, AgeI, PvuII, NcoI, PstI, BstXI, AatI and combinations thereof.

In one or more embodiments, the FMDV is selected from the group consisting of O, A, C, Asia 1, SAT 1, SAT 2 and SAT 3 serotypes.

According to a second aspect, the present disclosure provides a vector comprising a mutant nucleotide sequence that encodes a foot-and-mouth disease virus (FMDV) capsid polyprotein precursor that includes a mutation that removed a restriction enzyme recognition site from a nucleotide sequence from which the mutant nucleotide sequence was formed.

In one or more embodiments, the vector further comprises a eukaryotic translation initiation nucleotide sequence positioned 5' to the mutant nucleotide sequence, a nucleotide sequence that encodes a protease, and a translational regulatory element positioned 3' to the mutant sequence and 5' to the nucleotide sequence that encodes the protease.

In one or more embodiments, the protease is functionally able to cleave the FMDV capsid polyprotein precursor into plurality of FMDV capsid proteins.

In one or more embodiments, the FMDV capsid proteins are selected from a group consisting of VP0, VP1, VP2, VP3, VP4, and combinations thereof.

In one or more embodiments, the transitional regulatory element is functional to reduce expression of the protease relative to the nucleotide sequence that encodes the protease.

In one or more embodiments, the vector expresses the protease.

In one or more embodiments, the vector comprises a minicircle vector,

In one or more embodiments, the vector comprises the nucleotide sequence of SEQ ID NO: 2.

In one or more embodiments, the mutant nucleotide sequence further comprises at least one of one through twenty-two (1-22) silent mutations, one through fifteen (1-15) silent mutations, or one through ten (1-10) silent mutations that removed one or more restriction enzyme recognition sites.

In one or more embodiments, the one through twenty-two (1-22) silent mutations, one through fifteen (1-15) silent mutations, or one through ten (1-10) silent mutations are selected from the group consisting of C99, C285, T345, G354, A369, C408, C468, G498, C528, A588, C597, C627, C957, G1170, T1338, T1518, C1578, T1593, C1665, C1836, C2010, A2190 or combinations thereof.

In one or more embodiments, the one through twenty-two (1-22) silent mutations, one through fifteen (1-15) silent mutations, or one through ten (1-10) silent mutations are selected from the group consisting of C99T, C285T, T345A, G354A, A369G, C408T, C468A, G498A, C528T, A588T, C597T, C627T, C957A, G1170C, T1338C, T1518C, C1578A, T1593A, C1665G, C1836G, C2010T, A2190T, and combinations thereof.

In one or more embodiments, the mutant nucleotide sequence comprises the nucleotide sequence of SEQ ID NO: 1.

In one or more embodiments, the vector comprises the nucleotide sequence of SEQ ID NO: 3.

In one or more embodiments, the eukaryotic translation initiation nucleotide sequence comprises SEQ ID NO: 4.

In one or more embodiments, the eukaryotic translation initiation nucleotide sequence comprises SEQ ID NO: 5.

In one or more embodiments, the translational regulatory element comprises a DNA or RNA sequence responsible for a ribosomal frameshift.

In one or more embodiments, the DNA or RNA sequence responsible for a ribosomal frameshift is selected from the group consisting of an AIR, pseudoknot, an antizyme RNA frameshifting stimulation element, a coronavirus frameshifting stimulation element, a DnaX ribosomal frameshifting element, a HIV ribosomal frameshift signal, an insertion sequence IS1222 ribosomal frameshifting element, and a ribosomal frameshift.

In one or more embodiments, the DNA or RNA sequence responsible for a ribosomal frameshift is functional to mediate a translational frameshift in the protease in an amount of 90-95% of translated protease mRNA.

In one or more embodiments, the DNA or RNA sequence responsible for a ribosomal frameshift is functional to yield translation of no more than twenty percent (20%) of the nucleotide sequence that encodes the protease after translation.

In one or more embodiments, the DNA or RNA sequence responsible for a ribosomal frameshift is functional to yield translation of between five and ten percent (5-10%) of the nucleotide sequence that encodes the protease after translation.

In one or more embodiments, the nucleotide sequence that encodes the protease is fully translated and comprises a correct translation of the protease after translation.

In one or more embodiments, the DNA or RNA sequence responsible for a ribosomal frameshift comprises the nucleotide sequence of SEQ ID NO: 6.

In one or more embodiments, the nucleotide sequence that encodes a protease comprises the nucleotide sequence of SEQ ID NO: 7, and the amino acid sequence of the protease comprises SEQ ID NO: 8.

In one or more embodiments, the nucleotide sequence that encodes a protease comprises SEQ ID NO: 9.

In a third aspect, the present disclosure provides a transformed host cell comprising a mutant nucleotide sequence that encodes a foot-and-mouth disease virus (FMDV) capsid polyprotein precursor that includes a mutation that removed a restriction enzyme recognition site from a nucleotide sequence from which the mutant nucleotide sequence was formed.

In one or more embodiments, the mutant nucleotide sequence further comprises at least one of one through twenty-two (1-22) silent mutations, one through fifteen (1-15) silent mutations, or one through ten (1-10) silent mutations that removed one or more restriction enzyme recognition sites.

In one or more embodiments, the one through twenty-two (1-22) silent mutations, one through fifteen (1-15) silent mutations, or one through ten (1-10) silent mutations are selected from the group consisting of C99, C285, T345, G354, A369, C408, C468, G498, C528, A588, C597, C627, C957, G1170, T1338, T1518, C1578, T1593, C1665, C1836, C2010, A2190 or combinations thereof.

In one or more embodiments, the one through twenty-two (1-22) silent mutations, one through fifteen (1-15) silent mutations, or one through ten (1-10) silent mutations are selected from the group consisting of C99T, C285T, T345A, G354A, A369G, C408T, C468A, G498A, C528T, A588T, C597T, C627T, C957A, G1170C, T1338C, T1518C, C1578A, T1593A, C1665G, C1836G, C2010T, A2190T, and combinations thereof.

In one or more embodiments, the transformed host cell comprises a mammalian cell.

In one or more embodiments, the transformed host cell is functional to produce a virus like particle (VLP).

In one or more embodiments, the VLP comprises a FMDV VLP.

In a fourth aspect, the present disclosure provides virus like particle (VLP) comprising a polypeptide produced from expression of a vector comprising a mutant nucleotide sequence that encodes a foot-and-mouth disease virus (FMDV) capsid polyprotein precursor and includes a mutation that removed a restriction enzyme recognition site from a nucleotide sequence from which the mutant nucleotide sequence was formed.

In one or more embodiments, the mutant nucleotide sequence further comprises at least one of one through twenty-two (1-22) silent mutations, one through fifteen (1-15) silent mutations, or one through ten (1-10) silent mutations that removed one or more restriction enzyme recognition sites.

In one or more embodiments, the one through twenty-two (1-22) silent mutations, one through fifteen (1-15) silent mutations, or one through ten (1-10) silent mutations are selected from the group consisting of C99, C285, T345, G354, A369, C408, C468, G498, C528, A588, C597, C627, C957, G1170, T1338, T1518, C1578, T1593A, C1665, C1836, C2010, A2190 or combinations thereof.

In one or more embodiments, the one through twenty-two (1-22) silent mutations, one through fifteen (1-15) silent mutations, or one through ten (1-10) silent mutations are selected from the group consisting of C99T, C285T, T345A, G354A, A369G, C408T, C468A, G498A, C528T, A588T, C597T, C627T, C957A, G1170C, T1338C, T1518C, C1578A, T1593A, C1665G, C1836G, C2010T, A2190T, and combinations thereof.

In one or more embodiments, the vector further comprises a eukaryotic translation initiation nucleotide sequence positioned 5' to the mutant nucleotide sequence, a nucleotide sequence that encodes a protease, and a translational regulatory element positioned 3' to the mutant sequence and 5' to the nucleotide sequence that encodes the protease.

In a fifth aspect, the present disclosure provides a method of vaccinating a mammal against a foot-and-mouth disease virus (FMDV), comprising administering a vector comprising a mutant nucleotide sequence which when expressed in a host cell of the mammal induces production of foot-and-mouth disease virus virus-like particles (VLP) by the host cell, the mutant nucleotide sequence encodes a FMDV capsid polyprotein precursor and includes a mutation to remove a restriction enzyme recognition site from a nucleotide sequence from which the mutant nucleotide sequence was formed.

In one or more embodiments, the mutant nucleotide sequence further comprises at least one of one through twenty-two (1-22) silent mutations, one through fifteen (1-15) silent mutations, or one through ten (1-10) silent mutations that removed one or more restriction enzyme recognition sites.

In one or more embodiments, the one through twenty-two (1-22) silent mutations, one through fifteen (1-15) silent mutations, or one through ten (1-10) silent mutations are selected from the group consisting of C99, C285, T345, G354, A369, C408, C468, G498, C528, A588, C597, C627, C957, G1170, T1338, T1518, C1578, T1593, C1665, C1836, C2010, A2190 or combinations thereof.

In one or more embodiments, the one through twenty-two (1-22) silent mutations, one through fifteen (1-15) silent mutations, or one through ten (1-10) silent mutations are selected from the group consisting of C99T, C285T, T345A, G354A, A369G, C408T, C468A, G498A, C528T, A588T, C597T, C627T, C957A, G1170C, T1338C, T1518C, C1578A, T1593A, C1665G, C1836G, C2010T, A2190T, and combinations thereof.

In one or more embodiments, the method further comprises administering an adjuvant with the vector.

In a sixth aspect, the present disclosure provides a method of determining whether a mammal is vaccinated against or infected with foot-and-mouth disease virus (FMDV) comprising detecting an antibody's presence in a sample from the mammal, and detecting an other antibody's presence or absence in the sample, the absence of the other antibody indicates vaccination of the mammal with a vector comprising a mutant nucleotide sequence which when expressed in a host cell of the mammal induces production of FMDV virus-like particles, the mutant nucleotide sequence encodes a FMDV capsid polyprotein precursor and a mutation to remove a restriction enzyme recognition site from a nucleotide sequence from which the mutant nucleotide sequence was formed.

In one or more embodiments, the mutant nucleotide sequence further comprises at least one of one through twenty-two (1-22) silent mutations, one through fifteen (1-15) silent mutations, or one through ten (1-10) silent mutations that removed one or more restriction enzyme recognition sites.

In one or more embodiments, the one through twenty-two (1-22) silent mutations, one through fifteen (1-15) silent mutations, or one through ten (1-10) silent mutations are selected from the group consisting of C99, C285, T345, G354, A369, C408, C468, G498, C528, A588, C597, C627, C957, G1170, T1338, T1518, C1578, T1593, C1665, C1836, C2010, A2190 or combinations thereof.

In one or more embodiments, the one through twenty-two (1-22) silent mutations, one through fifteen (1-15) silent mutations, or one through ten (1-10) silent mutations are selected from the group consisting of C99T, C285T, T345A, G354A, A369G, C408T, C468A, G498A, C528T, A588T, C597T, C627T, C957A, G1170C, T1338C, T1518C, C1578A, T1593A, C1665G, C1836G, C2010T, A2190T, and combinations thereof.

In one or more embodiments, the mammal produced the antibody responsive to vaccination with the vector.

In one or more embodiments, the other antibody comprises a plurality of antibodies that do not include the antibody.

In one or more embodiments, the plurality of antibodies comprise antibodies against FMDV non-structural proteins.

In one or more embodiments, the plurality of antibodies are associated with FMDV infection.

In one or more embodiments, the detecting the antibody's presence implements an immunoassay.

In one or more embodiments, immunoassay comprises an enzyme linked immunosorbent assay (ELISA).

In one or more embodiments, the detecting the other antibody's presence or absence implements an immunoassay.

In one or more embodiments, the immunoassay comprises an enzyme linked immunosorbent assay (ELISA).

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

An appreciation of the disclosure and many of the attendant advantages thereof may be understood by reference to the accompanying drawings. Included in the drawings are the following figures.

DETAILED DESCRIPTION OF THE EMBODIMENTS

Overview

Figure 1:
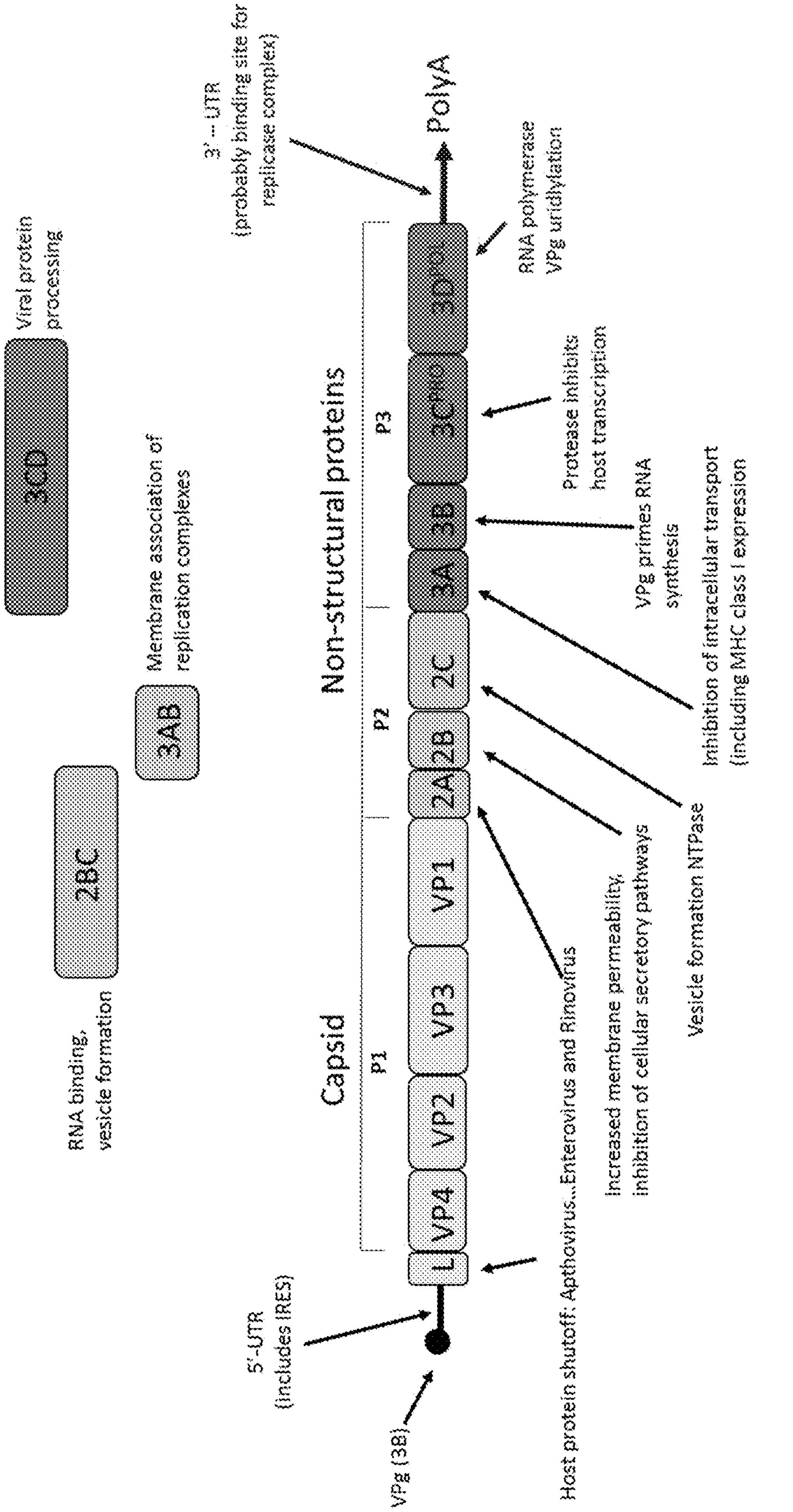
FIG. 1 is a diagrammatic representation of the picornavirus genome that includes translated capsid and other non-structural proteins.

Some vaccine includes the use of a whole virus that is either killed or inactivated, such as by chemically inactivating the virus, or is attenuated by various means. Vaccines are fraught with limitations and shortcomings, such as potential virus escape, vaccine instability (e.g., loss of immunogenicity during transportation and storage), short duration of immunity and the use of multiple antigens (e.g., dozens) to address viral mutation, evolution and antigenic diversity. Furthermore, the set-up and running costs of the vaccine production facilities are very high, and the antibody profiles animals vaccinated with the whole virus may not be easily distinguished from those of infected animals.

Description

Referring now to the drawings, wherein like reference numerals designate identical or corresponding parts throughout the several views.

For purposes of the present invention, "foot-and-mouth-disease virus" or the acronym FMDV refers to any of the seven major FMDV antigenically distinct virus serotypes, i.e. A, O, C, Asia 1 and South African Territories 1, 2 and 3 as well as the multiple subtypes or topotypes exist within each serotype. Infection with any one serotype does not confer protective immunity against another. The FMDV is a non-enveloped picornavirus (belonging to the genus *Aphthovirus* of the family Picornaviridae) with a single-stranded genomic RNA of between 7,500 to 8,000 nucleotides or approximately between 7,500 to 8,000 nucleotides, approximately 7,500 nucleotides, or approximately 8,000 nucleotides. The capsid, which is the protein shell of the virus, is made up of 60 copies of each of the four structural proteins VP1, VP2, VP3 and VP4 (see FIG. 1). In embodiments, during assembly, P1, a 95-kDa capsid polyprotein precursor is cleaved by the viral 3C protease to ultimately yield VP1, VP2, VP3 and VP4. As shown in FIG. 1, apart from the 3C protease, the FMDV also expresses several other non-structural or non-capsid proteins (e.g. 2A-C, 3A-D) that can be involved in virus replication and various cellular functions.

The present disclosure provides compositions comprising recombinant foot-and-mouth disease virus (FMDV) nucleic acids and/or proteins for use in vaccine formulations and diagnostic reagents, as well as methods of preparing the compositions.

In particular, these compositions include mutant FMDV nucleotide sequences and transgene expression cassettes. In some embodiments, the compositions further comprise vehicles to carry and transfer the transgene expression cassette such as vectors (preferably minicircle vectors) and host cells (preferably mammalian cells) wherein the transgene expression cassette may be expressed and/or replicated.

For purposes of the present disclosure, a "nucleotide sequence" or "nucleic acid sequence" is a succession of letters that indicate the order of nucleotides or nucleic acids within a DNA (using GACT) or RNA molecule (using GACU). The DNA or RNA molecule may be single or double stranded and may be genomic, recombinant, mRNA or cDNA.

For purposes of the present disclosure, a "transgene expression cassette" or "transgene expression construct" is a nucleic acid sequence that has been artificially constructed to comprise one or more functional units (e.g. promoter, control element, consensus sequence, translational frameshift sequence, protein encoding gene etc.) not found together in nature, and is capable of directing the expression of any RNA transcript in an organism that the cassette has been transferred to, including gene encoding sequence(s) of interest as well as non-translated RNAs, such as shRNAs, microRNAs, siRNAs, anti-sense RNAs. A transgene expression cassette may be single- or double-stranded and circular or linear. A transgene expression cassette can be constructed, inserted or cloned into a "vector", which serves as a vehicle for transferring, replicating and/or expressing nucleic acid sequences in target cells.

The transgene expression cassette according to the disclosure can be constructed as a single open reading frame. The transgene expression cassette includes a consensus nucleotide sequence for eukaryotic translation initiation (e.g., Kozak consensus sequence), a nucleotide sequence that encodes a FMDV capsid polyprotein precursor that contains at least one mutation to eliminate a restriction enzyme recognition site, a nucleotide sequence that encodes a protease that cleaves the capsid polyprotein precursor and a translational regulatory element to regulate the expression of the protease.

The transgene expression cassette described in accordance with embodiments described herein does not encode the complete FMDV genome and therefore cannot cause an accidental FMD outbreak during manufacture, or administration of the vaccine containing the transgene expression cassette.

Furthermore, the transgene expression cassette encodes only the P1 and 3C FMDV viral proteins. Animals treated with a vaccine containing the transgene expression cassette will not produce antibodies to other FMDV viral proteins that are expressed during a natural FMDV infection. For example, if the transgene expression cassette contains a nucleotide sequence that encodes the 2B protein, the animal treated with the vaccine containing the transgene expression cassette containing a nucleotide sequence that encodes the 2B protein will only produce antibodies for the 2B protein and not antibodies for other viral proteins such as 2C, 3B, 3D, etc. The difference in antibody profiles produced after natural infection compared to vaccination with the transgene expression cassette confers the ability to differentiate infected animals from vaccinated animals and vice versa.

Figure 2:
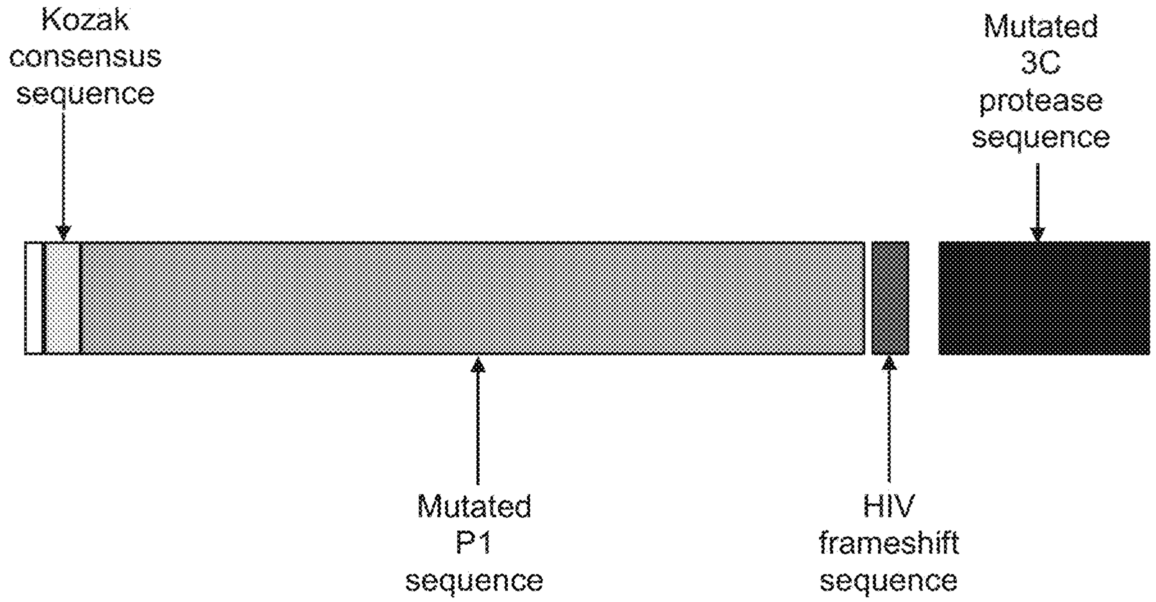
FIG. 2 illustrates the organization and design of the multiple functional units of a transgene expression cassette according to one embodiment.

FIG. 2 shows an embodiment of the transgene expression cassette that is arranged as follows: Kozak consensus sequence-Mutated P1 nucleotide sequence from FMDV-HIV frameshift sequence-Mutated 3C protease nucleotide sequence from FMDV.

In one or more embodiments, the nucleotide sequence of the transgene expression cassette comprises SEQ ID NO: 2.

The Kozak consensus sequence is a sequence which occurs in eukaryotic mRNA and, in one or more embodiments, comprises SEQ ID NO: 4. The Kozak consensus sequence plays a major role in the initiation of the translation process. In some instances the Kozak consensus sequence plays an essential role in initiation of the translation process, e.g., it is substantially the sole determining factor in initiation of the translation process.

In one or more embodiments, the Kozak consensus sequence is a Kozak eukaryotic translation initiation sequence comprising SEQ ID NO: 5.

In principle, effective FMDV vaccines can be produced from recombinant VLPs. However, the formation of stable VLPs in host cells at concentrations high enough to stimulate immune responses are hindered by the viral 3C protease. The 3C protease is used for proper processing and cleaving of the P1 polyprotein precursor, and has been found to be toxic to the host cells. Furthermore, the empty recombinant particles such as empty capsids tend to be less stable than in comparison to virus particles containing nucleic acid.

In some embodiments, the expression of the 3C protease from the transgene expression cassette is down regulated in such a way so the levels of enzyme are reduced or the expressed enzyme is not cytotoxic yet maintains the P1 cleavage activity for capsid formation. This may be achieved by engineering of the enzyme by rational design (e.g., site-directed mutagenesis) and/or random mutagenesis directed evolution followed by screening of the desired enzyme properties) wherein one or more mutations may be introduced to the recombinant gene that encodes the protease. In certain embodiments, the 3C protease contains a mutation at cysteine residue 142. The cysteine may be substituted by another residue, for example, a threonine or an alanine.

In one or more embodiments, the nucleotide sequence of the mutated 3C protease comprises SEQ ID NO: 9 and the amino acid sequence of the mutated 3C protease comprises SEQ ID NO: 10.

In one or more embodiments, the 3C protease in the transgene expression cassette is derived from FMDV Asia Lebanon 1989 strain (serotype Asia-1).

In one or more embodiments, the 3C protease in the transgene expression cassette is derived from FMDV A22 Iraq strain (serotype A).

Alternatively, the expression of 3C protease may be controlled or suppressed with a translational element or a DNA or RNA sequence responsible for a ribosomal frameshift such as ALIL pseudoknot, antizyme RNA frameshifting stimulation element, coronavirus frameshifting stimulation element, DnaX ribosomal frameshifting element, HIV ribosomal frameshift signal, insertion sequence IS1222 ribosomal frameshifting element and a ribosomal frameshift. The DNA or RNA sequence responsible for a ribosomal frameshift may be located upstream of the nucleotide sequence that encodes the protease and downstream of the nucleotide sequence that encodes the capsid polyprotein precursor in the transgene expression cassette, and may cause a frameshift event of occurring in 80-98% of the total translation events. In certain embodiments, the DNA or RNA sequence responsible for a ribosomal frameshift mediates a translational frameshift in the protease in an amount of 90-95% of translated protease mRNA. This results in a small fraction of no more than 20%, preferably 5-10% of the nucleotide sequence that encodes the protease (e.g. 3C protease) downstream of the frameshift element being fully translated with the correct open reading frame.

Frameshifts resulting from ribosomal frameshifting are controlled by various mechanisms found in codons. These mechanisms emerge from the fact that ribosomes do not translate proteins at a steady rate, regardless of the sequence. Certain codons take longer to translate, because there are not equal amounts of tRNA of that particular codon in the cytosol. Due to this lag, there exist in small sections of codons sequences that control the rate of ribosomal frameshifting. Sections of less accessible codons that slow ribosomal transaction are known as "choke points," and sections of easily accessible codons which result in faster ribosomal transaction are "slippery sequences." Slippery sequences can potentially make the reading ribosome "slip" and skip a number of nucleotides (usually only 1) and read a completely different frame thereafter. Choke points reduce the probability of this happening (de Crecy-Lagard, V. *Identification of genes encoding tRNA modification enzymes by comparative genomics*. Methods in Enzymology. 2007 425: 153-83; Green, L., Kim, C. H., Bustamante, C., Tinoco Jr, I. *Characterization of the mechanical unfolding of RNA pseudoknots*. J Mol. Biol. 2008 375 (2):511-28; U.S. Patent Publication No. 20120258133—each incorporated herein by reference in its entirety).

In addition to 3C, Leader (L) and 2A proteins of picornaviruses including the FMDV (see FIG. 1) are responsible for proper viral polyprotein processing. Therefore, wild-type and mutant nucleotide sequences that encode the L and 2A proteins may be used to construct the transgene expression cassette described herein for processing of the P1 capsid polyprotein precursor.

To enhance the stability of the final assembled capsid product, mutagenesis strategies and techniques as previously described may be applied to introduce one or more mutations to the nucleotide sequence that encodes the polyprotein precursor. In one or more embodiments, the nucleotide sequence is 2256 nucleotides in length and encodes the P1 polyprotein precursor derived from the FMDV O1 Manisa isolate 87 strain (serotype O). Among the mutations that can be introduced include silent mutations that effectively eliminate restriction enzyme recognition sites to better facilitate cloning and sub-cloning yet maintain the same translated protein product by not causing any amino acid substitution. These mutations enhance the cloning in and cloning out of the P1 polyprotein precursor into a transgene expression cassette to swap different P1 polyprotein precursors from different FMDV serotypes to promptly respond to the needs of individual outbreaks.

In one or more embodiment, the mutations to the DNA coding sequence of the P1 polyprotein precursor include changes to one or more of C99, C285, T345, G354, A369, C408, C468, G498, C528, A588, C597, C627, C957, G1170, T1338, T1518, C1578, T1593, C1665, C1836, C2010, A2190 or combinations thereof, from one pyrimidine base to another pyrimidine base, from one purine base to another purine base, or to any other base as long as the mutation does not result in an amino acid change upon translation. In one or more embodiments, the nucleotide substitutions are: C99T, C285T, T345A, G354A, A369G, C408T, C468A, G498A, C528T, A588T, C597T, C627T, C957A, G1170C, T1338C, T1518C, C1578A, T1593A, C1665G, C1836G, C2010T, A2190T or combinations thereof, from one pyrimidine base to another pyrimidine base, from one purine base to another purine base, or to any other base as long as the mutation does not result in an amino acid change upon translation.

Figure 3:
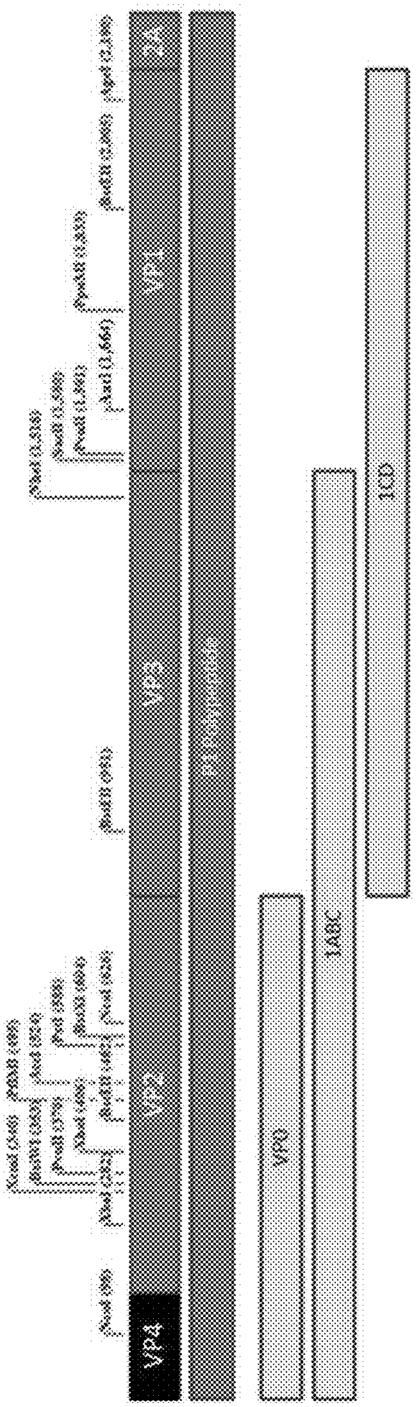
FIG. 3 is a schematic diagram illustrating the locations of multiple restriction enzyme recognition sites in the P1 polyprotein precursor according to one embodiment.

In one or more embodiments, the restriction enzyme recognition sites that are eliminated by the mutations to the P1 polyprotein precursor include, as shown in FIG. 3, XbaI, XcmI, BsiWI, XhoI, BstEII, PflMI, AccI, NheI, SacII, PpuMI, AgeI, PvuII, NcoI, PstI, BstXI and AatI To ensure cessation of mRNA translation, a stop codon sequence (i.e., TAA, TGA, or TAG) may be added to the end of the transgene expression cassette.

In one or more embodiments, the mutated P1 polyprotein precursor comprises nucleotide sequence SEQ ID NO: 1. The nucleotide sequence of a wild-type P1 polyprotein precursor derived from FMDV O1 Manisa isolate 87 comprises SEQ ID NO: 11.

In one or more embodiments, the mutated P1 polyprecursor comprises a mutant nucleotide sequence of a P1 polyprecursor derived from any of the seven major FMDV antigenically distinct virus serotypes, i.e., A, O, C, Asia 1 and South African Territories 1, 2 and 3 as well as the multiple subtypes or topotypes exist within each serotype. The wild-type nucleotide sequences of the P1 polyprotein precursor from various FMDV serotypes are known, for example SEQ ID NO: 11 (O1 Manisa isolate 87), SEQ ID NO: 12 (Type A (A/IRN/1/96)), SEQ ID NO: 13 (Type C (Haute Loire FR/69)), SEQ ID NO: 14 (SAT3 ZAM/04/96/3), SEQ ID NO: 15 (SAT2 SEN/05/75), SEQ ID NO: 16 (SAT1 NIG/15/75) and SEQ ID NO: 17 (Asia 1 IND 63/72).

The present disclosure further provides vectors or vehicles containing the transgene expression cassette. Example vectors include, but are not limited to, circular or linear, single- or double-stranded, natural or engineered extrachromosomal plasmid vectors, cosmids, viral vectors, expression vectors, gene transfer vectors, minicircle vectors, and artificial chromosomes and typically contain at least an origin of replication, a cloning site and a selectable marker (e.g., antibiotic resistance). Natural versions of the foregoing examples may be isolated, purified, and/or modified so the resultant natural version is differentiable from the material in its natural state.

In an embodiment, the vector used for transferring the transgene expression cassette is a minicircle DNA vector. A "minicircle DNA vector" may be referred to as "minicircle vector" or "minicircle" is a small (usually in the range of 3-4 kb, approximately 3-4 kb or usually no larger than 10 kb) circular, episomal plasmid derivative wherein all prokaryotic vector parts (e.g., bacterial origin of replication, genes associated with bacterial propagation of plasmids) have been removed. Since minicircle vectors contain no prokaryotic DNA sequences, they are less likely to be perceived as foreign and destroyed when they are employed as vehicles for transferring transgenes into target mammalian cells. In embodiments, a minicircle DNA vector is a minicircle carrying a transgene expression cassette. In examples, a minicircle DNA vector is a minicircle carrying a transgene expression cassette and does not contain an empty vector without an insert.

The use of a minicircle DNA vector to carry and transfer the transgene expression cassette allows mammalian cells to be transfected (e.g., directly) without utilizing an intermediate eukaryotic host system (e.g., insect cell line production system). In embodiments, "transfection" is the process of deliberately introducing nucleic acid into eukaryotic cells, such as animal cells. Transfection can eliminates the costs and labor associated with maintaining large volumes of intermediate host cell cultures in production facilities and harvesting empty capsids or VLPs produced by intermediate host cells.

Furthermore, the size of minicircle vectors (which are smaller than standard plasmid vectors) and the lack of extraneous bacterial sequences enhance transfection of cells and enable an extended duration of transgene expression within the mammalian host cell. For example, a minicircle vector is smaller than a standard vector as it lacks extraneous bacterial sequences found on plasmids. Differences in size between plasmid vectors and minicircle vectors can be attributed to the lack of extraneous bacterial sequences, inclusion of an insubstantial amount of extraneous bacterial sequences in comparison to the overall size of the vector, such as appreciably smaller in comparison to the plasmid, and variations thereof. Prolonged high levels of transgene expression by minicircles in mammalian hosts can also be facilitated by in the incorporation of strong and constitutive promoters such as SV40, CMV, UBC, EF1A, PGK and CAGG.

In one or more embodiments, the nucleotide sequence of a minicircle containing the transgene expression cassette comprises SEQ ID NO: 3.

The present disclosure additionally provides methods of producing minicircle vectors that are capable of inducing production of FMDV virus-like particles in mammalian host cells and methods of vaccinating a mammalian subject with the minicircle vectors.

Minicircle vectors are prepared using a two-step procedure. Firstly, a full-size parental plasmid containing bacterial sequences and transgene is produced in, for example, *Escherichia coli*. While the parental plasmid is still inside the *E. coli* host, the expression of a site-specific recombinase is induced and the prokaryotic or bacterial bone is excised by the enzyme at the recombinase recognition sites. Examples of site-specific recombinases include Tyr- and Ser-recombinases such as Cre recombinase, Flp recombinase, ParA resolvase and PhiC31 integrase. The resulting minicircle vector is recovered by capillary gel electrophoresis. An example of suitable materials, techniques, approaches, and methods are described in U.S. Pat. No. 8,236,548 which is hereby incorporated by reference in its entirety. Further description may be found in Kay et al, *A Robust System for Production of Minicircle DATA Vectors*, Nature Biotechnology, 2010 28:1287-1289, which is hereby incorporated by reference in its entirety.

A vaccine in embodiments in accordance with the present disclosure is a biological composition that provides or improves immunity to an organism to a particular disease. A vaccine may contain an agent, such as a killed, inactivated, weakened or attenuated form of the disease-causing microorganism (e.g., virus, bacteria, fungi, algae), its toxins, surface proteins or recombinant nucleic acid such as DNA, compositions or particles that resemble the pathogenic microorganism (e.g., virus-like particles) or combinations thereof. The agent functions as an antigen and is administered to an organism to stimulate the body's immune system produce an immune response, which may include recognizing the agent as foreign, destroying the agent (e.g., with antibodies produced that are specific to the agent/antigen), and remembering the agent, so the immune system can more easily recognize and destroy any of these microorganisms that it later encounters, for example, an infection.

Virus-like particles, or VLPs, can be used in accordance with embodiments of the present disclosure. VLPs are recombinant particles viral matrix or structural proteins such as capsids that resemble viruses, but are non-infectious and unable to propagate as they, respectively, do not contain any viral genetic material. VLPs can be utilized as vaccine antigens as they mimic the native virions, and can be produced in vitro in a variety of cell culture systems including mammalian cell lines, insect cell lines, yeast and plant cells or in vivo. In embodiments, FMDV VLPs consist essentially of assembled structural proteins or assembled capsid proteins (e.g., VP1, VP2, VP3 and VP4).

In DNA vaccination, an organism is protected against a disease by injecting it with genetically engineered DNA (e.g., transgene+vector) to produce an immune response. DNA vaccines have a number of advantages over traditional whole-pathogen vaccines and protein-based vaccines. For example, DNA vaccines do not contain an actual infectious agent, whether dead or alive. DNA vaccines can also be easily lyophilized for long-term storage and transportation and do not require any cold chain delivery.

The DNA vector inside a DNA vaccine can be produced and modified more quickly and more easily in comparision to traditional vaccine preparation. This allows a more rapid response to specifically engineer DNA vaccines tailored to individual FMD outbreaks (e.g., a DNA vaccine matching a specific FAMDV outbreak strain or serotype). Using a minicircle DNA vector to carry and transfer the transgene expression cassette eliminates the use of an intermediate eukaryotic host system and the associated costs and labor, including modification of an intermediate host system during and outbreak, such as during the onset of an FMD outbreak.

Routes of DNA vaccine administration include, but are not limited to, traditional injection methods in saline (e.g. subcutaneous, intradermal and intramuscular injections), jet injection, oral administration, skin patches, aerosol inhalation or instillation, topical administration to the eye, electroporation, gene gun, transfection, liposome-mediated delivery or combinations thereof.

An FMD DNA vaccine in accordance with embodiments of the present disclosure are administered at dosages such as in the range of 25-1000 μg of the minicircle DNA vector in saline solution or another appropriate diluent, in the range of between 50-500 μg in the range of 100-250 μg. A variety of factors can form the basis of what dosage range to implement. Examples of factors that influence dosage amount include, but are not limited to, the size of the subject, how virulent the FMD strain that is being inoculated against is, and so forth. The FMD DNA vaccine and/or the method of vaccinating a mammalian subject with the vaccine protects the subject against one or more of the O, A, C, Asia 1, SAT 1, SAT 2 and SAT 3 serotypes of the FMD virus.

The FMD DNA vaccines formulated with compositions and methods described herein may be used prophylactically (e.g., to prevent or ameliorate the effects of a future infection), therapeutically (e.g., to treat or to empower the immune system of an infected organism) or both.

FMD vaccines in accordance with the present disclosure are marker vaccines or DIVA (Differentiating Infected from Vaccinated Animals), which induce immune responses that differ from those caused by natural infection. These differences are reflected in antibody profiles, and can be detected by diagnostic tests and assays such as enzyme linked immunosorbent assays (ELISAs) containing the same compositions used in the vaccine formulations. The DIVA strategy is useful in eradication scenarios wherein emergency vaccination using DIVA FMD vaccines could be an effective control tool for FMD outbreaks in densely populated livestock areas. DIVA vaccination can limit the number of culled animals in the process of FMD eradication, thereby enhancing public acceptance for disease control measures and limiting economic losses.

The minicircle vector DNA vaccine platform for FMD, as described herein, may be used with or without adjuvants. In certain embodiments, the FMD DNA vaccines further include one or more compounds selected from an adjuvant, a diluent or a carrier. Example adjuvants include, but are not limited to, aqueous-based aluminum hydroxide gel-saponin, the oil-based Montanide ISA 206, other aluminum-based adjuvants and incomplete Freunds adjuvant (IFA). Example diluents include, but are not limited to, water, physiological saline solution, human serum albumin, oils, polyethylene glycols, glycerin, propylene glycol or other synthetic solvents, antibacterial agents such as benzyl alcohol, antioxidants such as ascorbic acid or sodium bisulfite, chelating agents, such as ethylene diamine-tetra-acetic acid, buffers such as acetates, citrates or phosphates and agents for adjusting osmolarity, such as sodium chloride or dextrose.

Example carriers lude, but are not limited to, liquid carriers water, saline, culture medium, saline, aqueous dextrose, aqueous glycols) and solid carriers (e.g., carbohydrates such as starch, glucose, lactose, sucrose, dextrans; anti-oxidants such as ascorbic acid and glutathione, hydrolyzed proteins).

An FMD DNA vaccine's efficacy in embodiments is considered the rate of reduction in the incidence of serotype-specific FMD among a population of subjects that have been vaccinated compared to the incidence in a population of unvaccinated subjects, over a duration of 12 months. Vaccine efficacy (VE) can measured using the following formula:

$$VE=[(ARU-ARV)/ARU]\times 100\%$$

where "VE" is vaccine efficacy, "ARU" is an attack rate in an unvaccinated population and "ARV" is an attack rate in the vaccinated population.

FMD DNA vaccines comprising the minicircle DNA vector in accordance with the present disclosure exhibit VE values of between 50-95%, approximately 50%, greater than 50%, 50%, approximately 75%, approximately 75%, greater than 75%, approximately 90%, greater than 90%, 95%, approximately 95%, or greater than 95%.

The examples below are intended to further illustrate protocols for preparing and characterizing the transgene expression cassette and the minicircle vector carrying the transgene expression cassette, and are not intended to limit the scope of the claims. While these examples are provided for explanatory purposes, these should not be considered the only examples. Additional examples will be apparent based on the teachings of the present disclosure.

EXAMPLE 1

Construction of Inserts and Production of Minicircle Vectors

Figure 4:
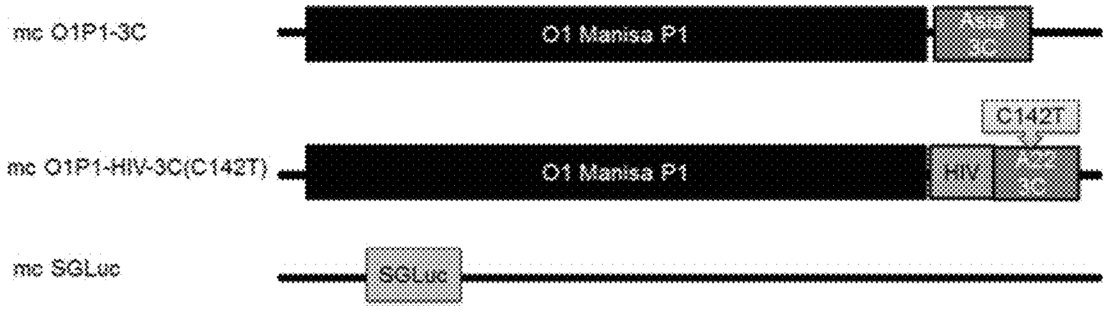
FIG. 4 illustrates gene layouts of three inserts that were each individually cloned into a minicircle vector system.

Three insert constructs, as may be seen in FIG. 4 and outlined below, were constructed, individually cloned and evaluated in a minicircle vector system in accordance with this disclosure.

The O1P1-3C(wt) insert (SEQ ID NO: 18) includes the mutant FMDV P1 polypeptide from FMDV O1 Manisa isolate 87 (SEQ ID NO: 1) with a wild-type Asia Lebanon 89 3C protease sequence for processing (SEQ ID NO: 7). This arrangement mirrors that used in FMDV adenovirus vaccine constructs. Examples include Mayr et al., *Immune Responses And Protection Against Foot-And-Mouth Disease Virus (FMDV) Challenge in Swine Vaccinated With Adenovirus-FMDV Constructs*, Vaccine, 2001 19:2152-62; Moraes et al., *Early Protection Against Homologous Challenge After a Single Dose of Replication-Defective Human Adenovirus Type 5 Expressing Capsid Proteins of Foot-And-Mouth Disease Virus (FMDV) Strain A24*, *Vaccine,* 2002 20:1631-9; Pacheco et al., *Rapid Protection of Cattle From Direct Challenge With Foot-And-Mouth Disease Virus (FMDV) by a Single Inoculation With An Adenovirus-Vectored FMDV Subunit Vaccine,* Virology, 2005 337:205-9. All of the foregoing articles are incorporated by reference in their entirety.

The O1P1-HIV-3C(C142T) insert (SEQ ID NO: 19) utilizes the mutant FMDV P1 polypeptide from FMDV O1 Manisa isolate 87 (SEQ ID NO: 1), the HIV frameshift element (SEQ ID NO: 6) with an A22 Iraq strain 3C protease containing a C142T mutation (SEQ ID NO: 9).

The wild-type nucleotide sequence of FMDV O1 Manisa isolate 87 P1 coding region comprises SEQ ID NO: 11.

The SGLuc insert (SEQ ID NO: 20) expresses the 8990 variant of Gaussia luciferase (SGLuc), such as that described in Kim et al, *Superluminescent Variants of Marine Luciferases for Bioassays*, Analytical Chemistry. 2011 83:8732-40, which is hereby incorporated herein by reference in its entirety. The SGLuc insert provides both a negative control for FMDV protein expression and a positive control for transfection efficiency due to its luciferase activities.

The Kozak eukaryotic translation initiation nucleotide sequence (SEQ ID NO: 5) is positioned 5' to each of the O1P1-3C(wt) (SEQ ID NO: 18), O1P1-HIV-3C(C142T) (SEQ ID NO: 19) and SGLuc insert constructs (SEQ ID NO: 20). With the O1P1-3C(wt) and O1P1-HIV-3C(C142T) inserts, the Kozak eukaryotic translation initiation nucleotide sequence is positioned 5' to mutant nucleotide sequence of FMDV P1 polypeptide from FMDV O1 Manisa isolate 87 (SEQ ID NO: 1).

To produce the pMC-CMV-SV40-polyA O1P1-HIV-3C (C142T) minicircle vector, the parental plasmid pMC-CMV-MCS-SV40-polyA (System Biosciences, catalog number MN501A-1) was digested with BamHI and EcoRI restriction enzymes according to manufacturer's instructions. The nucleotide sequence for the O1P1-HIV-3C(C142T) construct was synthesized and digested with BamHI and EcoRI restriction enzymes according to manufacturer's instructions for insertion into the pMC.CMV-MCS-SV40-polyA parental plasmid. A ligation reaction was performed using T4 DNA Ligase with a 3:1 insert to vector ratio as per manufacturer's instructions.

A ligation reaction was used to transform 5-alpha Competent *E. coli* (High Efficiency) as per manufacturer's instructions. The cells were plated on 50 μg/mL Kanamycin LB agar plates. Colonies were picked and grown in growth medium with kanamycin, overnight in a 37° C. shaker. Plasmids were purified using a miniprep kit according to manufacturer's protocols. Sequencing was performed to confirm mutation free insertion using the following primers: O1MSeq1-F (SEQ ID NO: 21), O1MSeq2-F (SEQ ID NO: 22), O1MSeq3-F (SEQ ID NO: 23), O1MSeq4-F (SEQ ID NO: 24), O1MSeq5-F (SEQ ID NO: 25), O1MSeq6-F (SEQ ID NO: 26), O1MSeq7-F (SEQ ID NO: 27), O1MSeq8-F (SEQ ID NO: 28), O1P1-Seq-R1 (SEQ ID NO: 29) and O1P1-Seq-R2 (SEQ ID NO: 30).

Alternatively, competent *E. coli* cells from the ZYCY10P3S2T *E. coli* strain were transformed by adding DNA from the ligation reaction to the competent cells that have been thawed on ice, incubating the cells on ice for 30 minutes (min), heat-shocking the cells for 30 s in a 42° C. water bath without shaking and placing the cells on ice again for 2 min. The transformed *E. coli* cells were recovered by adding 0.2 ml of room temperature Super Optimal Broth with Catabolit repression (SOC) medium to the cells and incubating at 30° C. or 37° C. for 60-90 min with shaking at 250 revolutions per minute (rpm). After that, the transformants were selected on LB plates containing 50 μg/μl kanamycin and 10 mM L-arabinose. Transformants that formed colonies after the overnight incubation had their minicircle vectors extracted by standard miniprep. The extracted minicircle vector samples were examined by restriction digest analysis and sequencing with the aforementioned primers.

The ZYCY10P3S2T *E. coli* strain harbors an arabinose-inducible system to express the PhiC31 integrase and I-SceI endonuclease (both integrase and endonuclease genes are found on the parental plasmid). The PhiC31 integrase excises the prokaryotic parts from the parental plasmid, thus forming a "bacterial backbone" and the pMC-CMV-SV40-polyA O1P1HIV-3C(C142T) minicircle vector containing the transgene expression cassette. In one or more embodiments, the nucleotide sequence of the "bacterial backbone" and the pMC-CMV-SV40-polyA O1P1-HIV-3C(C142T) minicircle vector containing the transgene expression cassette comprises SEQ ID NO: 31. The bacterial backbone, containing signals for methylation transgene silencing, is recognized and ultimately degraded by the expressed I-SceI endonuclease. The elements that remain in the polyA O1P1-HIV-3C(C142T) minicircle vector include the Cytomegalovirus (CMV) promoter to drive high and sustained levels of gene expression and the Simian virus 40 (SV40) PolyA signal for transcription termination. In one or more embodiments, the pMC-CMV-SV40-polyA O1P1-HIV-3C(C142T) minicircle vector containing the transgene expression cassette comprises SEQ ID NO: 3.

To create the O1P1-3C(wt) construct the previously constructed O1P1-HIV-3C(C142T) construct was digested with NotI and EcoRI restriction enzymes according to manufacturer's instructions. PCR was performed according to manufacturer's instructions with primers NotI-3CLeb89-F (SEQ ID NO: 32) and 3CLeb89-EcoRI-R (SEQ ID NO: 33) using a template plasmid containing the 3C nucleotide sequence from FMDV Asia Lebanon 1989 strain. PCR product was digested with NotI and EcoRI restriction enzymes according to manufacturer's instructions. Ligation, transformation, plasmid purification, and sequencing were performed as described above. In one or more embodiments, the nucleotide sequence of the "bacterial backbone" and the pMC-CMV-SV40-polyA O1P1-3C(wt) minicircle vector containing the transgene expression cassette comprises SEQ ID NO: 34. In one or more embodiments, the pMC-CMV-SV40-polyA O1P1-3C(wt) minicircle vector containing the transgene expression cassette comprises SEQ ID NO: 35.

To create the SGLuc construct a pTarget construct containing the SGLuc nucleotide coding sequence was digested with BamHI and EcoRI restriction enzymes according to manufacturer's instructions. Ligation, transformation, and plasmid purification was performed as described above. Sequencing was performed using primers AscI-Kzk-Gluc-F (SEQ ID NO: 36) and Gluc-R-NotI (SEQ ID NO: 37). In one or more embodiments, the "bacterial backbone" and the pMC-CMV-SV40-polyA SGLuc minicircle vector containing the transgene expression cassette comprises SEQ ID NO: 38. In one or more embodiments, the pMC-CMV-SV40-polyA SGLuc minicircle vector containing the transgene expression cassette comprises SEQ ID NO: 39.

EXAMPLE 2

Transfection of the Minicircle Vectors Into Mammalian Cells and VLP Production The pMC-CMV-SV40-polyA O1P1-3C(wt) (SEQ ID NO: 35), pMC-CMV-SV40-polyA O1P1-HIV-3C(C142T) (SEQ ID NO: 3) and pMC-CMV-SV40-polyA SGLuc (SEQ ID NO: 39) minicircle vectors produced in Example 1 were transfected into the mammalian cell line LF-BK αV/β6 using a commercially available transfection reagent. LF-BK αV/β6 cells were cultivated in six well plates until 95% confluent. Transfections were performed with 4 μg of minicircle DNA according to the manufacturer's protocol. Additionally, HEK293-T cells at passage 71 at roughly 90% confluence were transfected with the minicircle vectors using a transfection reagent and 4 μg of the minicircle vectors as per manufacturer's instructions. Transfected cell cultures were allowed to sit at 37° C. for 24 hour (h) in a $CO_2$ incubator.

EXAMPLE 3

Evaluation of Expression by Luciferase Assay

To evaluate expression of the pMC-CMV-SV40-polyA SGLuc minicircle vector, a luciferase assay was utilized to detect for luminescence. A luminescence assay was performed on a 96-well luminometer using 20 μl of harvested media without delay after injection of 25 μl of 100 μM water soluble coelenterazine solution and an integration of 0.5 s. Readings were taken both before and after injection of coelenterazine. During analysis of the data, readings for before injection were used to establish a baseline of light emission at the time of injection and were subsequently subtracted from post-injection values. Replicates were averaged together to give an overall luciferase reading in relative luciferase units per half second (RLU/0.5 s).

Figure 5:
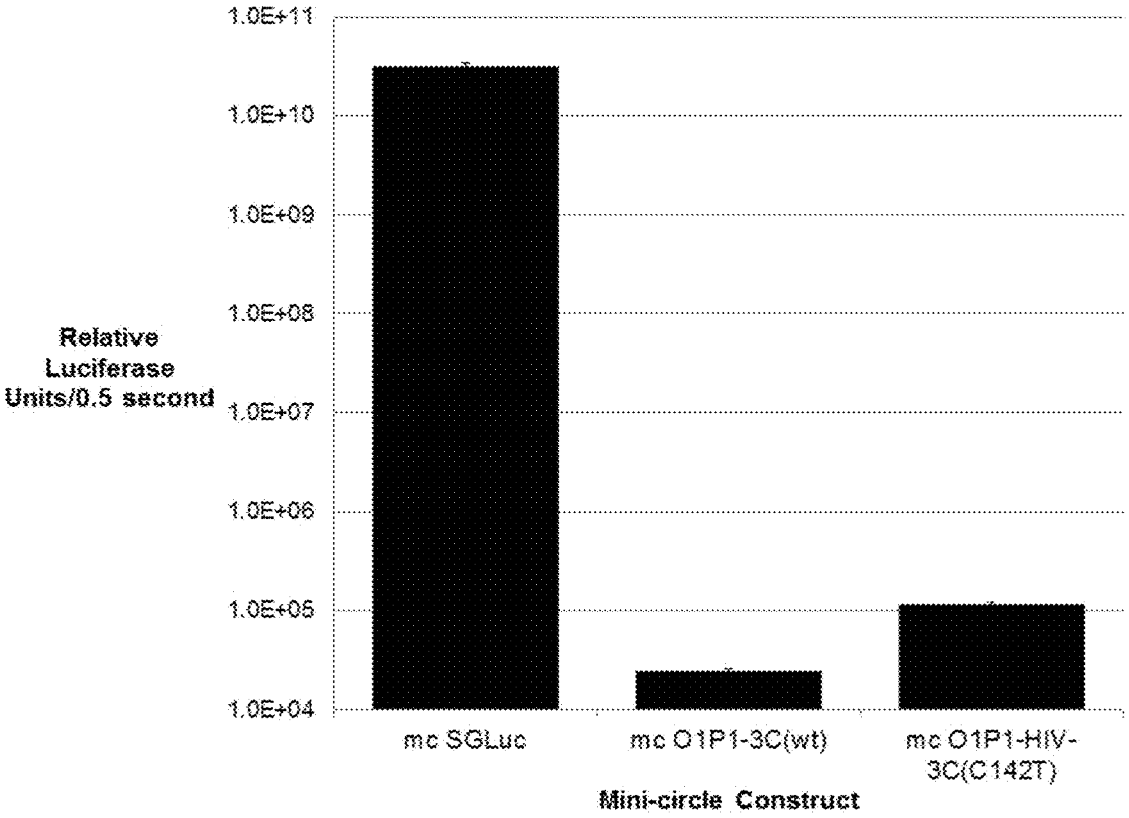
FIG. 5 is a bar graph of luciferase reading from cell culture media harvested off of transfected HEK239-T cells. The Y axis represents Relative Luciferase Units (RLU)/0.5 second (s), and the X axis represents the mc SGLuc, mc O1P1-3C(wt) and me O1P1-HIV-3C(C142T) Mini-circle Constructs.

Media from transfected HEK293-T cells was harvested and checked for luciferase activity to confirm transfection, as shown in FIG. 5. As expected only cells transfected with the SGLuc insert construct showed luciferase activity.

EXAMPLE 4

Evaluation of Expression and P1 Processing by Western Blotting

Figure 6:
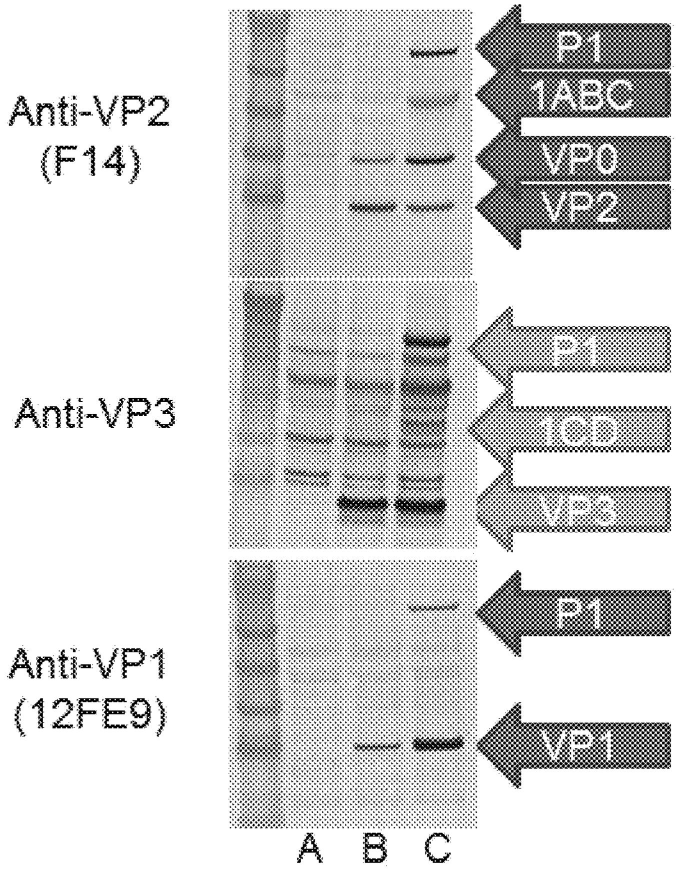
FIG. 6 is a western blotting image of transfected cells reacted with F14 anti-VP2, anti-VP3 and 12FE9 antibodies to examine FMDV P1 processing in transfected cells.

Transfected HEK293-T cells lysates was examined by western blotting to confirm expression and processing of FMDV proteins as shown in FIG. 6. Three different antibodies were used to examine processing. Each of the antibodies was chosen to react with a different capsid protein. Two mouse monoclonal antibodies, F14 and 12FE9, and one rabbit polyclonal antibody against FMDV VP3 were used. The F14 mouse monoclonal antibody reacts with the FMDV VP2 protein while the 12FE9 mouse monoclonal antibody reacts with VP1.

To evaluate processing, transfected cell lysates were harvested from 6 well plates using 250 μl of mammalian protein extraction reagent. Samples were mixed with a loading buffer to make a final concentration of 1×. 16 μl of the mixed samples were loaded onto 4-12% Bis-Tris protein gels and run according to manufacturer's instructions. Transfer of the protein gel to membranes was performed using a western blot.

Membranes were incubated in 5% milk blocking buffer solution for 1 h while shaking at room temperature. Membranes were rinsed two times with 1×PBS-T and washed for five min with 1×PBS-T while shaking at room temperature. Primary antibodies were diluted in 1×-PBS-T and applied to membranes for 1 h at room temperature. Primary antibodies used were 1:50 mouse monoclonal F14 (anti-VP2), 1:250 rabbit polyclonal anti-VP3, and 1:50 mouse monoclonal 12FE9 (anti-VP 1). After incubation membranes were washed for five min with PBS-T for three times. Secondary antibodies were diluted in 1×PBS-T and applied to the membranes for 1 h at room temperature. Secondary antibodies used are a 1:500 dilution ratio of goat HRP conjugated anti-mouse (KPL) and a 1:500 dilution ratio of goat HRP conjugated anti-rabbit. After incubation membranes were washed for five min with PBS-T for three times. A solution of 3',3'-Diaminobenzidine made using 3,3'-Diaminobenzidine tablets was applied to membranes and incubated while shaking at room temperature until the appearance of bands.

As shown in FIG. 6, examination of cell lysates from cells transfected with the O1P1-3C(wt) construct shows full processing of all 3C dependent junctions. VP0 is present in O1P1-3C(wt) cell lysate. However the band is less intense than that of the VP2 band suggesting that there is a greater concentration of fully processed VP2 than unprocessed VP0 in the sample. Still referring to FIG. 6, the O1P1-HIV-3C (C142T) insert construct does not show complete processing of VPs as confirmed through the presence of detectable levels of unprocessed intermediates. The only unprocessed intermediate not observed is a 1ABCD fusion which would be hard to differentiate from the P1 polypeptide on the blots due to high and similar molecular weights. Additionally we see a more intense band representing VP0 than representing VP2 suggesting that there is more unprocessed VP0 in the sample than that of VP2, an inversion of what is observed with the O1P1-3C(wt) construct.

Given that the HIV-1 frameshift sequence reduces overall expression of 3C in the O1P1-HIV-3C(C142T) construct the presence of unprocessed intermediates is not surprising. The reduction of 3C expression lowers the level of 3C present which can process host proteins providing a benefit to the host cell. However it also reduces the amount of 3C available to process the FMDV VPs.

EXAMPLE 5

Evaluation of Transfected Cells by Immunofluorescent Antibody Staining (IFA) and Transmission Electron Microscopy (TEM)

As the presence of processed P1 does not ensure the formation of VLPs, transfected LF-BK αV/β6 cells were examined at 24 and 48 h post-transfection using WA staining and TEM to confirm the production of FMDV VLPs. An electron microscopy image showing FMDV VLPs in crystalline array is shown in FIG. 7.

HEK293-T cells were incubated to adhesion on a collagen coated slide, dried, then fixed at −20° C. with 1:1 acetone: methanol. Samples were blocked with 10% FBS in PBS. Antibody 12FE9 was used at a 1:10 dilution for primary staining. Secondary staining used 1:250 anti-mouse secondary antibody. Mounting media with DAPI (Molecular Probes P36935) was applied.

HEK293-T cells were grown in T-75 flasks for transmission electron microscopy (TEM). Cells were fixed in 2% glutaraldehyde in NaHCa (Heuser's) buffer, post-fixed with 1% tannic acid followed by 1% osmium tetroxide, en-bloc stained with 4% uranyl acetate, embedded in 2% agarose, dehydrated through graded series of acetone, and embedded in Spurr's resin. Ultrathin (80 nm) sections were cut on a ultramicrotome (e.g., Leica UC6), stained with uranyl acetate and lead citrate, and imaged on a transmission electron microscope (e.g. Hitachi 7600) with a 2k×2k AMT camera at 80 kV.

Figure 7:
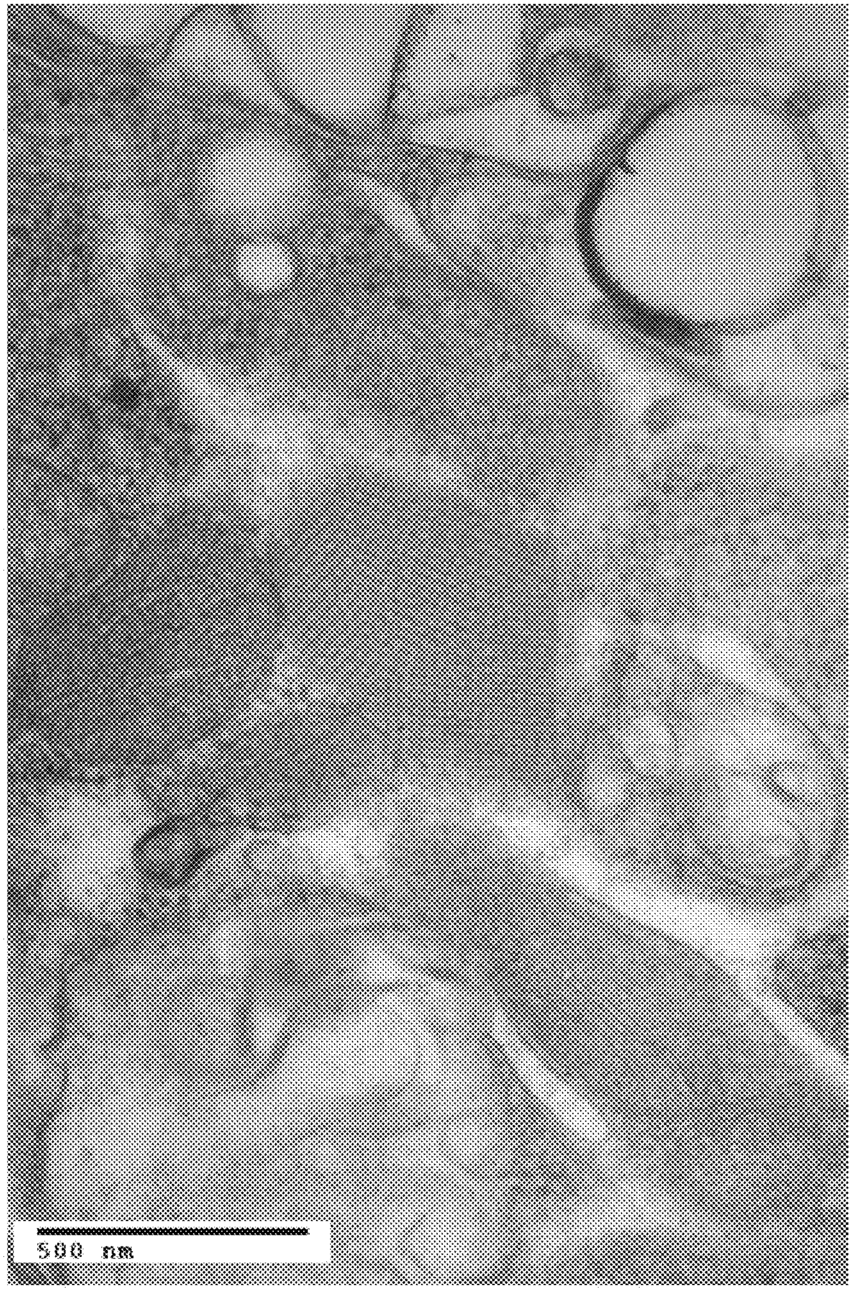
FIG. 7 is a transmission electron microscopy image showing formation of FMDV VLP arrays of HEK293-T cells transfected with pMC-CMV-SV40-polyA O1P1-3C (wt) minicircles.
Figure 8A:
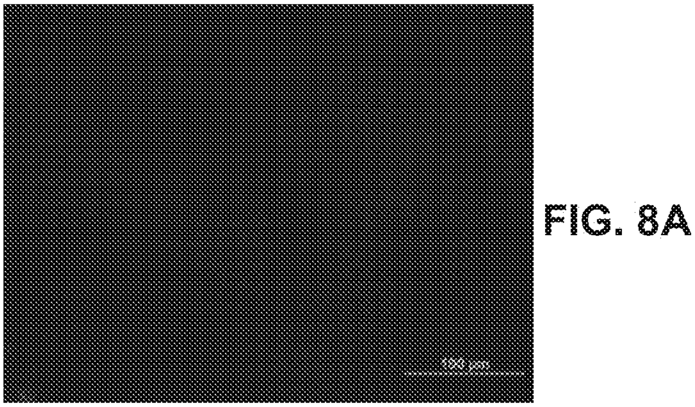
FIG. 8A is an image of IFA staining of HEK293-T cells transfected with pMC-CMV-SV40-polyA SGLuc minicircles using 12FE9 antibody.

Similarly, to confirm the presence of VLPs generated off of minicircles, transfected HEK293-T cells were examined using TEM (see FIG. 7). IFAs were performed on transfected cells to ensure the presence of expressed proteins in transfected cell lines (see FIGS. 8A-8C). The IFAs showed expression of FMDV proteins in both constructs that contained the FMDV P1 polypeptide (FIGS. 8B and 8C) and no expression in cells transfected with the mc SGLuc construct (FIG. 8A). This is in agreement with results seen in previously performed western blots in FIG. 6.

Fluorescence in the pMC-CMV-SV40-polyA O1P1-3C (wt) samples was localized largely in aggregates while fluorescence in pMC-CMV-S0-polyA O1P1-HIV-3C (C142T) samples was much more diffused through the whole cell. This suggests that transgene expression in O1P1-3C(wt) transfected samples is more structured and localized.

Figure 8B:
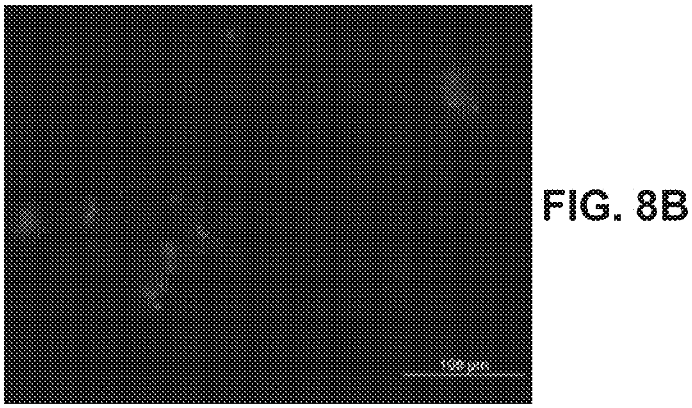
FIG. 8B is an image of IFA staining of HEK293-T cells transfected with pMC-CMV-SV40-polyA O1P1-3C(wt) minicircles using 12FE9 antibody.
Figure 8C:
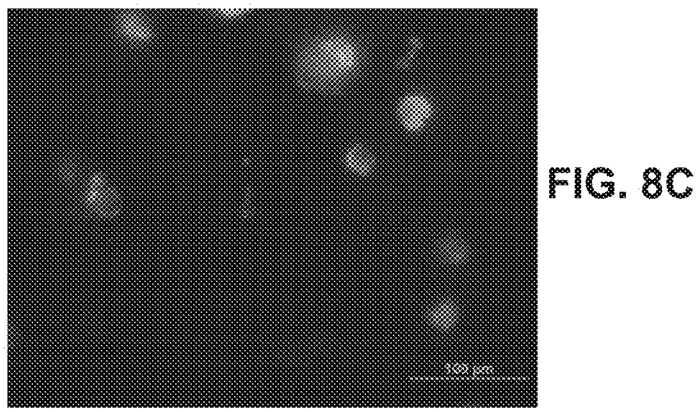
FIG. 8C is an image of IFA staining of HEK293-T cells transfected with pMC-CMV-SV40-polyA O1P1-HIV-3C (C142T) minicircles using 12FE9 antibody.

FIG. 7, the transmission electron microscopy image shows formation of FMDV VLP arrays of HEK293-T cells transfected with pMC-CMV-SV40-polyA O1P1-3C(wt). This aligns with the difference in fluorescence distribution between pMC-CMV-SV40-polyA O1P1-3C(wt) and pMC-CMV-SV40-polyA O1P1-HIV-3C(C142T) samples as seen in FIGS. 8B and 8C, respectively. This difference in distribution is also probably related to the lack of complete processing observed in pMC-CMV-SV40-polyA O1P1-HIV-3C(C142T) samples in FIG. 6. The observance of VLP arrays in the pMC-CMV-S0-polyA O1P1-3C(wt) sample does confirm that VLP formation using a minicircle vector is viable. Previous publications using the HIV frameshift in conjunction with the FMDV 3C, (Porta C, Xu X, Loureiro S, Paramasivam S, Ren J, Al-Khalil T, et al. *Efficient production of foot-and-mouth disease virus empty capsids in insect cells following down regulation of* 3C *protease activity*. Journal of Virological Methods. 2013 187:406-12, incorporated herein by reference in its entirety), observed VLPs after utilizing sucrose gradient purification to concentrate any VLPs produced prior to observation with TEM. It is possible that this additional purification and subsequent concentration of the samples aids in VLP detection by TEM.

The foregoing discussion discloses embodiments in accordance with the present disclosure. As will be understood by those skilled in the art, the approaches, methods, techniques, materials, devices, and so forth disclosed herein may be embodied in additional embodiments as understood by those of skill in the art, it is the intention of this application to encompass and include such variation. Accordingly, this disclosure is illustrative and should not be taken as limiting the scope of the following claims.

What is claimed:

1. A method of vaccinating a mammal against a foot-and-mouth disease virus (FMDV), the method comprising administering a vector comprising a mutant nucleotide sequence which when expressed in a host cell of the mammal induces production of FMDV virus-like particles (VLP) by the host cell, wherein the mutant nucleotide sequence encodes a FMDV capsid polyprotein precursor comprising one or more silent mutations to a nucleotide sequence encoding a wild-type FMDV capsid polyprotein precursor that removes one or more restriction enzyme recognition sites, wherein all occurrences of said one or more restriction enzyme recognition sites are removed from the nucleotide sequence.

2. The method of claim 1, wherein the mutant nucleotide sequence comprises at least one of one through twenty-two (1-22) silent mutations, one through fifteen (1-15) silent mutations, or one through ten (1-10) silent mutations that remove one or more restriction enzyme recognition sites.

3. The method of claim 2, wherein said one of one through twenty-two (1-22) silent mutations, one through fifteen (1-15) silent mutations, or one through ten (1-10) silent mutations are selected from the group consisting of C99, C285, T345, G354, A369, C408, C468, G498, C528, A588, C597, C627, C957, G1170, T1518, C1578, T1593, C1665, C1836, C2010, A2190, and combinations thereof.

4. The method of claim 2, wherein said one of one through twenty-two (1-22) silent mutations, one through fifteen (1-15) silent mutations, or one through ten (1-10) silent mutations are selected from the group consisting of C99T, C285T, T345A, G354A, A369G, C408T, C468A, G498A, C528T, A588T, C597T, C627T, C957A, G1170C, T1518C, C1578A, T1593A, C1665G, C1836G, C2010T, A2190T, and combinations thereof.

5. The method of claim 1, further comprising administering an adjuvant with the vector.

6. A method for determining whether a mammal is vaccinated against or infected with foot-and-mouth disease virus (FMDV), the method comprising:

a. detecting a first antibody's presence in a sample from the mammal; and b. detecting a second antibody's presence or absence in the sample, wherein presence of the first antibody and absence of the second antibody indicates vaccination of the mammal with a vector comprising a mutant nucleotide sequence which when expressed in a host cell of the mammal induces production of FMDV virus-like particles (VLP) by the host cell, wherein the mutant nucleotide sequence encodes a FMDV capsid polyprotein precursor comprising one or more silent mutations to a nucleotide sequence encoding a wild-type FJDV capsid polyprotein precursor that removes one or more restriction enzyme recognition sites, wherein all occurrences of said one or more restriction enzyme recognition sites are removed from the nucleotide sequence.

7. The method of claim 6, wherein the mutant nucleotide sequence comprises at least one of one through twenty-two (1-22) silent mutations, one through fifteen (1-15) silent mutations, or one through ten (1-10) silent mutations that remove one or more restriction enzyme recognition sites.

8. The method of claim 7, wherein said one of one through twenty-two (1-22) silent mutations, one through fifteen (1-15) silent mutations, or one through ten (1-10) silent mutations are selected from the group consisting of C99, C285, T345, G354, A369, C408, C468, G498, C528, A588, C597, C627, C957, G1170, T1518, C1578, T1593, C1665, C1836, C2010, A2190, and combinations thereof.

9. The method of claim 7, wherein said one of one through twenty-two (1-22) silent mutations, one through fifteen (1-15) silent mutations, or one through ten (1-10) silent mutations are selected from the group consisting of C99T, C285T, T345A, G354A, A369G, C408T, C468A, G498A, C528T, A588T, C597T, C627T, C957A, G1170C, T1518C, C1578A, T1593A, C1665G, C1836G, C2010T, A2190T, and combinations thereof.

10. The method of claim 6, wherein the mammal produced the first antibody responsive to vaccination with the vector.

11. The method of claim 6, wherein the second antibody comprises a plurality of antibodies that do not include the first antibody.

12. The method of claim 11, wherein the plurality of antibodies comprises at least one antibody against FMDV non-structural proteins.

13. The method of claim 11, wherein the plurality of antibodies are associated with FMDV infection.

14. The method of claim 6, wherein detecting the first antibody's presence utilizes an immunoassay.

15. The method of claim 14, wherein the immunoassay comprises an enzyme linked immunosorbent assay (ELISA).

16. The method of claim 6, wherein detecting the second antibody's presence or absence utilizes an immunoassay.

17. The method of claim 16, wherein the immunoassay comprises an enzyme linked immunosorbent assay (ELISA).

* * * * *

SEQUENCE LISTING

```
<160> NUMBER OF SEQ ID NOS: 39

<210> SEQ ID NO 1
<211> LENGTH: 2259
<212> TYPE: DNA
<213> ORGANISM: Artificial Sequence
<220> FEATURE:
<223> OTHER INFORMATION: P1 polyprotein precursor from FMDV O1 Manisa
      isolate 87, mutated

<400> SEQUENCE: 1

ggagccgggc aatccagccc ggcaaccggg tcacagaacc aatcaggcaa cactgggagc     60

atcatcaaca attactacat gcagcagtac caaaactcta tggacacaca acttggtgac    120

aacgctacaa gcggaggctc aaacgagggg tccacggaca caacctccac ccacacaacc    180

aacactcaga acaacgactg gttctcgaag ctggccagtt ccgctttcag cggtcttttc    240

ggcgctcttc tcgccgacaa gaaaaccgag gagaccactc ttcttgagga ccgcatcctc    300

actactcgta acggacacac cacctcgaca acccagtcga gcgtaggagt cacatacggg    360

tatgcaacgg ctgaggattt cgtgagcggg ccaaacacct ctggtcttga gaccagggtt    420

gcccaggcag agcggttctt taaaacccac ctgttcgact gggtcacaag tgacccgttc    480

ggacggtgcc acctgctaga acttccaact gaccacaaag gtgtctatgg cagcctgacc    540

gactcgtatg cttatatgag gaacggctgg gatgttgaag tcactgctgt gggaaatcag    600

ttcaatggag gatgcctgtt ggtggctatg gtgccagaac tttgctccat acagaagagg    660

gagctgtacc agctcacgct ctttcctcac cagttcatca accctcggac gaacatgaca    720

gcacacatca ctgtgccctt tgttggcgtc aaccgttatg accagtacaa ggtacacaaa    780

ccttggaccc tcgtggttat ggttgtagcc cccctgaccg tcaacagtga aggtgccccg    840

caaatcaagg tgtatgccaa catcgcacct accaacgtac acgtcgcggg tgagttccct    900

tccaaagagg ggatcttccc tgtggcttgc agcgatggtt atggcggtct ggtgacaact    960

gacccgaaaa cggctgaccc cgcttacggg aaagtgttta acccccccg caacatgttg   1020

ccggggcggt tcaccaattt tcttgacgtg gctgaggcgt gccccacgtt tctccacttc   1080

gagggtgacg tgccatacgt gaccacgaag acggattcag acagggtgct cgctcagttc   1140

gacttgtctt tggcagcaaa gcacatgtcc aacaccttcc ttgcaggtct cgcccagtac   1200

tacacacagt acagcggcac catcaacctg cacttcatgt tcacagggcc tactgacgcg   1260
```

-continued aaggcgcgtt acatgattgc gtatgctcct cctggcatgg aaccacctaa aacgccagag 1320
gcggctgccc actgcatcca tgctgaatgg gacacagggt tgaactcaaa attcacattt 1380
tcaatccctt acctttcggc ggctgattac gcttacacag cgtctgacac tgctgagacc 1440
acaaatgtac agggatgggt ttgcctgttt caaataacac acgggaaagc tgacggcgac 1500
gcactggtcg ttttggccag cgccggaaag gactttgagc tgcgcctgcc ggtggatgct 1560
cgcacacaga ctacctcagc gggcgagtca gcagaccccg tgaccgccac cgttgagaat 1620
tacggtggcg agacacaggt ccagaggcgc caacacacgg acgtgtcatt tatattagac 1680
agatttgtga aagtgacacc aaaagaccaa attaatgtat tggacctgat gcaaacccct 1740
gctcacactt tggtgggagc actccttcgt actgccactt actatttcgc tgacttagag 1800
gtggcagtga agcacgaggg aaacctcacc tgggtgccga acggggcgcc tgaagcggcg 1860
ttggacaaca ccaccaaccc aacagcttac cacaaggcac cactcacccg acttgcactg 1920
ccttacacgg cgccacaccg cgtgttggct actgtttaca acgggaacag caagtatggt 1980
gacggcacgg tggccaatgt gagaggtgat ctgcaagtgt tggcccagaa ggcggcgaga 2040
gcgctgccta cctccttcaa ctacggtgcc attaaagcta ctcgggtgac tgaactgctt 2100
taccgcatga agagggctga gacatactgt ccccggcctc ttttggccat tcacccggac 2160
caggctagac acaagcagaa gattgtggct ccggtgaaac agcttctaaa ttttgacctg 2220
ctcaaattgg cgggagatgt ggagtccaac cctgggccc 2259

<210> SEQ ID NO 2
<211> LENGTH: 3059
<212> TYPE: DNA
<213> ORGANISM: Artificial Sequence
<220> FEATURE:
<223> OTHER INFORMATION: Transgene expression cassette

<400> SEQUENCE: 2
ggatccgccg ccgccatggg agccgggcaa tccagcccgg caaccgggtc acagaaccaa 60
tcaggcaaca ctgggagcat catcaacaat tactacatgc agcagtacca aaactctatg 120
gacacacaac ttggtgacaa cgctacaagc ggaggctcaa acgaggggtc cacggacaca 180
acctccaccc acacaaccaa cactcagaac aacgactggt tctcgaagct ggccagttcc 240
gctttcagcg gtcttttcgg cgctcttctc gccgacaaga aaaccgagga gaccactctt 300
cttgaggacc gcatcctcac tactcgtaac ggacacacca cctcgacaac ccagtcgagc 360
gtaggagtca catacgggta tgcaacggct gaggatttcg tgagcgggcc aaacacctct 420
ggtcttgaga ccagggttgc ccaggcagag cggttcttta aaacccacct gttcgactgg 480
gtcacaagtg acccgttcgg acggtgccac ctgctagaac ttccaactga ccacaaaggt 540
gtctatggca gcctgaccga ctcgtatgct tatatgagga acggctggga tgttgaagtc 600
actgctgtgg gaaatcagtt caatggagga tgcctgttgg tggctatggt gccagaactt 660
tgctccatac agaagaggga gctgtaccag ctcacgctct ttcctcacca gttcatcaac 720
cctcggacga acatgacagc acacatcact gtgccctttg ttggcgtcaa ccgttatgac 780
cagtacaagg tacacaaacc ttggaccctc gtggttatgg ttgtagcccc cctgaccgtc 840
aacagtgaag gtgccccgca aatcaaggtg tatgccaaca tcgcacctac caacgtacac 900
gtcgcgggtg agttcccttc caaagagggg atcttccctg tggcttgcag cgatggttat 960
ggcggtctgg tgacaactga cccgaaaacg gctgaccccg cttacgggaa agtgtttaac 1020

-continued cccccccgca acatgttgcc ggggcggttc accaattttc ttgacgtggc tgaggcgtgc 1080
cccacgtttc tccacttcga gggtgacgtg ccatacgtga ccacgaagac ggattcagac 1140
agggtgctcg ctcagttcga cttgtctttg gcagcaaagc acatgtccaa caccttcctt 1200
gcaggtctcg cccagtacta cacacagtac agcggcacca tcaacctgca cttcatgttc 1260
acagggccta ctgacgcgaa ggcgcgttac atgattgcgt atgctcctcc tggcatggaa 1320
ccacctaaaa cgccagaggc ggctgcccac tgcatccatg ctgaatggga cacagggttg 1380
aactcaaaat tcacattttc aatcccttac ctttcggcgg ctgattacgc ttacacagcg 1440
tctgacactg ctgagaccac aaatgtacag ggatgggttt gcctgtttca aataacacac 1500
gggaaagctg acggcgacgc actggtcgtt ttggccagcg ccggaaagga ctttgagctg 1560
cgcctgccgg tggatgctcg cacacagact acctcagcgg gcgagtcagc agaccccgtg 1620
accgccaccg ttgagaatta cggtggcgag acacaggtcc agaggcgcca acacacggac 1680
gtgtcattta tattagacag atttgtgaaa gtgacaccaa aagaccaaat taatgtattg 1740
gacctgatgc aaacccctgc tcacactttg gtgggagcac tccttcgtac tgccacttac 1800
tatttcgctg acttagaggt ggcagtgaag cacgagggaa acctcacctg ggtgccgaac 1860
ggggcgcctg aagcggcgtt ggacaacacc accaacccaa cagcttacca caaggcacca 1920
ctcacccgac ttgcactgcc ttacacggcg ccacaccgcg tgttggctac tgtttacaac 1980
gggaacagca agtatggtga cggcacggtg gccaatgtga gaggtgatct gcaagtgttg 2040
gcccagaagg cggcgagagc gctgcctacc tccttcaact acggtgccat taaagctact 2100
cgggtgactg aactgcttta ccgcatgaag agggctgaga catactgtcc ccggcctctt 2160
ttggccattc acccggacca ggctagacac aagcagaaga ttgtggctcc ggtgaaacag 2220
cttctaaatt ttgacctgct caaattggcg ggagatgtgg agtccaaccc tgggcccagc 2280
ggccgcggac ctttttttagg gaagatctgg ccttcctaca agggaaggcc agggaatttt 2340
cttacgaggg accggtaaaa aaacccgtag cactcaaggt taaagcaaag aatctcattg 2400
ttaccgaaag tggagcccca ccgaccgact tgcaaaagat ggtcatgggc aacaccaagc 2460
ctgttgaact catcctcgac gggaagacgg tggccatttg ttgtgctacc ggtgtgtttg 2520
gcactgcgta cctcgtgcct cgtcatcttt ttgcagaaaa atatgacaag atcatgctgg 2580
acggcagagc catgacagac agtgactaca gagtgtttga gtttgagatt aaagtaaaag 2640
gacaggacat gctctcagac gctgcgctca tggtactcca ccgtgggaat cgcgtgagag 2700
acatcacgaa acactttcgt gacacagcaa gaatgaagaa aggcacccct gttgtcggag 2760
taatcaacaa tgccgacgtc gggagactga tcttctctgg tgaggccctt acctacaagg 2820
acattgtagt gacaatggat ggagacacca tgcctggcct gtttgcctac aaagccgcca 2880
ccaaggctgg ctactgtggg ggagccgttc ttgctaagga cggagctgac acattcatcg 2940
ttggcactca ctccgcaggc ggcaatggag ttggatactg ctcatgcgtt tccaggtcca 3000
tgttgctgaa aatgaaggcg cacatcgacc ccgaaccaca ccacgagaag taagaattc 3059

<210> SEQ ID NO 3
<211> LENGTH: 4788
<212> TYPE: DNA
<213> ORGANISM: Artificial Sequence
<220> FEATURE:
<223> OTHER INFORMATION: pMC-CMV-SV40-polyA O1P1-HIV-3C(C142T)(without bacterial backbone)

<400> SEQUENCE: 3

-continued

```
ccccttgggct ccccgggcgc gactagtgaa ttgatactag tattatgccc agtacatgac     60
cttatgggac tttcctactt ggcagtacat ctacgtatta gtcatcgcta ttaccatggt    120
gatgcggttt tggcagtaca tcaatgggcg tggatagcgg tttgactcac ggggatttcc    180
aagtctccac cccattgacg tcaatgggag tttgttttgg caccaaaatc aacgggactt    240
tccaaaatgt cgtaacaact ccgccccatt gacgcaaatg ggcggtaggc gtgtacggtg    300
ggaggtttat ataagcagag ctcgtttagt gaaccgtcag atcgcctgga gacgccatcc    360
acgctgtttt gacctccata gaagattcta gagtcgacgc ggccgcggat ccgccgccgc    420
catgggagcc gggcaatcca gcccggcaac cgggtcacag aaccaatcag gcaacactgg    480
gagcatcatc aacaattact acatgcagca gtaccaaaac tctatggaca cacaacttgg    540
tgacaacgct acaagcggag gctcaaacga ggggtccacg gacacaacct ccacccacac    600
aaccaacact cagaacaacg actggttctc gaagctggcc agttccgctt tcagcggtct    660
tttcggcgct cttctcgccg acaagaaaac cgaggagacc actcttcttg aggaccgcat    720
cctcactact cgtaacggac acaccacctc gacaacccag tcgagcgtag gagtcacata    780
cgggtatgca acggctgagg atttcgtgag cgggccaaac acctctggtc ttgagaccag    840
ggttgcccag gcagagcggt tctttaaaac ccacctgttc gactgggtca caagtgaccc    900
gttcggacgg tgccacctgc tagaacttcc aactgaccac aaaggtgtct atggcagcct    960
gaccgactcg tatgcttata tgaggaacgg ctgggatgtt gaagtcactg ctgtgggaaa   1020
tcagttcaat ggaggatgcc tgttggtggc tatggtgcca gaactttgct ccatacagaa   1080
gagggagctg taccagctca cgctctttcc tcaccagttc atcaaccctc ggacgaacat   1140
gacagcacac atcactgtgc cctttgttgg cgtcaaccgt tatgaccagt acaaggtaca   1200
caaaccttgg accctcgtgg ttatggttgt agcccccctg accgtcaaca gtgaaggtgc   1260
cccgcaaatc aaggtgtatg ccaacatcgc acctaccaac gtacacgtcg cgggtgagtt   1320
cccttccaaa gaggggatct tccctgtggc ttgcagcgat ggttatggcg gtctggtgac   1380
aactgacccg aaaacggctg accccgctta cgggaaagtg tttaaccccc cccgcaacat   1440
gttgccgggg cggttcacca attttcttga cgtggctgag gcgtgcccca cgtttctcca   1500
cttcgagggt gacgtgccat acgtgaccac gaagacggat tcagacaggg tgctcgctca   1560
gttcgacttg tctttggcag caaagcacat gtccaacacc ttccttgcag gtctcgccca   1620
gtactacaca cagtacagcg gcaccatcaa cctgcacttc atgttcacag ggcctactga   1680
cgcgaaggcg cgttacatga ttgcgtatgc tcctcctggc atggaaccac ctaaaacgcc   1740
agaggcggct gcccactgca tccatgctga atgggacaca gggttgaact caaaattcac   1800
attttcaatc ccttaccttt cggcggctga ttacgcttac acagcgtctg acactgctga   1860
gaccacaaat gtacagggat gggtttgcct gtttcaaata acacacggga aagctgacgg   1920
cgacgcactg gtcgttttgg ccagcgccgg aaaggacttt gagctgcgcc tgccggtgga   1980
tgctcgcaca cagactacct cagcgggcga gtcagcagac cccgtgaccg ccaccgttga   2040
gaattacggt ggcgagacac aggtccagag gcgccaacac acggacgtgt catttatatt   2100
agacagattt gtgaaagtga caccaaaaga ccaaattaat gtattggacc tgatgcaaac   2160
ccctgctcac actttggtgg gagcactcct tcgtactgcc acttactatt tcgctgactt   2220
agaggtggca gtgaagcacg agggaaacct cacctgggtg ccgaacgggg cgcctgaagc   2280
ggcgttggac aacaccacca acccaacagc ttaccacaag gcaccactca cccgacttgc   2340
actgccttac acggcgccac accgcgtgtt ggctactgtt tacaacggga acagcaagta   2400
```

-continued

```
tggtgacggc acggtggcca atgtgagagg tgatctgcaa gtgttggccc agaaggcggc   2460
gagagcgctg cctacctcct tcaactacgg tgccattaaa gctactcggg tgactgaact   2520
gctttaccgc atgaagaggg ctgagacata ctgtccccgg cctcttttgg ccattcaccc   2580
ggaccaggct agacacaagc agaagattgt ggctccggtg aaacagcttc taaattttga   2640
cctgctcaaa ttggcgggag atgtggagtc caaccctggg cccagcggcc gcggaccttt   2700
tttagggaag atctggcctt cctacaaggg aaggccaggg aattttctta cgagggaccg   2760
gtaaaaaaac ccgtagcact caaggttaaa gcaaagaatc tcattgttac cgaaagtgga   2820
gccccaccga ccgacttgca aaagatggtc atgggcaaca ccaagcctgt tgaactcatc   2880
ctcgacggga agacggtggc catttgttgt gctaccggtg tgtttggcac tgcgtacctc   2940
gtgcctcgtc atctttttgc agaaaaatat gacaagatca tgctggacgg cagagccatg   3000
acagacagtg actacagagt gtttgagttt gagattaaag taaaaggaca ggacatgctc   3060
tcagacgctg cgctcatggt actccaccgt gggaatcgcg tgagagacat cacgaaacac   3120
tttcgtgaca cagcaagaat gaagaaaggc acccctgttg tcggagtaat caacaatgcc   3180
gacgtcggga gactgatctt ctctggtgag gcccttacct acaaggacat tgtagtgaca   3240
atggatggag acaccatgcc tggcctgttt gcctacaaag ccgccaccaa ggctggctac   3300
tgtgggggag ccgttcttgc taaggacgga gctgacacat tcatcgttgg cactcactcc   3360
gcaggcggca atggagttgg atactgctca tgcgtttcca ggtccatgtt gctgaaaatg   3420
aaggcgcaca tcgaccccga accacaccac gagaagtaag aattcgagct cgacaatcaa   3480
cctctggatt acaaaatttg tgaaagattg actggtattc ttaactatgt tgctcctttt   3540
acgctatgtg gatacgctgc tttaatgcct ttgtatcatg ctattgcttc ccgtatggct   3600
ttcattttct cctccttgta taaatcctgg ttgctgtctc tttatgagga gttgtggccc   3660
gttgtcaggc aacgtggcgt ggtgtgcact gtgtttgctg acgcaacccc cactggttgg   3720
ggcattgcca ccacctgtca gctcctttcc gggactttcg ctttccccct ccctattgcc   3780
acggcggaac tcatcgccgc ctgccttgcc cgctgctgga caggggctcg gctgttgggc   3840
actgacaatt ccgtggtgtt gtcggggaaa tcatcgtcct ttccttggct gctcgcctgt   3900
gttgccacct ggattctgcg cgggacgtcc ttctgctacg tcccttcggc cctcaatcca   3960
gcggaccttc cttcccgcgg cctgctgccg gctctgcggc ctcttccgcg tcttcgcctt   4020
cgccctcaga cgagtcggat ctccctttgg gccgcctccc cgcctggtac ctttaagacc   4080
aatgacttac aaggcagctg tagatcttag ccacttttta aaagaaaagg ggggactgga   4140
agggctaatt cactcccaac gaagataaga tctgcttttt gcttgtactg ggtctctctg   4200
gttagaccag atctgagcct gggagctctc tggctaacta gggaacccac tgcttaagcc   4260
tcaataaagc ttgccttgag tgcttcaagt agtgtgtgcc cgtctgttgt gtgactctgg   4320
taactagaga tccctcagac ccttttagtc agtgtggaaa atctctagca gtagtagttc   4380
atgtcatctt attattcagt atttataact tgcaaagaaa tgaatatcag agagtgagag   4440
gaacttgttt attgcagctt ataatggtta caaataaagc aatagcatca caaatttcac   4500
aaataaagca tttttttcac tgcattctag ttgtggtttg tccaaactca tcaatgtatc   4560
ttatcatgtc tggctctagc tatcccgccc ctaactccgc ccatcccgcc cctaactccg   4620
cccagttccg cccattctcc gccccatggc tgactaattt tttttattta tgcagaggcc   4680
gaggccgcct cggcctctga gctattccag aagtagtgag gaggcttttt tggaggccta   4740
```

-continued gacttttgca gatcgaccca tgggggcccg ccccaactgg ggtaacct 4788

<210> SEQ ID NO 4
<211> LENGTH: 13
<212> TYPE: DNA
<213> ORGANISM: Artificial Sequence
<220> FEATURE:
<223> OTHER INFORMATION: Kozak consensus sequence
<220> FEATURE:
<221> NAME/KEY: misc_feature
<222> LOCATION: (7)..(7)
<223> OTHER INFORMATION: r is g or a

<400> SEQUENCE: 4
gccgccrcca tgg 13

<210> SEQ ID NO 5
<211> LENGTH: 13
<212> TYPE: DNA
<213> ORGANISM: Artificial Sequence
<220> FEATURE:
<223> OTHER INFORMATION: Kozak eukaryotic translation initiation sequence

<400> SEQUENCE: 5
gccgccgcca tgg 13

<210> SEQ ID NO 6
<211> LENGTH: 120
<212> TYPE: DNA
<213> ORGANISM: Human immunodeficiency virus
<220> FEATURE:
<221> NAME/KEY: misc_feature
<223> OTHER INFORMATION: Human immunodeficiency virus frameshift element

<400> SEQUENCE: 6
acctttttta gggaagatct ggccttccta caagggaagg ccagggaatt ttcttacgag 60
ggaccggtaa aaaaacccgt agcactcaag gttaaagcaa agaatctcat tgttaccgaa 120

<210> SEQ ID NO 7
<211> LENGTH: 642
<212> TYPE: DNA
<213> ORGANISM: Foot-and-mouth disease virus
<220> FEATURE:
<221> NAME/KEY: misc_feature
<223> OTHER INFORMATION: Foot-and-mouth disease virus - WT Asia Lebanon 89 3C protease sequence

<400> SEQUENCE: 7
agtggtgccc caccgaccga cttgcaaaag atggtcatga gcaacactaa gcctgttgag 60
ctcatccttg acggtaagac ggtggccatc tgctgcgcca ccggagtgtt tggtactgcc 120
tacctcgtgc ctcgtcacct tttcgcagaa aagtacgaca ggatcatgtt ggacggcagg 180
gccatgacag acagtgacta cagagtgttt gagtttgaga ttaaagtaaa aggacaggac 240
atgctctcag acgctgcgct catggtgctc caccgtggca accgtgtgag agacatcacg 300
aaacactttc gtgatacagc aagaatgaag aaaggtaccc ccgttgtcgg cgtgatcaac 360
aacgccgacg ttgggagact gattttctcc ggtgaggccc tcacctacaa ggacattgta 420
gtgtgcatgg atggagacac catgccgggc ctatttgcct acagagccgc taccaaggct 480
ggctactgtg gaggagccgt tcttgccaag gacggagctg acacatttat cgtcggcact 540
cactccgcag gaggcaatgg agtcgggtac tgctcatgcg tatctaggtc catgctcttg 600
aagatgaagg cacacattga ccccgaacca caccacgagt ag 642

<210> SEQ ID NO 8
<211> LENGTH: 214
<212> TYPE: PRT
<213> ORGANISM: Foot-and-mouth disease virus
<220> FEATURE:
<221> NAME/KEY: MISC_FEATURE
<223> OTHER INFORMATION: Foot-and-mouth disease virus - WT Asia Lebanon
      89 3C protease sequence

<400> SEQUENCE: 8

```
Ser Gly Ala Pro Pro Thr Asp Leu Gln Lys Met Val Met Gly Asn Thr
1               5                   10                  15

Lys Pro Val Glu Leu Ile Leu Asp Gly Lys Thr Val Ala Ile Cys Cys
            20                  25                  30

Ala Thr Gly Val Phe Gly Thr Ala Tyr Leu Val Pro Arg His Leu Phe
        35                  40                  45

Ala Glu Lys Tyr Asp Lys Ile Met Leu Asp Gly Arg Ala Met Thr Asp
    50                  55                  60

Ser Asp Tyr Arg Val Phe Glu Phe Glu Ile Lys Val Lys Gly Gln Asp
65                  70                  75                  80

Met Leu Ser Asp Ala Ala Leu Met Val Leu His Arg Gly Asn Arg Val
                85                  90                  95

Arg Asp Ile Thr Lys His Phe Arg Asp Thr Ala Arg Met Lys Lys Gly
            100                 105                 110

Thr Pro Val Val Gly Val Ile Asn Asn Ala Asp Val Gly Arg Leu Ile
        115                 120                 125

Phe Ser Gly Glu Ala Leu Thr Tyr Lys Asp Ile Val Val Thr Met Asp
    130                 135                 140

Gly Asp Thr Met Pro Gly Leu Phe Ala Tyr Lys Ala Ala Thr Lys Ala
145                 150                 155                 160

Gly Tyr Cys Gly Gly Ala Val Leu Ala Lys Asp Gly Ala Asp Thr Phe
                165                 170                 175

Ile Val Gly Thr His Ser Ala Gly Gly Asn Gly Val Gly Tyr Cys Ser
            180                 185                 190

Cys Val Ser Arg Ser Met Leu Leu Lys Met Lys Ala His Ile Asp Pro
        195                 200                 205

Glu Pro His His Glu Lys
    210
```

<210> SEQ ID NO 9
<211> LENGTH: 642
<212> TYPE: DNA
<213> ORGANISM: Artificial Sequence
<220> FEATURE:
<223> OTHER INFORMATION: FMDV A22 Iraq strain 3C protease with C142T
      mutation

<400> SEQUENCE: 9

```
agtggagccc caccgaccga cttgcaaaag atggtcatgg gcaacaccaa gcctgttgaa    60

ctcatcctcg acgggaagac ggtggccatt tgttgtgcta ccggtgtgtt tggcactgcg   120

tacctcgtgc ctcgtcatct ttttgcagaa aaatatgaca agatcatgct ggacggcaga   180

gccatgacag acagtgacta cagagtgttt gagtttgaga ttaaagtaaa aggacaggac   240

atgctctcag acgctgcgct catggtactc caccgtggga atcgcgtgag agacatcacg   300

aaacactttc gtgacacagc aagaatgaag aaaggcaccc ctgttgtcgg agtaatcaac   360

aatgccgacg tcgggagact gatcttctct ggtgaggccc ttacctacaa ggacattgta   420
```

gtgacaatgg atggagacac catgcctggc ctgtttgcct acaaagccgc caccaaggct 480
ggctactgtg ggggagccgt tcttgctaag gacggagctg acacattcat cgttggcact 540
cactccgcag gcggcaatgg agttggatac tgctcatgcg tttccaggtc catgttgctg 600
aaaatgaagg cgcacatcga ccccgaacca caccacgaga ag 642

<210> SEQ ID NO 10
<211> LENGTH: 214
<212> TYPE: PRT
<213> ORGANISM: Artificial Sequence
<220> FEATURE:
<223> OTHER INFORMATION: FMDV A22 Iraq strain 3C protease with C142T mutation

<400> SEQUENCE: 10

Ser Gly Ala Pro Pro Thr Asp Leu Gln Lys Met Val Met Gly Asn Thr
1 5 10 15

Lys Pro Val Glu Leu Ile Leu Asp Gly Lys Thr Val Ala Ile Cys Cys
20 25 30

Ala Thr Gly Val Phe Gly Thr Ala Tyr Leu Val Pro Arg His Leu Phe
35 40 45

Ala Glu Lys Tyr Asp Lys Ile Met Leu Asp Gly Arg Ala Met Thr Asp
50 55 60

Ser Asp Tyr Arg Val Phe Glu Phe Glu Ile Lys Val Lys Gly Gln Asp
65 70 75 80

Met Leu Ser Asp Ala Ala Leu Met Val Leu His Arg Gly Asn Arg Val
85 90 95

Arg Asp Ile Thr Lys His Phe Arg Asp Thr Ala Arg Met Lys Lys Gly
100 105 110

Thr Pro Val Val Gly Val Ile Asn Asn Ala Asp Val Gly Arg Leu Ile
115 120 125

Phe Ser Gly Glu Ala Leu Thr Tyr Lys Asp Ile Val Val Thr Met Asp
130 135 140

Gly Asp Thr Met Pro Gly Leu Phe Ala Tyr Lys Ala Ala Thr Lys Ala
145 150 155 160

Gly Tyr Cys Gly Gly Ala Val Leu Ala Lys Asp Gly Ala Asp Thr Phe
165 170 175

Ile Val Gly Thr His Ser Ala Gly Gly Asn Gly Val Gly Tyr Cys Ser
180 185 190

Cys Val Ser Arg Ser Met Leu Leu Lys Met Lys Ala His Ile Asp Pro
195 200 205

Glu Pro His His Glu Lys
210

<210> SEQ ID NO 11
<211> LENGTH: 2259
<212> TYPE: DNA
<213> ORGANISM: Foot-and-mouth disease virus
<220> FEATURE:
<221> NAME/KEY: misc_feature
<223> OTHER INFORMATION: Wild-type P1 polyprotein precursor derived from FMDV O1 Manisa isolate 87

<400> SEQUENCE: 11
ggagccgggc aatccagccc ggcaaccggg tcacagaacc aatcaggcaa cactgggagc 60
atcatcaaca attactacat gcagcagtac caaaactcca tggacacaca acttggtgac 120
aacgctacaa gcggaggctc aaacgagggg tccacggaca caacctccac ccacacaacc 180

-continued

```
aacactcaga acaacgactg gttctcgaag ctggccagtt ccgctttcag cggtcttttc    240
ggcgctcttc tcgccgacaa gaaaaccgag gagaccactc ttctagagga ccgcatcctc    300
actactcgta acggacacac cacctcgaca acccagtcga gcgttggagt cacgtacggg    360
tatgcaacag ctgaggattt cgtgagcggg ccaaacacct ctggtctcga gaccagggtt    420
gcccaggcag agcggttctt taaaacccac ctgttcgact gggtcaccag tgacccgttc    480
ggacggtgcc acctgctgga acttccaact gaccacaaag gtgtctacgg cagcctgacc    540
gactcgtatg cttatatgag gaacggctgg gatgttgaag tcactgcagt gggaaaccag    600
ttcaatggag gatgcctgtt ggtggccatg gtgccagaac tttgctccat acagaagagg    660
gagctgtacc agctcacgct ctttcctcac cagttcatca accctcggac gaacatgaca    720
gcacacatca ctgtgccctt tgttggcgtc aaccgttatg accagtacaa ggtacacaaa    780
ccttggaccc tcgtggttat ggttgtagcc cccctgaccg tcaacagtga aggtgccccg    840
caaatcaagg tgtatgccaa catcgcacct accaacgtac acgtcgcggg tgagttccct    900
tccaaagagg ggatcttccc tgtggcttgc agcgatggtt atggcggtct ggtgaccact    960
gacccgaaaa cggctgaccc cgcttacggg aaagtgttta accccccccg caacatgttg   1020
ccggggcggt tcaccaattt tcttgacgtg gctgaggcgt gccccacgtt tctccacttc   1080
gagggtgacg tgccatacgt gaccacgaag acggattcag acagggtgct cgctcagttc   1140
gacttgtctt tggcagcaaa gcacatgtcg aacaccttcc ttgcaggtct cgcccagtac   1200
tacacacagt acagcggcac catcaacctg cacttcatgt tcacagggcc tactgacgcg   1260
aaggcgcgtt acatgattgc gtatgctcct cctggcatgg aaccacctaa aacgccagag   1320
gcggctgccc actgcattca tgctgaatgg gacacagggt tgaactcaaa attcacattt   1380
tcaatccctt acctttcggc ggctgattac gcttacacag cgtctgacac tgctgagacc   1440
acaaatgtac agggatgggt ttgcctgttt caaataacac acgggaaagc tgacggcgac   1500
gcactggtcg ttttggctag cgccggaaag gactttgagc tgcgcctgcc ggtggatgct   1560
cgcacacaga ctacctccgc gggcgagtca gctgaccccg tgaccgccac cgttgagaat   1620
tacggtggcg agacacaggt ccagaggcgc caacacacgg acgtctcatt tatattagac   1680
agatttgtga aagtgacacc aaaagaccaa attaatgtat tggacctgat gcaaacccct   1740
gctcacactt tggtgggagc actccttcgt actgccactt actatttcgc tgacttagag   1800
gtggcagtga agcacgaggg aaacctcacc tgggtcccga acggggcgcc tgaagcggcg   1860
ttggacaaca ccaccaaccc aacagcttac cacaaggcac cactcacccg acttgcactg   1920
ccttacacgg cgccacaccg cgtgttggct actgtttaca acgggaacag caagtatggt   1980
gacggcacgg tggccaatgt gagaggtgac ctgcaagtgt tggcccagaa ggcggcgaga   2040
gcgctgccta cctccttcaa ctacggtgcc attaaagcta ctcgggtgac tgaactgctt   2100
taccgcatga agagggctga gacatactgt ccccggcctc ttttggccat tcacccggac   2160
caggctagac acaagcagaa gattgtggca ccggtgaaac agcttctaaa ttttgacctg   2220
ctcaaattgg cgggagatgt ggagtccaac cctgggccc                           2259
```

<210> SEQ ID NO 12
<211> LENGTH: 2211
<212> TYPE: DNA
<213> ORGANISM: Foot-and-mouth disease virus
<220> FEATURE:
<221> NAME/KEY: misc_feature
<223> OTHER INFORMATION: Wild-type P1 polyprotein precursor derived from FMDV Type A (A/IRN/1/96)

<400> SEQUENCE: 12

```
ggagccggac aatccagtcc ggcaaccggg tcgcaaaacc aatcaggtaa cactggaagc     60
atcatcaaca actactacat gcaacaatac cagaattcca tggacacaca acttggagac    120
aacgccatca gcggaggctc caacgaggga tccacagaca ccacctccac ccacacaacc    180
aacacccaaa acaacgactg gttttcaaaa ttggccagct ctgcctttag cgggctcttc    240
ggtgctcttc ttgctgacaa gaagacagag gaaaccaccc tcctggaaga ccgcatcctc    300
actacccgca acggacatac cacctcaaca acccagtcga gtgtgggagt cacctacggg    360
tattccactg gagaagacca cgtttccggg cccaatacgt ctggcttgga aacscgggtg    420
acacaggcag agagattttt caagaaacac ttgtttaatt ggacaactga caaacctttt    480
gggtacttgg aaaagctgga acttcccact gaccacaagg gtgtttacgg acacctagtg    540
gattcttttg catacatgag aaacggctgg gacgtggagg tgtccgccgt tggcaaccag    600
ttcaacggtg gatgcctcct agtggccatg gtgcctgaat ggaaagagtt cactccacgt    660
gagaagtacc agctcacctt gttcccgcat cagttcatta gccccagaac caacatgact    720
gctcacatca cggtcccgta ccttggtgtg aatagatatg accagtacaa gaagcacaag    780
ccctggacgc tggtcgtgat ggtggtttcg ccgcttacca acagcagcat tggtgccaca    840
gaaatcaagg tctacgccaa catcgcccca acccacgttc acgtagccgg tgagctcccg    900
tcgaaagagg ggatcgtgcc ggttgcttgc tcggatgggt acggcggtct ggtgacaacg    960
gacccgaaaa cagctgaccc tgtctacggt aaggtgtaca acccgcctag gacaaactat   1020
cctgggcgct tcacaaactt gttggacgtg gccgaggctt gcccaacctt cctctgtttc   1080
gacgacggga aaccgtacgt tgtgacaaga gaggatgagc agcgtctact ggccaagttc   1140
gacgtctctc ttgctgcaaa gcacatgtca aacacctacc tatcagggat agcgcagtac   1200
tatgcacagt actctggcac catcaacctc cacttcatgt tcactggttc tactgactca   1260
aaagcccgct acatggtagc gtacgtcccg cccggcgtgg aaacaccgcc ggacacgcct   1320
gagagagctg cacactgcat ccacgctgag tgggacacag ggctgaactc caaattcact   1380
ttttctatcc cgtacgtgtc cgccgcggat tacgcgtaca ccgcgtctga tgtggccgaa   1440
acaacaaacg tacagggatg ggtctgcatc taccagatca cgcacgggaa ggctcaaaac   1500
gacactctgg ttgtgtcgat tagcgccggc aaggactttg agttgcgtct cccgattgac   1560
ccccgcacac agaccacatc tgccggggag tctgcagacc cagtcaccac cactgttgaa   1620
aactacggcg gtgagacaca agtccagcga cgtcaccaca ctgatgtcgg cttcataatg   1680
gacagatttg tgaagattaa caacaccagc cccacacacg tcattgacct catgcaaacc   1740
caccagcacg ggttggtggg cgctctcctg cgtgctgcca cgtactactt ctcagacctg   1800
gagattgtgg tgcgccacga aggcaacctg acgtgggtgc ccaatggagc accagaggca   1860
gccctgagca acgcgggcaa ccccaccgcc tacaacaaag caccattcac gaggctagca   1920
ctcccctaca ctgcgccgca ccgcgtgttg gcgacggtgt acaacgggac gagcaagtac   1980
tcgacaactg gtgggcacac acggggtgac ttgggagctc ttgcggcgag ggtcgccgcc   2040
caactccctg cctctttcaa ctttggcgca atccgggcca ctgacatcag tgagcttctt   2100
gtgcgcatga agcgtgctga gctctactgc cccaggccac tactggcagt ggaagtgaca   2160
gcgcaagaca ggcacaaaca gaagatcatt gcgcctgcga aacagctcct g             2211
```

```
<210> SEQ ID NO 13
<211> LENGTH: 2193
<212> TYPE: DNA
<213> ORGANISM: Foot-and-mouth disease virus
<220> FEATURE:
<221> NAME/KEY: misc_feature
<223> OTHER INFORMATION: Wild-type P1 polyprotein precursor derived from
      FMDV Type C (Haute Loire FR/69)
<220> FEATURE:
<221> NAME/KEY: misc_feature
<222> LOCATION: (1182)..(1183)
<223> OTHER INFORMATION: n is a, c, g, or t
<220> FEATURE:
<221> NAME/KEY: misc_feature
<222> LOCATION: (1455)..(1456)
<223> OTHER INFORMATION: n is a, c, g, or t
<220> FEATURE:
<221> NAME/KEY: misc_feature
<222> LOCATION: (1708)..(1709)
<223> OTHER INFORMATION: n is a, c, g, or t
<220> FEATURE:
<221> NAME/KEY: misc_feature
<222> LOCATION: (1883)..(1885)
<223> OTHER INFORMATION: n is a, c, g, or t

<400> SEQUENCE: 13

ggagctgggc aatccagccc agcgaccggt tcgcagaacc aatccggtaa cactggcagc     60

ataattaaca actactatat gcagcagtac caaaactcca tggacacaca actcggcgac    120

aacgccatca gtggaggctc taatgaaggc tccacggaca caacctctac acacacaact    180

aacacccaga acaacgactg gttttccaaa cttgccagtt cagccttcag cggtcttttc    240

ggcgcccttc tcgctgataa gaaaacggag gaaaccactc tccttgaagg ccgcattctc    300

actacccgta acgggcacac gacctcgaca acccagtcga gcgtcggagt cacattcggg    360

tatgcaactg ctgaagatag cacgtctggg cccaatacat ctggtctaga gacgcgcgtt    420

catcaggcag agaggttttt caaaatggca ctttttgatt gggttccctc acaaaatttt    480

ggacacatgc acaaggttgt tctgccccat gaaccaaaag gtgtttacgg gggtcttgtc    540

aagtcatacg cgtacatgcg caatggctgg gacgtcgagg tgactgctgt tggaaaccag    600

ttcaacggcg gctgcctcct ggtggcgctc gtccccgaga tgggcgacat cagtgacagg    660

gaaaagtacc aactaaccct ttacccccac cagttcatca acccacgcac caacatgacg    720

gcacacatca ctgtgcccta cgtgggtgtc aacaggtatg accagtacaa acagcacagg    780

ccctggaccc tcgtggtcat ggttgtcgca ccactcacca caaacacagc aggtgcccaa    840

cagatcaagg tgtatgccaa catagcccca accaacgtgc acgtagcagg tgagctcccc    900

tccaaggagg ggatcttccc cgttgcgtgt tctgacggtt acggcaacat ggtgacaact    960

gacccgaaaa cggctgaccc tgcctacggg aaagtttaca accccccccg gactgctctg   1020

ccggggcggt tcacaaacta cctggatgtt gccgaggctt gtcccacctt cctgatgttc   1080

gagaacgtac cttacgtctc aacacgaact gacgggcaaa ggctactggc caagttcgac   1140

gtgtcgctgg cagcgaaaca catgtcaaac acctacttgg cnngcttggc ccagtactac   1200

acacagtatg ctgggacaat caacctacac ttcatgttca ctgggccgac cgacgcgaaa   1260

gctcggtaca tggtggcgta cgtgccccct ggcatggacg caccagacaa cccagaagag   1320

gctgcccact gcatacacgc agaatgggac actggtctga actctaagtt cacattttcc   1380

atcccgtaca tctcggccgc tgactacgcg tacaccgcgt cccacgaggc tgaaacaaca   1440

tgtgtacagg ggtgnntctg tgtgtaccaa atcactcacg gcaaggcaga cgcagacgcg   1500

ctcgtcgtct ccgcatcagc ggggaaagac tttgagctcc ggctacctgt ggacgctaga   1560
```

-continued

```
cgacaaacta cggccactgg tgaatctgct gaccccgtca ccactaccgt tgagaactac   1620

ggaggagaga ctcaagtcca acgtcgccac cacaccgacg ttgccttcgt ccttgaccgg   1680

tttgtgaagg tcacagtgtc gggtaacnna cacacactcg acgtgatgca ggcacacaaa   1740

gacaacatcg tgggcgcgct tcttcgcgca gccacgtact acttttctga ttcggaaata   1800

gcagtgaccc acactgggaa gctcacatgg gtgcccaacg gtgcaccagt ttctgcactt   1860

gacaacacaa ccaatcccac tgnnnaccac aagggcccgt tgactcgact ggctctccca   1920

tacaccgcgc cacaccgtgt gttggctacg gcgtacactg gcactacgac ctacaccgcc   1980

agtacacgcg gggatttggt tcacctagcg gcgacgcatg ctcggcactt gccgacatcg   2040

ttcaactttg gtgcagttaa agcagaaaca atcactgagt tgctcgtgcg catgaagcgt   2100

gctgaactct attgtcctag gccgattctt ccgattcagc caacgggtga tagacacaag   2160

caaccgctcg tcgcacctgc aaaacaactg ctg                                2193
```

```
<210> SEQ ID NO 14
<211> LENGTH: 2220
<212> TYPE: DNA
<213> ORGANISM: Foot-and-mouth disease virus
<220> FEATURE:
<221> NAME/KEY: misc_feature
<223> OTHER INFORMATION: Wild-type P1 polyprotein precursor derived from
      FMDV SAT3 ZAM/04/96/3

<400> SEQUENCE: 14

ggagcaggcc agtcctcacc cgccacgggg tcacaaaacc aatctggcaa cactggtagc     60

attattaata actattacat gcaacagtac caaaattcca tggacaccca gcttggcgac    120

aacgccatat caggtggttc aaatgaaggt agcacggaca ccacgtccac gcataccaac    180

aacacccaga acaacgattg gttttcaaaa ttggcacaat cagccatttc agggctcttc    240

ggggctctgt tggctgacaa aaagacagaa gagacaactc ttcttgagga ccgcatcctc    300

accacgcgcc acaataccac cacctcaacc acccagagct cagtgggagt gacctacgga    360

tacgcgtcag cggaccgttt cctcccgggc cccaacacca gtgggcttga gactagggtc    420

gaacaggcgg agaggttctt caaggagaaa cttttcacct ggacggctgc tcaggagtac    480

gcacacgtgc acctgcttga gctcccagtt gaccacaaag gcatctacgg tgccatggtt    540

gacacacacg catacgtgcg caacggttgg gatgtgcagg tctccgcgac cagcacccaa    600

ttcaacggtg gtactctact ggtggccatg gtgccagagc tccactcact tgacaagcgc    660

gacgtgtcac aactcacgct gttcccacac cagttcatca acccacgtac caacacgacg    720

gcacacattg tcgtccccta cgtgggggtt aacagacatg accaggtgaa actccacaaa    780

gcctggacac tggtagtggc tgtcatggca ccactcacaa catcaagcat gggccaggac    840

aacgttgagg tgtacgccaa catcgcacct accaacgtgt ttgttgctgg agagatgcca    900

aacaaacaag gtatcatccc cgtagcctgc aacgatggct atggcggctt ccagaacact    960

gacccgaaga ccgcagaccc catctacggt ctagtgtcca acgcgcctcg cacggccttc   1020

cccggaaggt tcacaaacct tttggacgtg gccgaggcat gtcccacttt cctggatttt   1080

gacggcacac cgtacgttaa gacccggcac aacagtggat ctaaaattct cacgcacatt   1140

gatttggcat ttggacacaa agctttcaag aacacgtacc ttgctgggct agcacaatac   1200

tatgcccagt acagtggttc cctgaacctg catttcatgt acactgggcc cacgcagtca   1260

aaggcccgct tcatggttgt gtacgttcca cctgggacca acccggtccc cgacacacct   1320

gaggcggcgt cgcactgcta ccactcagaa tgggacacag gtctgaactc caagttcacg   1380
```

-continued ttcacagtgc cgtacatttc ggcggccgac tttgcctaca cctactgtga tgaacctgaa 1440
caagcgtctg cacaaggctg ggttacgctc taccaggtga cagacacgca cgaccccgac 1500
tcggcggtgc tgatttcggt cagtgccggg tccgacttgg aattcaggtt gccaatcaac 1560
cccgcaccac agacaaccag tgcaggtgaa ggtgcaaatg tggtcacaac cgatgtcacc 1620
acacatggtg gtgaaacagt gcaccccagg agacagcaca ccaacgtcga gtttctgctt 1680
gacaggttca cacacattgg ggcaatgacc acttctaaga caattagcct ccttgacaca 1740
aaggaacaca cgctggtggg cgcgatcctg cgctcagcaa cgtactactt ttgtgacctg 1800
gaagtggcag tattgggtga cgcggaatgg gtagcttggg tgcccaatgg gtgcccacac 1860
accgaccggg tggaagacaa tccagtcgtt cactcgaaaa acggtgtgac ccgattcgcg 1920
ctgcctttta ctgcgccaca cggtgtcctc tcaaccgtgt acaatggaac atgcaagtac 1980
tcaaagaccc aacgcgtgac tccccgacgc ggcgaccttg ccgtgttgtc cacacgtgtt 2040
gagacggaac aggaacgatg tttgcccaca gcattcaact tcggtcgatt gttgtgtgac 2100
tcgggcgacg tgtactacag gatgaagagg gcggagcttt actgcccgcg ccctctcaga 2160
gtcaggtaca cccacaccac tgacaggtac aaggtcgccc tggttaaacc agagaaacaa 2220

<210> SEQ ID NO 15
<211> LENGTH: 2220
<212> TYPE: DNA
<213> ORGANISM: Foot-and-mouth disease virus
<220> FEATURE:
<221> NAME/KEY: misc_feature
<223> OTHER INFORMATION: Wild-type P1 polyprotein precursor derived from FMDV SAT2 SEN/05/75

<400> SEQUENCE: 15
ggcgcaggac aatcctcacc tgctacgggc tcacaaaacc agtccggcaa cactggcagc 60
atcatcaata actactacat gcaacagtac caaaactcaa tggacactca gttgggcgac 120
aacgccatca gcggtgggtc caacgagggg tcgactgaca ccacgtcgac ccacaccaac 180
aacacccaga acaacgattg gttttccaaa ttggctcaat ccgccatctc gggtcttttc 240
ggggccctcc tggcagacaa gaaaacagag gagaccactc tgctagagga ccgcatactc 300
accacacgac acggcactac tacctcaacc acacagagtt cagtaggtgt cacgtttggg 360
tacgcggacg cggatagttt cacagccggt cctaacactt ctggccttga gactcacgtt 420
ccacaagcag agaggttttt caaagaaaaa ttgtttgatt ggacaagtga caaaccattt 480
ggcacaacgt gcgtgcttga actgcccaaa gatcacaaag gcatctacgg gaagctcaac 540
gactcatacg cgtacatgag gaacggctgg gacgttcagg tcagtgctac cagcacacag 600
ttcaacggag gttccctcct tgtggctatg gtgcctgaac tcagttccat ccgtgacagg 660
gaagagttcc aaccaacact ctacccgcac cagttcataa acccacgcac caacaccacg 720
gcacacatcc aggtcccgta cctgggtgta aaccgccatg accagggcaa acgccaccag 780
gcgtggtctc tggttgtgat ggtgctcacg cctctcacca ctgaggcaca gatgaactct 840
gggaccgttg aggtgtacgc caacattgca cccaccaacg tgtacgtggc gggcgaactc 900
cctgggaaac agggaattgt gcccgtcgcg tgctcagacg gttacggtgg attccagaac 960
acagacccca agacggccga tccgatttac ggacatgtgt acaccccctc gcggcaagac 1020
tgtcacggtc ggttctccaa cctgttggac gtcgctgagg catgccccac actactgaac 1080
ttcgacggga aaccgtacgt tgtgacgaag agcagtgggg acaaggtaat ggccgctttt 1140

-continued gacgtggcct tcacccacaa ggtgcacaag aacacgtttt tggcggggct ggccgactat 1200
tacacccagt acactggcag tctcaactac cacttcatgt acacaggccc cactcaccac 1260
aaagccaaat tcatggtggc atacgtccca ccagggattg cagttgcgca gctgcccaaa 1320
acaccggaag acgcttcaca ctgctaccac tctgaatggg acacgggtct gaactcatct 1380
ttcacgttcg cagttcctta catctcgtct gcggacttct cctacacaca cacagacaca 1440
cccgccatgg ccacaaccaa cggctgggtt gttgtgttgc aagtcacaga cacgcactcg 1500
gcagaagccg cagtcgttgt gtccgtcagt gctgggcctg acctcgagtt caggttccca 1560
atcgaccccg ttcgccagac cacatcggcg ggcgagagcg cggacgtagt gacgaccgac 1620
ccaaccacac acggtggggc agtcacaaac ccgcgacgca aacacactga cgttgctttt 1680
ctcctggaca ggtcaaccca cgttcacact gggaagacca cattcgaggt caacttgatg 1740
gacaccaagg agaaagcctt ggtgggcgcc gttctgcgcg cggccaccta ctatttttgt 1800
gacttggaaa ttgcatgtgt tggtgaccac aaaagggtgt tctggcaacc caacggtgcg 1860
cccagggcga cccagttggg agacaaccca atggtcttct cccacaacaa ggtggcacgg 1920
ttcgcaatcc cgttcaccgc gccacaccgt ctgctctcca ctgtttacaa cggtgagtgt 1980
aactactcca cgtcggtgac gccgatacgt ggtgacaggg cggtcctggc ggccaagtac 2040
gccagcacca agcacacgct cccgtccact ttcaatttcg ggtacgtgac cgccgacgcg 2100
ccagtcgacg tttactaccg aatgaaaagg agcgaactct actgccccag gccactcttg 2160
ccagcgtacg accaccaatc gcacgacagg tttgatgcgc ccattggcgt agagaagcaa 2220

<210> SEQ ID NO 16
<211> LENGTH: 2229
<212> TYPE: DNA
<213> ORGANISM: Artificial Sequence
<220> FEATURE:
<223> OTHER INFORMATION: Wild-type P1 polyprotein precursor derived from FMDV SAT1 NIG/15/75
<220> FEATURE:
<221> NAME/KEY: misc_feature
<223> OTHER INFORMATION: Wild-type P1 polyprotein precursor derived from FMDV SAT1 NIG/15/75

<400> SEQUENCE: 16
ggggccggac aatccagtcc ggcaactgga tcacagaacc agtcaggcaa cacaggtagt 60
atcatcaaca actactatat gcaacagtac caaaactcga tggacacgca gctcggcgac 120
aacgccatca gcggtggctc caatgagggg tcgacagaca ccacgtcgac ccacacaaac 180
aacacccaga acaacgactg gttttcaaag ctggcccggt ccgctttcag cggtttggtc 240
ggcgctctgc tcgcagacaa gaaaaccgag gaaacgactc tccttgagga ccggatcctc 300
accacgtcac acggaactac tacgtctacg acacagagtt ccgtgggagt gacgtatggg 360
tacgcttcgt ccgacaagtt tctaccaggg cccaacacca acgggctgga gactagagtc 420
gaacaggcgg agcgttactt caagcagaag ttgtttgact gggacacaac gcagaagttt 480
ggcacaaccc acatcctggc cctaccaacg gaccataagg gtgtctacgg tcaactgtta 540
gactcataca cttacatgag gaacggttgg gacgtccaag tctcggccac cgccacccag 600
ttcaacggtg gctgtctact agtggctatg gtgcctgagc tttgctcact gagtgaccgg 660
gagaagtacc aactcactct tttcccacac cagttcataa accccagaac caacaccact 720
gcgcacattc aggtgcctta cctgggtgtg gatcgccacg accaggggaa acgccacaag 780
gcatggaccc tggttgtcat ggtggtgtca ccgtacacga atgaccagac aatcgggtca 840

-continued tcaaaggctg aggtgtacgt aaacatcgca ccgaccaacg tgtacgtcgc cggagagaaa 900
ccggccaaac aaggtattgt gccagtcgct gtgtccgacg gatacggcgg cttccaaaac 960
acagacccaa agacatctga cccaatttat ggtcacgttt acaatgctgc acgtaccggt 1020
taccccggga agttcagcaa cctcatggat gttgcggagg cgtgtccaac gtttctcgac 1080
ttcaatggag caccatacgt aaccacacaa gcacattctg ggtcaaaggt catggcatgt 1140
ttcgatttgg ccttcgggca caagaacctt aaaaacacat acctctcagg cttggcacag 1200
tactacacac agtacagcgg tactttgaac ctccacttca tgtactctgg acccaccaac 1260
aacaaggcca agtacatggt tgcgtacata ccaccaggta cgcacccgct gcctgaaaca 1320
cctgaccagg cgtcccactg ttaccacgca gagtgggaca caggtctcaa ctccactttc 1380
acattcacag tgccatacat ttctggtgcg gactttgcct acacccacgc ctacgaacct 1440
gaacaatcca gcgttcaagg ttgggtgggc gtctaccaga tcactgacac ccacgagaaa 1500
gatggtgcac tgatcgtcac ggttagcgcg gggcccgacc tcgagttccg cctaccgata 1560
agccccagcc ggcagacaac aagtgctgga gaaggtgccg acgtcgtcac gaccgacgca 1620
tccgcgcacg gaggtaacac tcgccctaca cggcgggttc acaccgacgt cgcgtttctc 1680
ttggaccgtt ttactctggt tggcaagact gtggacaaca agatggtgtt agacttgctc 1740
aagacaaaag agaaggcact ggtgggcgca gtcttgcgtt ccgccacgta ctacttttca 1800
gacttggagg tagcatgtgt tggcactaac aaatgggtcg gttgggttcc taacggtgcc 1860
cctgtgccta aggaagtggg cgacaaccca gtcgtcttct cccacaacgg caccacccgt 1920
ttcgctctgc cgtacactgc tccacaccgt gtgttggcaa caacctacaa cggtgattgc 1980
aagtacaagg cccagcccgt ggagaacaga gagatccgcg gtgacatggc cgtcttggcc 2040
gctcgcgtcg ctgaggagac tcacatcccg accactttca actacgggat gatcttgacc 2100
gaaagcgaag ttgacgtcta cgtgagaatg aagagggctg agctctactg cccacgcttt 2160
ctgctcacca cgtacgacca caacggagct gacaggtaca agaccacgct ggtagcacca 2220
gagaaacaa 2229

<210> SEQ ID NO 17
<211> LENGTH: 2196
<212> TYPE: DNA
<213> ORGANISM: Foot-and-mouth disease virus
<220> FEATURE:
<221> NAME/KEY: misc_feature
<223> OTHER INFORMATION: Wild-type P1 polyprotein precursor derived from
FMDV Asia 1 IND 63/72

<400> SEQUENCE: 17
ggagccgggc aatccagccc ggcaaccggg tcgcagaacc agtcaggcaa cactggaagc 60
atcattaaca actactacat gcagcaatac cagaattcca tggacacaca acttggtgac 120
aacgctatta gcggaggctc caacgaaggt tccacggaca ccacttccac acacacaaac 180
aacacccaaa acaacgattg gttctcgcgc ctagccagtt cggccttcac cggactgttt 240
ggcgctcttt tggccgacaa gaaaacggaa gagacaaccc tgcttgaaga ccgcatcctc 300
accaccagga acggccacac gacgtcgacg acacagtcaa gcgtcggcgt gacttacggt 360
tacgctgtgg ccgaagacgc tgtttctggg cccaacacct caggcttgga gacccgcgtg 420
acacaggctg aacggttttt caagaaacac ctgtttgatt ggacaccaaa tctatcgttt 480
ggacactgtc actacctgga actcccctcc gaacacaaag gcgtgttcgg cagcctcatg 540
gactcctacg cctacatgag gaacgggtgg gacattgagg tgaccgctgt tggaaaccag 600
ttcaatggtg gttgcctcct cgtcgcactc gtcccggagc tgaaagaact tgacacgcgg 660
cagaagtacc agttgaccct cttcccacac cagttcatca acccacgcac caacatgacg 720
gctcacatca acgtgccgtt cgtgggtgtc aacaggtacg accaatacaa gctccacaag 780
ccgtggacgc ttgttgtgat ggtggtggct ccacttaccg tcaaaaccgg tggttccgaa 840
cagatcaagg tttacatgaa tgcagcacca acccacgtgc atgtggcagg ggaactgccc 900
tcgaaagagg ggatagtacc cgttgcgtgt gcggccggtt atggcaacat ggtgaccaca 960
gacccgaaga cggctgaccc cgtttacggg aaagtgttca accccccccag aacaaatctc 1020 cctgggcgct tcacaaactt ccttgatgta gcggaggcat gcccaacctt cctccgcttc 1080
ggagaagtac catttgtgaa gacggggaac tctggtgacc gcttgcttgc caagtttgac 1140
gtgtcgctcg ctgcggggca catgtccaac acctacttgg caggcttggc gcagtactac 1200
acacagtaca gcggcaccat gaacatccac ttcatgttca ccgggcccac ggatgccaaa 1260
gctcgctaca tggtggctta cgtacctcct ggtatggagc cacccacaga acccgagcgg 1320
gccgcgcact gtatacattc tgagtgggac actggtctta attccaagtt caccttttcc 1380
attccttacc tctctgctgc tgactacgct tacactgctt ctgacgtggc cgagaccacg 1440
agtgtgcagg gatgggtgtg catttatcag attacgcacg gcaaagctga aggcgacgcg 1500
ctggtcgtgt ctgtcagtgc cggcaaggac tttgagtttc gactgccagt ggatgctcgc 1560
cgagagacta ccaccgctgg cgagtccgca gacccagtca ccaccacagt tgagaactac 1620
ggaggagaga ctcagtcggc ccgacggcta cacactgacg ttgcttttgt tctcgacagg 1680
tttgtgaaac tcacccccaa gaacacccag attcttgatc tcatgcagat cccctcacac 1740
acactggttg gagcgttact ccggtccgcg acgtactact tctcggacct ggaggttgcg 1800
cttgttcaca caggctcagt cacatgggtg cccaatggcg cgcccaagga cgccttggac 1860
aaccacacca acccgactgc ctaccagaag aaacccatca cccgcctggc gctcccctac 1920
accgctcccc accgtgtgct ggcaacagtg tacaacggga agacaacgta cgggacacaa 1980
cccacgcggc gtggtgacct tgctgttctt gcacagcggg taagcaacag gctgcccacc 2040
tccttcaact acggtgctgt gaaggctgac accatcacgg agctgttgat ccgcatgacg 2100
cgtgcggaga catactgccc caggcctttg ctagctcttg acaccaccca cgaccgccgt 2160
aagcaggaga tcattgcacc tgagaagcaa gttttg 2196

<210> SEQ ID NO 18
<211> LENGTH: 2925
<212> TYPE: DNA
<213> ORGANISM: Artificial Sequence
<220> FEATURE:
<223> OTHER INFORMATION: O1P1-3C(wt) insert

<400> SEQUENCE: 18
gccgccgcca tgggagccgg gcaatccagc ccggcaaccg ggtcacagaa ccaatcaggc 60
aacactggga gcatcatcaa caattactac atgcagcagt accaaaactc tatggacaca 120
caacttggtg acaacgctac aagcggaggc tcaaacgagg ggtccacgga cacaacctcc 180
acccacacaa ccaacactca gaacaacgac tggttctcga agctggccag ttccgctttc 240
agcggtcttt tcggcgctct tctcgccgac aagaaaaccg aggagaccac tcttcttgag 300
gaccgcatcc tcactactcg taacggacac accacctcga caacccagtc gagcgtagga 360
gtcacatacg ggtatgcaac ggctgaggat ttcgtgagcg ggccaaacac ctctggtctt 420

-continued

```
gagaccaggg ttgcccaggc agagcggttc tttaaaaccc acctgttcga ctgggtcaca    480
agtgacccgt tcggacggtg ccacctgcta gaacttccaa ctgaccacaa aggtgtctat    540
ggcagcctga ccgactcgta tgcttatatg aggaacggct gggatgttga agtcactgct    600
gtgggaaatc agttcaatgg aggatgcctg ttggtggcta tggtgccaga actttgctcc    660
atacagaaga gggagctgta ccagctcacg ctctttcctc accagttcat caaccctcgg    720
acgaacatga cagcacacat cactgtgccc tttgttggcg tcaaccgtta tgaccagtac    780
aaggtacaca aaccttggac cctcgtggtt atggttgtag ccccccctgac cgtcaacagt    840
gaaggtgccc cgcaaatcaa ggtgtatgcc aacatcgcac ctaccaacgt acacgtcgcg    900
ggtgagttcc cttccaaaga ggggatcttc cctgtggctt gcagcgatgg ttatggcggt    960
ctggtgacaa ctgacccgaa aacggctgac cccgcttacg ggaaagtgtt taaccccccc   1020
cgcaacatgt tgccggggcg gttcaccaat ttcttgacg tggctgaggc gtgccccacg   1080
tttctccact tcgagggtga cgtgccatac gtgaccacga agacggattc agacagggtg   1140
ctcgctcagt tcgacttgtc tttggcagca aagcacatgt ccaacacctt ccttgcaggt   1200
ctcgcccagt actacacaca gtacagcggc accatcaacc tgcacttcat gttcacaggg   1260
cctactgacg cgaaggcgcg ttacatgatt gcgtatgctc ctcctggcat ggaaccacct   1320
aaaacgccag aggcggctgc ccactgcatc catgctgaat gggacacagg gttgaactca   1380
aaattcacat tttcaatccc ttacctttcg gcggctgatt acgcttacac agcgtctgac   1440
actgctgaga ccacaaatgt acagggatgg gtttgcctgt ttcaaataac acacgggaaa   1500
gctgacggcg acgcactggt cgttttggcc agcgccggaa aggactttga gctgcgcctg   1560
ccggtggatg ctcgcacaca gactacctca gcgggcgagt cagcagaccc cgtgaccgcc   1620
accgttgaga attacggtgg cgagacacag gtccagaggc gccaacacac ggacgtgtca   1680
tttatattag acagatttgt gaaagtgaca ccaaaagacc aaattaatgt attggacctg   1740
atgcaaaccc ctgctcacac tttggtggga gcactccttc gtactgccac ttactatttc   1800
gctgacttag aggtggcagt gaagcacgag ggaaacctca cctgggtgcc gaacggggcg   1860
cctgaagcgg cgttggacaa caccaccaac ccaacagctt accacaaggc accactcacc   1920
cgacttgcac tgccttacac ggcgccacac cgcgtgttgg ctactgttta caacgggaac   1980
agcaagtatg gtgacggcac ggtggccaat gtgagaggtg atctgcaagt gttggcccag   2040
aaggcggcga gagcgctgcc tacctccttc aactacggtg ccattaaagc tactcgggtg   2100
actgaactgc tttaccgcat gaagagggct gagacatact gtccccggcc tcttttggcc   2160
attcacccgg accaggctag acacaagcag aagattgtgg ctccggtgaa acagcttcta   2220
aattttgacc tgctcaaatt ggcgggagat gtggagtcca accctgggcc cagcggccgc   2280
atgagtggtg ccccaccgac cgacttgcaa aagatggtca tgagcaacac taagcctgtt   2340
gagctcatcc ttgacggtaa gacggtggcc atctgctgcg ccaccggagt gtttggtact   2400
gcctacctcg tgcctcgtca ccttttcgca gaaaagtacg acaggatcat gttggacggc   2460
agggccatga cagacagtga ctacagagtg tttgagtttg agattaaagt aaaaggacag   2520
gacatgctct cagacgctgc gctcatggtg ctccaccgtg gcaaccgtgt gagagacatc   2580
acgaaacact ttcgtgatac agcaagaatg aagaaaggta cccccgttgt cggcgtgatc   2640
aacaacgccg acgttgggag actgattttc tccggtgagg ccctcaccta caaggacatt   2700
gtagtgtgca tggatggaga caccatgccg ggcctatttg cctacagagc cgctaccaag   2760
gctggctact gtggaggagc cgttcttgcc aaggacggag ctgacacatt tatcgtcggc   2820
```

actcactccg caggaggcaa tggagtcggg tactgctcat gcgtatctag gtccatgctc 2880
ttgaagatga aggcacacat tgaccccgaa ccacaccacg agtag 2925

<210> SEQ ID NO 19
<211> LENGTH: 3047
<212> TYPE: DNA
<213> ORGANISM: Artificial Sequence
<220> FEATURE:
<223> OTHER INFORMATION: O1P1-HIV-3C(C142T) insert

<400> SEQUENCE: 19
gccgccgcca tgggagccgg gcaatccagc ccggcaaccg ggtcacagaa ccaatcaggc 60
aacactggga gcatcatcaa caattactac atgcagcagt accaaaactc tatggacaca 120
caacttggtg acaacgctac aagcggaggc tcaaacgagg ggtccacgga cacaacctcc 180
acccacacaa ccaacactca gaacaacgac tggttctcga agctggccag ttccgctttc 240
agcggtcttt tcggcgctct tctcgccgac aagaaaaccg aggagaccac tcttcttgag 300
gaccgcatcc tcactactcg taacggacac accacctcga caacccagtc gagcgtagga 360
gtcacatacg ggtatgcaac ggctgaggat ttcgtgagcg ggccaaacac ctctggtctt 420
gagaccaggg ttgcccaggc agagcggttc tttaaaaccc acctgttcga ctgggtcaca 480
agtgacccgt tcggacggtg ccacctgcta gaacttccaa ctgaccacaa aggtgtctat 540
ggcagcctga ccgactcgta tgcttatatg aggaacggct gggatgttga agtcactgct 600
gtgggaaatc agttcaatgg aggatgcctg ttggtggcta tggtgccaga actttgctcc 660
atacagaaga gggagctgta ccagctcacg ctctttcctc accagttcat caaccctcgg 720
acgaacatga cagcacacat cactgtgccc tttgttggcg tcaaccgtta tgaccagtac 780
aaggtacaca aaccttggac cctcgtggtt atggttgtag cccccctgac cgtcaacagt 840
gaaggtgccc cgcaaatcaa ggtgtatgcc aacatcgcac ctaccaacgt acacgtcgcg 900
ggtgagttcc cttccaaaga ggggatcttc cctgtggctt gcagcgatgg ttatggcggt 960
ctggtgacaa ctgacccgaa aacggctgac cccgcttacg ggaaagtgtt taacccccccc 1020 cgcaacatgt tgccggggcg gttcaccaat ttcttgacg tggctgaggc gtgccccacg 1080
tttctccact tcgagggtga cgtgccatac gtgaccacga agacggattc agacagggtg 1140
ctcgctcagt tcgacttgtc tttggcagca aagcacatgt ccaacacctt ccttgcaggt 1200
ctcgcccagt actacacaca gtacagcggc accatcaacc tgcacttcat gttcacaggg 1260
cctactgacg cgaaggcgcg ttacatgatt gcgtatgctc ctcctggcat ggaaccacct 1320
aaaacgccag aggcggctgc ccactgcatc catgctgaat gggacacagg gttgaactca 1380
aaattcacat tttcaatccc ttacctttcg gcggctgatt acgcttacac agcgtctgac 1440
actgctgaga ccacaaatgt acagggatgg gtttgcctgt ttcaaataac acacgggaaa 1500
gctgacggcg acgcactggt cgttttggcc agcgccggaa aggactttga gctgcgcctg 1560
ccggtggatg ctcgcacaca gactacctca gcgggcgagt cagcagaccc cgtgaccgcc 1620
accgttgaga attacggtgg cgagacacag gtccagaggc gccaacacac ggacgtgtca 1680
tttatattag acagatttgt gaaagtgaca ccaaaagacc aaattaatgt attggacctg 1740
atgcaaaccc ctgctcacac tttggtggga gcactccttc gtactgccac ttactatttc 1800
gctgacttag aggtggcagt gaagcacgag ggaaacctca cctgggtgcc gaacggggcg 1860
cctgaagcgg cgttggacaa caccaccaac ccaacagctt accacaaggc accactcacc 1920

-continued cgacttgcac tgccttacac ggcgccacac cgcgtgttgg ctactgttta caacgggaac 1980
agcaagtatg gtgacggcac ggtggccaat gtgagaggtg atctgcaagt gttggcccag 2040
aaggcggcga gagcgctgcc tacctccttc aactacggtg ccattaaagc tactcgggtg 2100
actgaactgc tttaccgcat gaagagggct gagacatact gtccccggcc tcttttggcc 2160
attcacccgg accaggctag acacaagcag aagattgtgg ctccggtgaa acagcttcta 2220
aattttgacc tgctcaaatt ggcgggagat gtggagtcca accctgggcc cagcggccgc 2280
ggaccttttt tagggaagat ctggccttcc tacaagggaa ggccagggaa ttttcttacg 2340
agggaccggt aaaaaaaccc gtagcactca aggttaaagc aaagaatctc attgttaccg 2400
aaagtggagc cccaccgacc gacttgcaaa agatggtcat gggcaacacc aagcctgttg 2460
aactcatcct cgacgggaag acggtggcca tttgttgtgc taccggtgtg tttggcactg 2520
cgtacctcgt gcctcgtcat ctttttgcag aaaaatatga caagatcatg ctggacggca 2580
gagccatgac agacagtgac tacagagtgt ttgagtttga gattaaagta aaaggacagg 2640
acatgctctc agacgctgcg ctcatggtac tccaccgtgg gaatcgcgtg agagacatca 2700
cgaaacactt tcgtgacaca gcaagaatga agaaaggcac ccctgttgtc ggagtaatca 2760
acaatgccga cgtcgggaga ctgatcttct ctggtgaggc ccttacctac aaggacattg 2820
tagtgacaat ggatggagac accatgcctg gcctgtttgc ctacaaagcc gccaccaagg 2880
ctggctactg tgggggagcc gttcttgcta aggacggagc tgacacattc atcgttggca 2940
ctcactccgc aggcggcaat ggagttggat actgctcatg cgtttccagg tccatgttgc 3000
tgaaaatgaa ggcgcacatc gaccccgaac cacaccacga gaagtaa 3047

<210> SEQ ID NO 20
<211> LENGTH: 558
<212> TYPE: DNA
<213> ORGANISM: Artificial Sequence
<220> FEATURE:
<223> OTHER INFORMATION: SGLuc insert

<400> SEQUENCE: 20
atgggagtca aagttctgtt tgccctgatc tgcatcgctg tggccgaggc caagcccacc 60
gagaacaacg aagacttcaa catcgtggcc gtggccagca acttcgcgac cacggatctc 120
gatgctgacc gcgggaagtt gcccggcaag aagctgccgc tggaggtgct caaagagatg 180
gaagccaatg cccggaaagc tggctgcacc aggggctgtc tgatctgcct gtcccacatc 240
aagtgcacgc ccaagatgaa gaagtggctc ccaggacgct gccacaccta cgaaggcgac 300
aaagagtccg cacagggcgg cataggcgag gcgatcgtcg acattcctga gattcctggg 360
ttcaaggact tggagcccat ggagcagttc atcgcacagg tcgatctgtg tgtggactgc 420
acaactggct gcctcaaagg gcttgccaac gtgcagtgtt ctgacctgct caagaagtgg 480
ctgccgcaac gctgtgcgac ctttgccagc aagatccagg gccaggtgga caagatcaag 540
ggggccggtg gtgactaa 558

<210> SEQ ID NO 21
<211> LENGTH: 22
<212> TYPE: DNA
<213> ORGANISM: Artificial Sequence
<220> FEATURE:
<223> OTHER INFORMATION: Synthetic primer - O1MSeq1-F

<400> SEQUENCE: 21
gagcatcatc aacaattact ac 22

<210> SEQ ID NO 22
<211> LENGTH: 22
<212> TYPE: DNA
<213> ORGANISM: Artificial Sequence
<220> FEATURE:
<223> OTHER INFORMATION: Synthetic primer - O1MSeq2-F

<400> SEQUENCE: 22
ggaccgcatc ctcactactc gt 22

<210> SEQ ID NO 23
<211> LENGTH: 22
<212> TYPE: DNA
<213> ORGANISM: Artificial Sequence
<220> FEATURE:
<223> OTHER INFORMATION: Synthetic primer - O1MSeq3-F

<400> SEQUENCE: 23
gccacctgct agaacttcca ac 22

<210> SEQ ID NO 24
<211> LENGTH: 22
<212> TYPE: DNA
<213> ORGANISM: Artificial Sequence
<220> FEATURE:
<223> OTHER INFORMATION: Synthetic primer - O1MSeq4-F

<400> SEQUENCE: 24
aggtacacaa accttggacc ct 22

<210> SEQ ID NO 25
<211> LENGTH: 22
<212> TYPE: DNA
<213> ORGANISM: Artificial Sequence
<220> FEATURE:
<223> OTHER INFORMATION: Synthetic primer - O1MSeq5-F

<400> SEQUENCE: 25
aacggctgac cccgcttacg gg 22

<210> SEQ ID NO 26
<211> LENGTH: 22
<212> TYPE: DNA
<213> ORGANISM: Artificial Sequence
<220> FEATURE:
<223> OTHER INFORMATION: Synthetic primer - O1MSeq6-F

<400> SEQUENCE: 26
gcttacacag cgtctgacac tg 22

<210> SEQ ID NO 27
<211> LENGTH: 22
<212> TYPE: DNA
<213> ORGANISM: Artificial Sequence
<220> FEATURE:
<223> OTHER INFORMATION: Synthetic primer - O1MSeq7-F

<400> SEQUENCE: 27
aaacctcacc tgggtgccga ac 22

<210> SEQ ID NO 28
<211> LENGTH: 22
<212> TYPE: DNA
<213> ORGANISM: Artificial Sequence
<220> FEATURE:

-continued

<223> OTHER INFORMATION: Synthetic primer - O1MSeq8-F

<400> SEQUENCE: 28
agatgtggag tccaaccctg gg 22

<210> SEQ ID NO 29
<211> LENGTH: 21
<212> TYPE: DNA
<213> ORGANISM: Artificial Sequence
<220> FEATURE:
<223> OTHER INFORMATION: Synthetic primer - O1P1-Seq-R1

<400> SEQUENCE: 29
gtccgtggac ccctcgtttg a 21

<210> SEQ ID NO 30
<211> LENGTH: 22
<212> TYPE: DNA
<213> ORGANISM: Artificial Sequence
<220> FEATURE:
<223> OTHER INFORMATION: Synthetic primer - O1P1-Seq-R2

<400> SEQUENCE: 30
tcgaggtggt gtgtccgtta cg 22

<210> SEQ ID NO 31
<211> LENGTH: 8825
<212> TYPE: DNA
<213> ORGANISM: Artificial Sequence
<220> FEATURE:
<223> OTHER INFORMATION: pMC-CMV-SV40-polyA O1P1-HIV-3C(C142T) (with
bacterial backbone)

<400> SEQUENCE: 31
acattaccct gttatcccta gatacattac cctgttatcc cagatgacat accctgttat 60
ccctagatga cattaccctg ttatcccaga tgacattacc ctgttatccc tagatacatt 120
accctgttat cccagatgac ataccctgtt atccctagat gacattaccc tgttatccca 180
gatgacatta ccctgttatc cctagataca ttaccctgtt atcccagatg acataccctg 240
ttatccctag atgacattac cctgttatcc cagatgacat taccctgtta tccctagata 300
cattaccctg ttatcccaga tgacataccc tgttatccct agatgacatt accctgttat 360
cccagatgac attaccctgt tatccctaga tacattaccc tgttatccca gatgacatac 420
cctgttatcc ctagatgaca ttaccctgtt atcccagatg acattaccct gttatcccta 480
gatacattac cctgttatcc cagatgacat accctgttat ccctagatga cattaccctg 540
ttatcccaga tgacattacc ctgttatccc tagatacatt accctgttat cccagatgac 600
ataccctgtt atccctagat gacattaccc tgttatccca gatgacatta ccctgttatc 660
cctagataca ttaccctgtt atcccagatg acataccctg ttatccctag atgacattac 720
cctgttatcc cagataaact caatgatgat gatgatgatg gtcgagactc agcggccgcg 780
gtgccagggc gtgcccttgg gctccccggg cgcgactagt gaattgatac tagtattatg 840
cccagtacat gaccttatgg gactttccta cttggcagta catctacgta ttagtcatcg 900
ctattaccat ggtgatgcgg ttttggcagt acatcaatgg gcgtggatag cggtttgact 960
cacggggatt tccaagtctc caccccattg acgtcaatgg gagtttgttt tggcaccaaa 1020
atcaacggga ctttccaaaa tgtcgtaaca actccgcccc attgacgcaa atgggcggta 1080
ggcgtgtacg gtgggaggtt tatataagca gagctcgttt agtgaaccgt cagatcgcct 1140

-continued

```
ggagacgcca tccacgctgt tttgacctcc atagaagatt ctagagtcga cgcggccgcg   1200
gatccgccgc cgccatggga gccgggcaat ccagcccggc aaccgggtca cagaaccaat   1260
caggcaacac tgggagcatc atcaacaatt actacatgca gcagtaccaa aactctatgg   1320
acacacaact tggtgacaac gctacaagcg gaggctcaaa cgaggggtcc acggacacaa   1380
cctccaccca cacaaccaac actcagaaca acgactggtt ctcgaagctg gccagttccg   1440
ctttcagcgg tcttttcggc gctcttctcg ccgacaagaa aaccgaggag accactcttc   1500
ttgaggaccg catcctcact actcgtaacg gacacaccac ctcgacaacc cagtcgagcg   1560
taggagtcac atacgggtat gcaacggctg aggatttcgt gagcgggcca aacacctctg   1620
gtcttgagac cagggttgcc caggcagagc ggttctttaa aacccacctg ttcgactggg   1680
tcacaagtga cccgttcgga cggtgccacc tgctagaact tccaactgac cacaaaggtg   1740
tctatggcag cctgaccgac tcgtatgctt atatgaggaa cggctgggat gttgaagtca   1800
ctgctgtggg aaatcagttc aatggaggat gcctgttggt ggctatggtg ccagaacttt   1860
gctccataca gaagagggag ctgtaccagc tcacgctctt tcctcaccag ttcatcaacc   1920
ctcggacgaa catgacagca cacatcactg tgccctttgt tggcgtcaac cgttatgacc   1980
agtacaaggt acacaaacct tggaccctcg tggttatggt tgtagccccc ctgaccgtca   2040
acagtgaagg tgccccgcaa atcaaggtgt atgccaacat cgcacctacc aacgtacacg   2100
tcgcgggtga gttcccttcc aaagagggga tcttccctgt ggcttgcagc gatggttatg   2160
gcggtctggt gacaactgac ccgaaaacgg ctgaccccgc ttacgggaaa gtgtttaacc   2220
ccccccgcaa catgttgccg gggcggttca ccaattttct tgacgtggct gaggcgtgcc   2280
ccacgtttct ccacttcgag ggtgacgtgc catacgtgac cacgaagacg gattcagaca   2340
gggtgctcgc tcagttcgac ttgtctttgg cagcaaagca catgtccaac accttccttg   2400
caggtctcgc ccagtactac acacagtaca gcggcaccat caacctgcac ttcatgttca   2460
cagggcctac tgacgcgaag gcgcgttaca tgattgcgta tgctcctcct ggcatggaac   2520
cacctaaaac gccagaggcg gctgcccact gcatccatgc tgaatgggac acagggttga   2580
actcaaaatt cacattttca atcccttacc tttcggcggc tgattacgct tacacagcgt   2640
ctgacactgc tgagaccaca aatgtacagg gatgggtttg cctgtttcaa ataacacacg   2700
ggaaagctga cggcgacgca ctggtcgttt tggccagcgc cggaaaggac tttgagctgc   2760
gcctgccggt ggatgctcgc acacagacta cctcagcggg cgagtcagca gaccccgtga   2820
ccgccaccgt tgagaattac ggtggcgaga cacaggtcca gaggcgccaa cacacggacg   2880
tgtcatttat attagacaga tttgtgaaag tgacaccaaa agaccaaatt aatgtattgg   2940
acctgatgca aacccctgct cacactttgg tgggagcact ccttcgtact gccacttact   3000
atttcgctga cttagaggtg gcagtgaagc acgagggaaa cctcacctgg gtgccgaacg   3060
gggcgcctga agcggcgttg gacaacacca ccaacccaac agcttaccac aaggcaccac   3120
tcacccgact tgcactgcct tacacggcgc cacaccgcgt gttggctact gtttacaacg   3180
ggaacagcaa gtatggtgac ggcacggtgg ccaatgtgag aggtgatctg caagtgttgg   3240
cccagaaggc ggcgagagcg ctgcctacct ccttcaacta cggtgccatt aaagctactc   3300
gggtgactga actgctttac cgcatgaaga gggctgagac atactgtccc cggcctcttt   3360
tggccattca cccggaccag gctagacaca agcagaagat tgtggctccg gtgaaacagc   3420
ttctaaattt tgacctgctc aaattggcgg gagatgtgga gtccaaccct gggcccagcg   3480
gccgcggacc ttttttaggg aagatctggc cttcctacaa gggaaggcca gggaattttc   3540
```

```
ttacgaggga ccggtaaaaa aacccgtagc actcaaggtt aaagcaaaga atctcattgt   3600
taccgaaagt ggagccccac cgaccgactt gcaaaagatg gtcatgggca acaccaagcc   3660
tgttgaactc atcctcgacg ggaagacggt ggccatttgt tgtgctaccg gtgtgtttgg   3720
cactgcgtac ctcgtgcctc gtcatctttt tgcagaaaaa tatgacaaga tcatgctgga   3780
cggcagagcc atgacagaca gtgactacag agtgtttgag tttgagatta aagtaaaagg   3840
acaggacatg ctctcagacg ctgcgctcat ggtactccac cgtgggaatc gcgtgagaga   3900
catcacgaaa cactttcgtg acacagcaag aatgaagaaa ggcacccctg ttgtcggagt   3960
aatcaacaat gccgacgtcg ggagactgat cttctctggt gaggccctta cctacaagga   4020
cattgtagtg acaatggatg gagacaccat gcctggcctg tttgcctaca aagccgccac   4080
caaggctggc tactgtgggg gagccgttct tgctaaggac ggagctgaca cattcatcgt   4140
tggcactcac tccgcaggcg gcaatggagt tggatactgc tcatgcgttt ccaggtccat   4200
gttgctgaaa atgaaggcgc acatcgaccc cgaaccacac cacgagaagt aagaattcgc   4260
tagctcgaca atcaacctct ggattacaaa atttgtgaaa gattgactgg tattcttaac   4320
tatgttgctc cttttacgct atgtggatac gctgctttaa tgcctttgta tcatgctatt   4380
gcttcccgta tggctttcat tttctcctcc ttgtataaat cctggttgct gtctctttat   4440
gaggagttgt ggcccgttgt caggcaacgt ggcgtggtgt gcactgtgtt tgctgacgca   4500
acccccactg gttggggcat tgccaccacc tgtcagctcc tttccgggac tttcgctttc   4560
cccctcccta ttgccacggc ggaactcatc gccgcctgcc ttgcccgctg ctggacaggg   4620
gctcggctgt tgggcactga caattccgtg gtgttgtcgg ggaaatcatc gtcctttcct   4680
tggctgctcg cctgtgttgc cacctggatt ctgcgcggga cgtccttctg ctacgtccct   4740
tcggccctca atccagcgga ccttccttcc cgcggcctgc tgccggctct gcggcctctt   4800
ccgcgtcttc gccttcgccc tcagacgagt cggatctccc tttgggccgc ctccccgcct   4860
ggtaccttta agaccaatga cttacaaggc agctgtagat cttagccact ttttaaaaga   4920
aaagggggga ctggaagggc taattcactc ccaacgaaga taagatctgc tttttgcttg   4980
tactgggtct ctctggttag accagatctg agcctgggag ctctctggct aactagggaa   5040
cccactgctt aagcctcaat aaagcttgcc ttgagtgctt caagtagtgt gtgcccgtct   5100
gttgtgtgac tctggtaact agagatccct cagacccttt tagtcagtgt ggaaaatctc   5160
tagcagtagt agttcatgtc atcttattat tcagtattta taacttgcaa agaaatgaat   5220
atcagagagt gagaggaact tgtttattgc agcttataat ggttacaaat aaagcaatag   5280
catcacaaat ttcacaaata aagcattttt ttcactgcat tctagttgtg gtttgtccaa   5340
actcatcaat gtatcttatc atgtctggct ctagctatcc cgcccctaac tccgcccatc   5400
ccgcccctaa ctccgcccag ttccgcccat tctccgcccc atggctgact aattttttt    5460
atttatgcag aggccgaggc cgcctcggcc tctgagctat tccagaagta gtgaggaggc   5520
ttttttggag gcctagactt ttgcagatcg acccatgggg gcccgcccca actggggtaa   5580
cctttgagtt ctctcagttg gggtaatca gcatcatgat gtggtaccac atcatgatgc    5640
tgattataag aatgcggccg ccacactcta gtggatctcg agttaataat tcagaagaac   5700
tcgtcaagaa ggcgatagaa ggcgatgcgc tgcgaatcgg gagcggcgat accgtaaagc   5760
acgaggaagc ggtcagccca ttcgccgcca agctcttcag caatatcacg ggtagccaac   5820
gctatgtcct gatagcggtc cgccacaccc agccggccac agtcgatgaa tccagaaaag   5880
```

-continued

```
cggccatttt ccaccatgat attcggcaag caggcatcgc catgggtcac gacgagatcc   5940
tcgccgtcgg gcatgctcgc cttgagcctg gcgaacagtt cggctggcgc gagcccctga   6000
tgctcttcgt ccagatcatc ctgatcgaca agaccggctt ccatccgagt acgtgctcgc   6060
tcgatgcgat gtttcgcttg gtggtcgaat gggcaggtag ccggatcaag cgtatgcagc   6120
cgccgcattg catcagccat gatggatact ttctcggcag gagcaaggtg agatgacagg   6180
agatcctgcc ccggcacttc gcccaatagc agccagtccc ttcccgcttc agtgacaacg   6240
tcgagcacag ctgcgcaagg aacgcccgtc gtggccagcc acgatagccg cgctgcctcg   6300
tcttgcagtt cattcagggc accggacagg tcggtcttga caaaaagaac cgggcgcccc   6360
tgcgctgaca gccggaacac ggcggcatca gagcagccga ttgtctgttg tgcccagtca   6420
tagccgaata gcctctccac ccaagcggcc ggagaacctg cgtgcaatcc atcttgttca   6480
atcatgcgaa acgatcctca tcctgtctct tgatcagagc ttgatcccct gcgccatcag   6540
atccttggcg gcgagaaagc catccagttt actttgcagg gcttcccaac cttaccagag   6600
ggcgccccag ctggcaattc cggttcgctt gctgtccata aaaccgccca gtctagctat   6660
cgccatgtaa gcccactgca agctacctgc tttctctttg cgcttgcgtt ttcccttgtc   6720
cagatagccc agtagctgac attcatccgg ggtcagcacc gtttctgcgg actggctttc   6780
tacgtgctcg aggggggcca aacggtctcc agcttggctg ttttggcgga tgagagaaga   6840
ttttcagcct gatacagatt aaatcagaac gcagaagcgg tctgataaaa cagaatttgc   6900
ctggcggcag tagcgcggtg gtcccacctg accccatgcc gaactcagaa gtgaaacgcc   6960
gtagcgccga tggtagtgtg gggtctcccc atgcgagagt agggaactgc caggcatcaa   7020
ataaaacgaa aggctcagtc gaaagactgg gcctttcgtt ttatctgttg tttgtcggtg   7080
aacgctctcc tgagtaggac aaatccgccg ggagcggatt tgaacgttgc gaagcaacgg   7140
cccggagggt ggcgggcagg acgcccgcca taaactgcca ggcatcaaat taagcagaag   7200
gccatcctga cggatggcct ttttgcgttt ctacaaactc ttttgtttat ttttctaaat   7260
acattcaaat atgtatccgc tcatgaccaa aatcccttaa cgtgagtttt cgttccactg   7320
agcgtcagac cccgtagaaa agatcaaagg atcttcttga gatccttttt ttctgcgcgt   7380
aatctgctgc ttgcaaacaa aaaaaccacc gctaccagcg gtggtttgtt tgccggatca   7440
agagctacca actctttttc cgaaggtaac tggcttcagc agagcgcaga taccaaatac   7500
tgtccttcta gtgtagccgt agttaggcca ccacttcaag aactctgtag caccgcctac   7560
atacctcgct ctgctaatcc tgttaccagt ggctgctgcc agtggcgata agtcgtgtct   7620
taccgggttg gactcaagac gatagttacc ggataaggcg cagcggtcgg gctgaacggg   7680
gggttcgtgc acacagccca gcttggagcg aacgacctac accgaactga gatacctaca   7740
gcgtgagcta tgagaaagcg ccacgcttcc cgaagggaga aaggcggaca ggtatccggt   7800
aagcggcagg gtcggaacag gagagcgcac gagggagctt ccagggggaa acgcctggta   7860
tctttatagt cctgtcgggt ttcgccacct ctgacttgag cgtcgatttt tgtgatgctc   7920
gtcagggggg cggagcctat ggaaaaacgc cagcaacgcg gcctttttac ggttcctggc   7980
cttttgctgg ccttttgctc acatgttctt tcctgcgtta tcccctgatt ctgtggataa   8040
ccgtattacc gcctttgagt gagctgatac cgctcgccgc agccgaacga ccgagcgcag   8100
cgagtcagtg agcgaggaag cggaagagcg cctgatgcgg tattttctcc ttacgcatct   8160
gtgcggtatt tcacaccgca tatggtgcac tctcagtaca atctgctctg atgccgcata   8220
gttaagccag tatacactcc gctatcgcta cgtgactggg tcatggctgc gccccgacac   8280
```

ccgccaacac ccgctgacgc gccctgacgg gcttgtctgc tcccggcatc cgcttacaga 8340
caagctgtga ccgtctccgg gagctgcatg tgtcagaggt tttcaccgtc atcaccgaaa 8400
cgcgcgaggc agcagatcaa ttcgcgcgcg aaggcgaagc ggcatgcata atgtgcctgt 8460
caaatggacg aagcagggat tctgcaaacc ctatgctact ccgtcaagcc gtcaattgtc 8520
tgattcgtta ccaattatga caacttgacg gctacatcat tcactttttc ttcacaaccg 8580
gcacggaact cgctcgggct ggccccggtg catttttttaa atacccgcga gaaatagagt 8640
tgatcgtcaa aaccaacatt gcgaccgacg gtggcgatag gcatccgggt ggtgctcaaa 8700
agcagcttcg cctggctgat acgttggtcc tcgcgccagc ttaagacgct aatccctaac 8760
tgctggcgga aaagatgtga cagacgcgac ggcgacaagc aaacatgctg tgcgacgctg 8820
gcgat 8825

<210> SEQ ID NO 32
<211> LENGTH: 28
<212> TYPE: DNA
<213> ORGANISM: Artificial Sequence
<220> FEATURE:
<223> OTHER INFORMATION: Synthetic primer - NotI-3cLeb89-F

<400> SEQUENCE: 32
cagcggccgc atgagtggtg ccccaccg 28

<210> SEQ ID NO 33
<211> LENGTH: 23
<212> TYPE: DNA
<213> ORGANISM: Artificial Sequence
<220> FEATURE:
<223> OTHER INFORMATION: Synthetic primer - 3CLeb89-EcoRI-R

<400> SEQUENCE: 33
gaattcctac tcgtggtgtg gtt 23

<210> SEQ ID NO 34
<211> LENGTH: 8703
<212> TYPE: DNA
<213> ORGANISM: Artificial Sequence
<220> FEATURE:
<223> OTHER INFORMATION: pMC-CMV-SV40-polyA O1P1-3C(wt) (with bacterial backbone)

<400> SEQUENCE: 34
acattaccct gttatcccta gatacattac cctgttatcc cagatgacat accctgttat 60
ccctagatga cattaccctg ttatcccaga tgacattacc ctgttatccc tagatacatt 120
accctgttat cccagatgac ataccctgtt atccctagat gacattaccc tgttatccca 180
gatgacatta ccctgttatc cctagataca ttaccctgtt atcccagatg acataccctg 240
ttatccctag atgacattac cctgttatcc cagatgacat taccctgtta tccctagata 300
cattaccctg ttatcccaga tgacataccc tgttatccct agatgacatt accctgttat 360
cccagatgac attaccctgt tatccctaga tacattaccc tgttatccca gatgacatac 420
cctgttatcc ctagatgaca ttaccctgtt atcccagatg acattaccct gttatcccta 480
gatacattac cctgttatcc cagatgacat accctgttat ccctagatga cattaccctg 540
ttatcccaga tgacattacc ctgttatccc tagatacatt accctgttat cccagatgac 600
ataccctgtt atccctagat gacattaccc tgttatccca gatgacatta ccctgttatc 660
cctagataca ttaccctgtt atcccagatg acataccctg ttatccctag atgacattac 720

```
cctgttatcc cagataaact caatgatgat gatgatgatg gtcgagactc agcggccgcg    780
gtgccagggc gtgcccttgg gctccccggg cgcgactagt gaattgatac tagtattatg    840
cccagtacat gaccttatgg gactttccta cttggcagta catctacgta ttagtcatcg    900
ctattaccat ggtgatgcgg ttttggcagt acatcaatgg gcgtggatag cggtttgact    960
cacggggatt tccaagtctc caccccattg acgtcaatgg gagtttgttt tggcaccaaa   1020
atcaacggga ctttccaaaa tgtcgtaaca actccgcccc attgacgcaa atgggcggta   1080
ggcgtgtacg gtgggaggtt tatataagca gagctcgttt agtgaaccgt cagatcgcct   1140
ggagacgcca tccacgctgt tttgacctcc atagaagatt ctagagtcga cgcggccgcg   1200
gatccgccgc cgccatggga gccgggcaat ccagcccggc aaccgggtca cagaaccaat   1260
caggcaacac tgggagcatc atcaacaatt actacatgca gcagtaccaa aactctatgg   1320
acacacaact tggtgacaac gctacaagcg gaggctcaaa cgaggggtcc acggacacaa   1380
cctccaccca cacaaccaac actcagaaca acgactggtt ctcgaagctg gccagttccg   1440
ctttcagcgg tcttttcggc gctcttctcg ccgacaagaa aaccgaggag accactcttc   1500
ttgaggaccg catcctcact actcgtaacg gacacaccac ctcgacaacc cagtcgagcg   1560
taggagtcac atacgggtat gcaacggctg aggatttcgt gagcgggcca aacacctctg   1620
gtcttgagac cagggttgcc caggcagagc ggttctttaa aacccacctg ttcgactggg   1680
tcacaagtga cccgttcgga cggtgccacc tgctagaact tccaactgac cacaaaggtg   1740
tctatggcag cctgaccgac tcgtatgctt atatgaggaa cggctgggat gttgaagtca   1800
ctgctgtggg aaatcagttc aatggaggat gcctgttggt ggctatggtg ccagaacttt   1860
gctccataca gaagagggag ctgtaccagc tcacgctctt tcctcaccag ttcatcaacc   1920
ctcggacgaa catgacagca cacatcactg tgccctttgt tggcgtcaac cgttatgacc   1980
agtacaaggt acacaaacct tggaccctcg tggttatggt tgtagccccc ctgaccgtca   2040
acagtgaagg tgccccgcaa atcaaggtgt atgccaacat cgcacctacc aacgtacacg   2100
tcgcgggtga gttcccttcc aaagagggga tcttccctgt ggcttgcagc gatggttatg   2160
gcggtctggt gacaactgac ccgaaaacgg ctgaccccgc ttacgggaaa gtgtttaacc   2220
ccccccgcaa catgttgccg gggcggttca ccaattttct tgacgtggct gaggcgtgcc   2280
ccacgtttct ccacttcgag ggtgacgtgc catacgtgac cacgaagacg gattcagaca   2340
gggtgctcgc tcagttcgac ttgtctttgg cagcaaagca catgtccaac accttccttg   2400
caggtctcgc ccagtactac acacagtaca gcggcaccat caacctgcac ttcatgttca   2460
cagggcctac tgacgcgaag gcgcgttaca tgattgcgta tgctcctcct ggcatggaac   2520
cacctaaaac gccagaggcg gctgcccact gcatccatgc tgaatgggac acagggttga   2580
actcaaaatt cacattttca atcccttacc tttcggcggc tgattacgct tacacagcgt   2640
ctgacactgc tgagaccaca aatgtacagg gatgggtttg cctgtttcaa ataacacacg   2700
ggaaagctga cggcgacgca ctggtcgttt tggccagcgc cggaaaggac tttgagctgc   2760
gcctgccggt ggatgctcgc acacagacta cctcagcggg cgagtcagca gaccccgtga   2820
ccgccaccgt tgagaattac ggtggcgaga cacaggtcca gaggcgccaa cacacggacg   2880
tgtcatttat attagacaga tttgtgaaag tgacaccaaa agaccaaatt aatgtattgg   2940
acctgatgca aacccctgct cacactttgg tgggagcact ccttcgtact gccacttact   3000
atttcgctga cttagaggtg gcagtgaagc acgagggaaa cctcacctgg gtgccgaacg   3060
```

-continued

```
gggcgcctga agcggcgttg gacaacacca ccaacccaac agcttaccac aaggcaccac   3120
tcacccgact tgcactgcct tacacggcgc cacaccgcgt gttggctact gtttacaacg   3180
ggaacagcaa gtatggtgac ggcacggtgg ccaatgtgag aggtgatctg caagtgttgg   3240
cccagaaggc ggcgagagcg ctgcctacct ccttcaacta cggtgccatt aaagctactc   3300
gggtgactga actgctttac cgcatgaaga gggctgagac atactgtccc cggcctcttt   3360
tggccattca cccggaccag gctagacaca agcagaagat tgtggctccg gtgaaacagc   3420
ttctaaattt tgacctgctc aaattggcgg gagatgtgga gtccaaccct gggcccagcg   3480
gccgcatgag tggtgcccca ccgaccgact tgcaaaagat ggtcatgagc aacactaagc   3540
ctgttgagct catccttgac ggtaagacgg tggccatctg ctgcgccacc ggagtgtttg   3600
gtactgccta cctcgtgcct cgtcaccttt tcgcagaaaa gtacgacagg atcatgttgg   3660
acggcagggc catgacagac agtgactaca gagtgtttga gtttgagatt aaagtaaaag   3720
gacaggacat gctctcagac gctgcgctca tggtgctcca ccgtggcaac cgtgtgagag   3780
acatcacgaa acactttcgt gatacagcaa gaatgaagaa aggtaccccc gttgtcggcg   3840
tgatcaacaa cgccgacgtt gggagactga ttttctccgg tgaggccctc acctacaagg   3900
acattgtagt gtgcatggat ggagacacca tgccgggcct atttgcctac agagccgcta   3960
ccaaggctgg ctactgtgga ggagccgttc ttgccaagga cggagctgac acatttatcg   4020
tcggcactca ctccgcagga ggcaatggag tcgggtactg ctcatgcgta tctaggtcca   4080
tgctcttgaa gatgaaggca cacattgacc ccgaaccaca ccacgagtag gaattcgcta   4140
gctcgacaat caacctctgg attacaaaat ttgtgaaaga ttgactggta ttcttaacta   4200
tgttgctcct tttacgctat gtggatacgc tgctttaatg cctttgtatc atgctattgc   4260
ttcccgtatg gctttcattt tctcctcctt gtataaatcc tggttgctgt ctctttatga   4320
ggagttgtgg cccgttgtca ggcaacgtgg cgtggtgtgc actgtgtttg ctgacgcaac   4380
ccccactggt tggggcattg ccaccacctg tcagctcctt tccgggactt tcgctttccc   4440
cctccctatt gccacggcgg aactcatcgc cgcctgcctt gcccgctgct ggacaggggc   4500
tcggctgttg ggcactgaca attccgtggt gttgtcgggg aaatcatcgt cctttccttg   4560
gctgctcgcc tgtgttgcca cctggattct gcgcgggacg tccttctgct acgtcccttc   4620
ggccctcaat ccagcggacc ttccttcccg cggcctgctg ccggctctgc ggcctcttcc   4680
gcgtcttcgc cttcgccctc agacgagtcg gatctccctt tgggccgcct ccccgcctgg   4740
tacctttaag accaatgact tacaaggcag ctgtagatct tagccacttt ttaaaagaaa   4800
aggggggact ggaagggcta attcactccc aacgaagata agatctgctt tttgcttgta   4860
ctgggtctct ctggttagac cagatctgag cctgggagct ctctggctaa ctagggaacc   4920
cactgcttaa gcctcaataa agcttgcctt gagtgcttca agtagtgtgt gcccgtctgt   4980
tgtgtgactc tggtaactag agatccctca gacccttta gtcagtgtgg aaaatctcta   5040
gcagtagtag ttcatgtcat cttattattc agtatttata acttgcaaag aaatgaatat   5100
cagagagtga gaggaacttg tttattgcag cttataatgg ttacaaataa agcaatagca   5160
tcacaaattt cacaaataaa gcattttttt cactgcattc tagttgtggt ttgtccaaac   5220
tcatcaatgt atcttatcat gtctggctct agctatcccg cccctaactc cgcccatccc   5280
gcccctaact ccgcccagtt ccgcccattc tccgccccat ggctgactaa ttttttttat   5340
ttatgcagag gccgaggccg cctcggcctc tgagctattc cagaagtagt gaggaggctt   5400
ttttggaggc ctagactttt gcagatcgac ccatgggggc ccgccccaac tggggtaacc   5460
```

tttgagttct ctcagttggg ggtaatcagc atcatgatgt ggtaccacat catgatgctg 5520
attataagaa tgcggccgcc acactctagt ggatctcgag ttaataattc agaagaactc 5580
gtcaagaagg cgatagaagg cgatgcgctg cgaatcggga gcggcgatac cgtaaagcac 5640
gaggaagcgg tcagcccatt cgccgccaag ctcttcagca atatcacggg tagccaacgc 5700
tatgtcctga tagcggtccg ccacacccag ccggccacag tcgatgaatc cagaaaagcg 5760
gccattttcc accatgatat tcggcaagca ggcatcgcca tgggtcacga cgagatcctc 5820
gccgtcgggc atgctcgcct tgagcctggc gaacagttcg gctggcgcga gcccctgatg 5880
ctcttcgtcc agatcatcct gatcgacaag accggcttcc atccgagtac gtgctcgctc 5940
gatgcgatgt ttcgcttggt ggtcgaatgg gcaggtagcc ggatcaagcg tatgcagccg 6000
ccgcattgca tcagccatga tggatacttt ctcggcagga gcaaggtgag atgacaggag 6060
atcctgcccc ggcacttcgc ccaatagcag ccagtccctt cccgcttcag tgacaacgtc 6120
gagcacagct gcgcaaggaa cgcccgtcgt ggccagccac gatagccgcg ctgcctcgtc 6180
ttgcagttca ttcagggcac cggacaggtc ggtcttgaca aaaagaaccg ggcgcccctg 6240
cgctgacagc cggaacacgg cggcatcaga gcagccgatt gtctgttgtg cccagtcata 6300
gccgaatagc ctctccaccc aagcggccgg agaacctgcg tgcaatccat cttgttcaat 6360
catgcgaaac gatcctcatc ctgtctcttg atcagagctt gatcccctgc gccatcagat 6420
ccttggcggc gagaaagcca tccagtttac tttgcagggc ttcccaacct taccagaggg 6480
cgccccagct ggcaattccg gttcgcttgc tgtccataaa accgcccagt ctagctatcg 6540
ccatgtaagc ccactgcaag ctacctgctt tctctttgcg cttgcgtttt cccttgtcca 6600
gatagcccag tagctgacat tcatccgggg tcagcaccgt ttctgcggac tggctttcta 6660
cgtgctcgag gggggccaaa cggtctccag cttggctgtt ttggcggatg agagaagatt 6720
ttcagcctga tacagattaa atcagaacgc agaagcggtc tgataaaaca gaatttgcct 6780
ggcggcagta gcgcggtggt cccacctgac cccatgccga actcagaagt gaaacgccgt 6840
agcgccgatg gtagtgtggg gtctccccat gcgagagtag ggaactgcca ggcatcaaat 6900
aaaacgaaag gctcagtcga aagactgggc ctttcgtttt atctgttgtt tgtcggtgaa 6960
cgctctcctg agtaggacaa atccgccggg agcggatttg aacgttgcga agcaacggcc 7020
cggagggtgg cgggcaggac gcccgccata aactgccagg catcaaatta agcagaaggc 7080
catcctgacg gatggccttt ttgcgtttct acaaactctt ttgtttattt ttctaaatac 7140
attcaaatat gtatccgctc atgaccaaaa tcccttaacg tgagttttcg ttccactgag 7200
cgtcagaccc cgtagaaaag atcaaaggat cttcttgaga tccttttttt ctgcgcgtaa 7260
tctgctgctt gcaaacaaaa aaaccaccgc taccagcggt ggtttgtttg ccggatcaag 7320
agctaccaac tctttttccg aaggtaactg gcttcagcag agcgcagata ccaaatactg 7380
tccttctagt gtagccgtag ttaggccacc acttcaagaa ctctgtagca ccgcctacat 7440
acctcgctct gctaatcctg ttaccagtgg ctgctgccag tggcgataag tcgtgtctta 7500
ccgggttgga ctcaagacga tagttaccgg ataaggcgca gcggtcgggc tgaacggggg 7560
gttcgtgcac acagcccagc ttggagcgaa cgacctacac cgaactgaga tacctacagc 7620
gtgagctatg agaaagcgcc acgcttcccg aagggagaaa ggcggacagg tatccggtaa 7680
gcggcagggt cggaacagga gagcgcacga gggagcttcc agggggaaac gcctggtatc 7740
tttatagtcc tgtcgggttt cgccacctct gacttgagcg tcgatttttg tgatgctcgt 7800

-continued caggggggcg gagcctatgg aaaaacgcca gcaacgcggc ctttttacgg ttcctggcct 7860
tttgctggcc ttttgctcac atgttctttc ctgcgttatc ccctgattct gtggataacc 7920
gtattaccgc ctttgagtga gctgataccg ctcgccgcag ccgaacgacc gagcgcagcg 7980
agtcagtgag cgaggaagcg gaagagcgcc tgatgcggta ttttctcctt acgcatctgt 8040
gcggtatttc acaccgcata tggtgcactc tcagtacaat ctgctctgat gccgcatagt 8100
taagccagta tacactccgc tatcgctacg tgactgggtc atggctgcgc cccgacaccc 8160
gccaacaccc gctgacgcgc cctgacgggc ttgtctgctc ccggcatccg cttacagaca 8220
agctgtgacc gtctccggga gctgcatgtg tcagaggttt tcaccgtcat caccgaaacg 8280
cgcgaggcag cagatcaatt cgcgcgcgaa ggcgaagcgg catgcataat gtgcctgtca 8340
aatggacgaa gcagggattc tgcaaaccct atgctactcc gtcaagccgt caattgtctg 8400
attcgttacc aattatgaca acttgacggc tacatcattc actttttctt cacaaccggc 8460
acggaactcg ctcgggctgg ccccggtgca tttttaaat acccgcgaga aatagagttg 8520
atcgtcaaaa ccaacattgc gaccgacggt ggcgataggc atccgggtgg tgctcaaaag 8580
cagcttcgcc tggctgatac gttggtcctc gcgccagctt aagacgctaa tccctaactg 8640
ctggcggaaa agatgtgaca gacgcgacgg cgacaagcaa acatgctgtg cgacgctggc 8700
gat 8703

<210> SEQ ID NO 35
<211> LENGTH: 4668
<212> TYPE: DNA
<213> ORGANISM: Artificial Sequence
<220> FEATURE:
<223> OTHER INFORMATION: pMC-CMV-SV40-polyA O1P1-3C(wt) (without bacterial backbone)

<400> SEQUENCE: 35
cccttgggct ccccgggcgc gactagtgaa ttgatactag tattatgccc agtacatgac 60
cttatgggac tttcctactt ggcagtacat ctacgtatta gtcatcgcta ttaccatggt 120
gatgcggttt tggcagtaca tcaatgggcg tggatagcgg tttgactcac ggggatttcc 180
aagtctccac cccattgacg tcaatgggag tttgttttgg caccaaaatc aacgggactt 240
tccaaaatgt cgtaacaact ccgccccatt gacgcaaatg ggcggtaggc gtgtacggtg 300
ggaggtttat ataagcagag ctcgtttagt gaaccgtcag atcgcctgga gacgccatcc 360
acgctgtttt gacctccata gaagattcta gagtcgacgc ggccgcggat ccgccgccgc 420
catgggagcc gggcaatcca gcccggcaac cgggtcacag aaccaatcag gcaacactgg 480
gagcatcatc aacaattact acatgcagca gtaccaaaac tctatggaca cacaacttgg 540
tgacaacgct acaagcggag gctcaaacga ggggtccacg gacacaacct ccacccacac 600
aaccaacact cagaacaacg actggttctc gaagctggcc agttccgctt tcagcggtct 660
tttcggcgct cttctcgccg acaagaaaac cgaggagacc actcttcttg aggaccgcat 720
cctcactact cgtaacggac acaccacctc gacaacccag tcgagcgtag gagtcacata 780
cgggtatgca acggctgagg atttcgtgag cgggccaaac acctctggtc ttgagaccag 840
ggttgcccag gcagagcggt tctttaaaac ccacctgttc gactgggtca caagtgaccc 900
gttcggacgg tgccacctgc tagaacttcc aactgaccac aaaggtgtct atggcagcct 960
gaccgactcg tatgcttata tgaggaacgg ctgggatgtt gaagtcactg ctgtgggaaa 1020
tcagttcaat ggaggatgcc tgttggtggc tatggtgcca gaactttgct ccatacagaa 1080

-continued

```
gagggagctg taccagctca cgctctttcc tcaccagttc atcaaccctc ggacgaacat   1140
gacagcacac atcactgtgc cctttgttgg cgtcaaccgt tatgaccagt acaaggtaca   1200
caaaccttgg accctcgtgg ttatggttgt agcccccctg accgtcaaca gtgaaggtgc   1260
cccgcaaatc aaggtgtatg ccaacatcgc acctaccaac gtacacgtcg cgggtgagtt   1320
cccttccaaa gaggggatct tccctgtggc ttgcagcgat ggttatggcg gtctggtgac   1380
aactgacccg aaaacggctg accccgctta cgggaaagtg tttaaccccc cccgcaacat   1440
gttgccgggg cggttcacca attttcttga cgtggctgag gcgtgcccca cgtttctcca   1500
cttcgagggt gacgtgccat acgtgaccac gaagacggat tcagacaggg tgctcgctca   1560
gttcgacttg tctttggcag caaagcacat gtccaacacc ttccttgcag gtctcgccca   1620
gtactacaca cagtacagcg gcaccatcaa cctgcacttc atgttcacag ggcctactga   1680
cgcgaaggcg cgttacatga ttgcgtatgc tcctcctggc atggaaccac ctaaaacgcc   1740
agaggcggct gcccactgca tccatgctga atgggacaca gggttgaact caaaattcac   1800
attttcaatc ccttaccttt cggcggctga ttacgcttac acagcgtctg acactgctga   1860
gaccacaaat gtacagggat gggtttgcct gtttcaaata acacacggga aagctgacgg   1920
cgacgcactg gtcgttttgg ccagcgccgg aaaggacttt gagctgcgcc tgccggtgga   1980
tgctcgcaca cagactacct cagcgggcga gtcagcagac cccgtgaccg ccaccgttga   2040
gaattacggt ggcgagacac aggtccagag gcgccaacac acggacgtgt catttatatt   2100
agacagattt gtgaaagtga caccaaaaga ccaaattaat gtattggacc tgatgcaaac   2160
ccctgctcac actttggtgg gagcactcct tcgtactgcc acttactatt tcgctgactt   2220
agaggtggca gtgaagcacg agggaaacct cacctgggtg ccgaacgggg cgcctgaagc   2280
ggcgttggac aacaccacca acccaacagc ttaccacaag gcaccactca cccgacttgc   2340
actgccttac acggcgccac accgcgtgtt ggctactgtt tacaacggga acagcaagta   2400
tggtgacggc acggtggcca atgtgagagg tgatctgcaa gtgttggccc agaaggcggc   2460
gagagcgctg cctacctcct tcaactacgg tgccattaaa gctactcggg tgactgaact   2520
gctttaccgc atgaagaggg ctgagacata ctgtccccgg cctcttttgg ccattcaccc   2580
ggaccaggct agacacaagc agaagattgt ggctccggtg aaacagcttc taaattttga   2640
cctgctcaaa ttggcgggag atgtggagtc caaccctggg cccagcggcc gcatgagtgg   2700
tgccccaccg accgacttgc aaaagatggt catgagcaac actaagcctg ttgagctcat   2760
ccttgacggt aagacggtgg ccatctgctg cgccaccgga gtgtttggta ctgcctacct   2820
cgtgcctcgt caccttttcg cagaaaagta cgacaggatc atgttggacg gcagggccat   2880
gacagacagt gactacagag tgtttgagtt tgagattaaa gtaaaaggac aggacatgct   2940
ctcagacgct gcgctcatgg tgctccaccg tggcaaccgt gtgagagaca tcacgaaaca   3000
ctttcgtgat acagcaagaa tgaagaaagg taccccccgtt gtcggcgtga tcaacaacgc   3060
cgacgttggg agactgattt tctccggtga ggccctcacc tacaaggaca ttgtagtgtg   3120
catggatgga gacaccatgc cgggcctatt tgcctacaga gccgctacca aggctggcta   3180
ctgtggagga gccgttcttg ccaaggacgg agctgacaca tttatcgtcg gcactcactc   3240
cgcaggaggc aatggagtcg ggtactgctc atgcgtatct aggtccatgc tcttgaagat   3300
gaaggcacac attgaccccg aaccacacca cgagtaggaa ttcgctagct cgacaatcaa   3360
cctctggatt acaaaatttg tgaaagattg actggtattc ttaactatgt tgctcctttt   3420
acgctatgtg gatacgctgc tttaatgcct ttgtatcatg ctattgcttc ccgtatggct   3480
```

ttcattttct cctccttgta taaatcctgg ttgctgtctc tttatgagga gttgtggccc 3540
gttgtcaggc aacgtggcgt ggtgtgcact gtgtttgctg acgcaacccc cactggttgg 3600
ggcattgcca ccacctgtca gctcctttcc gggactttcg ctttccccct ccctattgcc 3660
acggcggaac tcatcgccgc ctgccttgcc cgctgctgga caggggctcg gctgttgggc 3720
actgacaatt ccgtggtgtt gtcggggaaa tcatcgtcct ttccttggct gctcgcctgt 3780
gttgccacct ggattctgcg cgggacgtcc ttctgctacg tcccttcggc cctcaatcca 3840
gcggaccttc cttcccgcgg cctgctgccg gctctgcggc ctcttccgcg tcttcgcctt 3900
cgccctcaga cgagtcggat ctccctttgg gccgcctccc cgcctggtac ctttaagacc 3960
aatgacttac aaggcagctg tagatcttag ccacttttta aaagaaaagg ggggactgga 4020
agggctaatt cactcccaac gaagataaga tctgcttttt gcttgtactg ggtctctctg 4080
gttagaccag atctgagcct gggagctctc tggctaacta gggaacccac tgcttaagcc 4140
tcaataaagc ttgccttgag tgcttcaagt agtgtgtgcc cgtctgttgt gtgactctgg 4200
taactagaga tccctcagac ccttttagtc agtgtggaaa atctctagca gtagtagttc 4260
atgtcatctt attattcagt atttataact tgcaaagaaa tgaatatcag agagtgagag 4320
gaacttgttt attgcagctt ataatggtta caaataaagc aatagcatca caaatttcac 4380
aaataaagca tttttttcac tgcattctag ttgtggtttg tccaaactca tcaatgtatc 4440
ttatcatgtc tggctctagc tatcccgccc ctaactccgc ccatcccgcc cctaactccg 4500
cccagttccg cccattctcc gccccatggc tgactaattt tttttattta tgcagaggcc 4560
gaggccgcct cggcctctga gctattccag aagtagtgag gaggcttttt tggaggccta 4620
gacttttgca gatcgaccca tgggggcccg ccccaactgg ggtaacct 4668

<210> SEQ ID NO 36
<211> LENGTH: 28
<212> TYPE: DNA
<213> ORGANISM: Artificial Sequence
<220> FEATURE:
<223> OTHER INFORMATION: Synthetic primer - AscI-Kzk-Gluc-F

<400> SEQUENCE: 36
ttggcgcgcc gccaccatgg gagtcaaa 28

<210> SEQ ID NO 37
<211> LENGTH: 26
<212> TYPE: DNA
<213> ORGANISM: Artificial Sequence
<220> FEATURE:
<223> OTHER INFORMATION: Synthetic primer - Gluc-R-NotI

<400> SEQUENCE: 37
gcggccgctt agtcaccacc ggcccc 26

<210> SEQ ID NO 38
<211> LENGTH: 6430
<212> TYPE: DNA
<213> ORGANISM: Artificial Sequence
<220> FEATURE:
<223> OTHER INFORMATION: pMC-CMV-SV40-polyA SGLuc (with bacterial backbone)

<400> SEQUENCE: 38
acattaccct gttatcccta gatacattac cctgttatcc cagatgacat accctgttat 60
ccctagatga cattaccctg ttatcccaga tgacattacc ctgttatccc tagatacatt 120

-continued

```
accctgttat cccagatgac ataccctgtt atccctagat gacattaccc tgttatccca    180
gatgacatta ccctgttatc cctagataca ttaccctgtt atcccagatg acataccctg    240
ttatccctag atgacattac cctgttatcc cagatgacat taccctgtta tccctagata    300
cattaccctg ttatcccaga tgacataccc tgttatccct agatgacatt accctgttat    360
cccagatgac attaccctgt tatccctaga tacattaccc tgttatccca gatgacatac    420
cctgttatcc ctagatgaca ttaccctgtt atcccagatg acattaccct gttatcccta    480
gatacattac cctgttatcc cagatgacat accctgttat ccctagatga cattaccctg    540
ttatcccaga tgacattacc ctgttatccc tagatacatt accctgttat cccagatgac    600
ataccctgtt atccctagat gacattaccc tgttatccca gatgacatta ccctgttatc    660
cctagataca ttaccctgtt atcccagatg acataccctg ttatccctag atgacattac    720
cctgttatcc cagataaact caatgatgat gatgatgatg gtcgagactc agcggccgcg    780
gtgccagggc gtgcccttgg gctccccggg cgcgactagt gaattgatac tagtattatg    840
cccagtacat gaccttatgg gactttccta cttggcagta catctacgta ttagtcatcg    900
ctattaccat ggtgatgcgg ttttggcagt acatcaatgg gcgtggatag cggtttgact    960
cacggggatt tccaagtctc caccccattg acgtcaatgg gagtttgttt tggcaccaaa   1020
atcaacggga ctttccaaaa tgtcgtaaca actccgcccc attgacgcaa atgggcggta   1080
ggcgtgtacg gtgggaggtt tatataagca gagctcgttt agtgaaccgt cagatcgcct   1140
ggagacgcca tccacgctgt tttgacctcc atagaagatt ctagagtcga cgcggccgcg   1200
gatccttgct agcctcgaga cgcgtgattt tggcgcgccg ccaccatggg agtcaaagtt   1260
ctgtttgccc tgatctgcat cgctgtggcc gaggccaagc ccaccgagaa caacgaagac   1320
ttcaacatcg tggccgtggc cagcaacttc gcgaccacgg atctcgatgc tgaccgcggg   1380
aagttgcccg gcaagaagct gccgctggag gtgctcaaag agatggaagc caatgcccgg   1440
aaagctggct gcaccagggg ctgtctgatc tgcctgtccc acatcaagtg cacgcccaag   1500
atgaagaagt ggctcccagg acgctgccac acctacgaag gcgacaaaga gtccgcacag   1560
ggcggcatag gcgaggcgat cgtcgacatt cctgagattc ctgggttcaa ggacttggag   1620
cccatggagc agttcatcgc acaggtcgat ctgtgtgtgg actgcacaac tggctgcctc   1680
aaagggcttg ccaacgtgca gtgttctgac ctgctcaaga agtggctgcc gcaacgctgt   1740
gcgacctttg ccagcaagat ccagggccag gtggacaaga tcaagggggc cggtggtgac   1800
taagcggacg caaaatcagc ctcaatcttt cccgggggta ccgtcgactg cggccgcgaa   1860
ttcgctagct cgacaatcaa cctctggatt acaaaatttg tgaaagattg actggtattc   1920
ttaactatgt tgctcctttt acgctatgtg gatacgctgc tttaatgcct ttgtatcatg   1980
ctattgcttc ccgtatggct ttcattttct cctccttgta taaatcctgg ttgctgtctc   2040
tttatgagga gttgtggccc gttgtcaggc aacgtggcgt ggtgtgcact gtgtttgctg   2100
acgcaacccc cactggttgg ggcattgcca ccacctgtca gctcctttcc gggactttcg   2160
ctttccccct ccctattgcc acggcggaac tcatcgccgc ctgccttgcc cgctgctgga   2220
caggggctcg gctgttgggc actgacaatt ccgtggtgtt gtcggggaaa tcatcgtcct   2280
ttccttggct gctcgcctgt gttgccacct ggattctgcg cgggacgtcc ttctgctacg   2340
tcccttcggc cctcaatcca gcggaccttc cttcccgcgg cctgctgccg gctctgcggc   2400
ctcttccgcg tcttcgcctt cgccctcaga cgagtcggat ctccctttgg gccgcctccc   2460
```

-continued

```
cgcctggtac ctttaagacc aatgacttac aaggcagctg tagatcttag ccacttttta   2520
aaagaaaagg ggggactgga agggctaatt cactcccaac gaagataaga tctgcttttt   2580
gcttgtactg ggtctctctg gttagaccag atctgagcct gggagctctc tggctaacta   2640
gggaacccac tgcttaagcc tcaataaagc ttgccttgag tgcttcaagt agtgtgtgcc   2700
cgtctgttgt gtgactctgg taactagaga tccctcagac ccttttagtc agtgtggaaa   2760
atctctagca gtagtagttc atgtcatctt attattcagt atttataact tgcaaagaaa   2820
tgaatatcag agagtgagag gaacttgttt attgcagctt ataatggtta caaataaagc   2880
aatagcatca caaatttcac aaataaagca tttttttcac tgcattctag ttgtggtttg   2940
tccaaactca tcaatgtatc ttatcatgtc tggctctagc tatcccgccc ctaactccgc   3000
ccatcccgcc cctaactccg cccagttccg cccattctcc gccccatggc tgactaattt   3060
tttttattta tgcagaggcc gaggccgcct cggcctctga gctattccag aagtagtgag   3120
gaggcttttt tggaggccta gacttttgca gatcgaccca tgggggcccg ccccaactgg   3180
ggtaaccttt gagttctctc agttgggggt aatcagcatc atgatgtggt accacatcat   3240
gatgctgatt ataagaatgc ggccgccaca ctctagtgga tctcgagtta ataattcaga   3300
agaactcgtc aagaaggcga tagaaggcga tgcgctgcga atcgggagcg gcgataccgt   3360
aaagcacgag gaagcggtca gcccattcgc cgccaagctc ttcagcaata tcacgggtag   3420
ccaacgctat gtcctgatag cggtccgcca cacccagccg gccacagtcg atgaatccag   3480
aaaagcggcc attttccacc atgatattcg gcaagcaggc atcgccatgg gtcacgacga   3540
gatcctcgcc gtcgggcatg ctcgccttga gcctggcgaa cagttcggct ggcgcgagcc   3600
cctgatgctc ttcgtccaga tcatcctgat cgacaagacc ggcttccatc cgagtacgtg   3660
ctcgctcgat gcgatgtttc gcttggtggt cgaatgggca ggtagccgga tcaagcgtat   3720
gcagccgccg cattgcatca gccatgatgg atactttctc ggcaggagca aggtgagatg   3780
acaggagatc ctgccccggc acttcgccca atagcagcca gtcccttccc gcttcagtga   3840
caacgtcgag cacagctgcg caaggaacgc ccgtcgtggc cagccacgat agccgcgctg   3900
cctcgtcttg cagttcattc agggcaccgg acaggtcggt cttgacaaaa agaaccgggc   3960
gcccctgcgc tgacagccgg aacacggcgg catcagagca gccgattgtc tgttgtgccc   4020
agtcatagcc gaatagcctc tccacccaag cggccggaga acctgcgtgc aatccatctt   4080
gttcaatcat gcgaaacgat cctcatcctg tctcttgatc agagcttgat cccctgcgcc   4140
atcagatcct tggcggcgag aaagccatcc agtttacttt gcagggcttc ccaaccttac   4200
cagagggcgc cccagctggc aattccggtt cgcttgctgt ccataaaacc gcccagtcta   4260
gctatcgcca tgtaagccca ctgcaagcta cctgctttct ctttgcgctt gcgttttccc   4320
ttgtccagat agcccagtag ctgacattca tccggggtca gcaccgtttc tgcggactgg   4380
ctttctacgt gctcgagggg ggccaaacgg tctccagctt ggctgttttg gcggatgaga   4440
gaagattttc agcctgatac agattaaatc agaacgcaga agcggtctga taaaacagaa   4500
tttgcctggc ggcagtagcg cggtggtccc acctgacccc atgccgaact cagaagtgaa   4560
acgccgtagc gccgatggta gtgtggggtc tccccatgcg agagtaggga actgccaggc   4620
atcaaataaa acgaaaggct cagtcgaaag actgggcctt tcgttttatc tgttgtttgt   4680
cggtgaacgc tctcctgagt aggacaaatc cgccgggagc ggatttgaac gttgcgaagc   4740
aacggcccgg agggtggcgg gcaggacgcc cgccataaac tgccaggcat caaattaagc   4800
agaaggccat cctgacggat ggcctttttg cgtttctaca aactcttttg tttatttttc   4860
```

```
taaatacatt caaatatgta tccgctcatg accaaaatcc cttaacgtga gttttcgttc   4920

cactgagcgt cagaccccgt agaaaagatc aaaggatctt cttgagatcc tttttttctg   4980

cgcgtaatct gctgcttgca aacaaaaaaa ccaccgctac cagcggtggt ttgtttgccg   5040

gatcaagagc taccaactct ttttccgaag gtaactggct tcagcagagc gcagatacca   5100

aatactgtcc ttctagtgta gccgtagtta ggccaccact tcaagaactc tgtagcaccg   5160

cctacatacc tcgctctgct aatcctgtta ccagtggctg ctgccagtgg cgataagtcg   5220

tgtcttaccg ggttggactc aagacgatag ttaccggata aggcgcagcg gtcgggctga   5280

acggggggtt cgtgcacaca gcccagcttg gagcgaacga cctacaccga actgagatac   5340

ctacagcgtg agctatgaga aagcgccacg cttcccgaag ggagaaaggc ggacaggtat   5400

ccggtaagcg gcagggtcgg aacaggagag cgcacgaggg agcttccagg gggaaacgcc   5460

tggtatcttt atagtcctgt cgggtttcgc cacctctgac ttgagcgtcg atttttgtga   5520

tgctcgtcag gggggcggag cctatggaaa aacgccagca acgcggcctt tttacggttc   5580

ctggcctttt gctggccttt tgctcacatg ttctttcctg cgttatcccc tgattctgtg   5640

gataaccgta ttaccgcctt tgagtgagct gataccgctc gccgcagccg aacgaccgag   5700

cgcagcgagt cagtgagcga ggaagcggaa gagcgcctga tgcggtattt tctccttacg   5760

catctgtgcg gtatttcaca ccgcatatgg tgcactctca gtacaatctg ctctgatgcc   5820

gcatagttaa gccagtatac actccgctat cgctacgtga ctgggtcatg gctgcgcccc   5880

gacacccgcc aacacccgct gacgcgccct gacgggcttg tctgctcccg gcatccgctt   5940

acagacaagc tgtgaccgtc tccgggagct gcatgtgtca gaggttttca ccgtcatcac   6000

cgaaacgcgc gaggcagcag atcaattcgc gcgcgaaggc gaagcggcat gcataatgtg   6060

cctgtcaaat ggacgaagca gggattctgc aaaccctatg ctactccgtc aagccgtcaa   6120

ttgtctgatt cgttaccaat tatgacaact tgacggctac atcattcact ttttcttcac   6180

aaccggcacg gaactcgctc gggctggccc cggtgcattt tttaaatacc cgcgagaaat   6240

agagttgatc gtcaaaacca acattgcgac cgacggtggc gataggcatc cgggtggtgc   6300

tcaaaagcag cttcgcctgg ctgatacgtt ggtcctcgcg ccagcttaag acgctaatcc   6360

ctaactgctg gcggaaaaga tgtgacagac gcgacggcga caagcaaaca tgctgtgcga   6420

cgctggcgat                                                          6430
```

<210> SEQ ID NO 39
<211> LENGTH: 2395
<212> TYPE: DNA
<213> ORGANISM: Artificial Sequence
<220> FEATURE:
<223> OTHER INFORMATION: pMC-CMV-SV40-polyA SGLuc (without bacterial backbone)

<400> SEQUENCE: 39

```
cccttgggct ccccgggcgc gactagtgaa ttgatactag tattatgccc agtacatgac     60

cttatgggac tttcctactt ggcagtacat ctacgtatta gtcatcgcta ttaccatggt    120

gatgcggttt tggcagtaca tcaatgggcg tggatagcgg tttgactcac ggggatttcc    180

aagtctccac cccattgacg tcaatgggag tttgttttgg caccaaaatc aacgggactt    240

tccaaaatgt cgtaacaact ccgccccatt gacgcaaatg ggcggtaggc gtgtacggtg    300

ggaggtttat ataagcagag ctcgtttagt gaaccgtcag atcgcctgga gacgccatcc    360

acgctgtttt gacctccata gaagattcta gagtcgacgc ggccgcggat ccttgctagc    420
```

-continued

```
ctcgagacgc gtgattttgg cgcgccgcca ccatgggagt caaagttctg tttgccctga    480
tctgcatcgc tgtggccgag gccaagccca ccgagaacaa cgaagacttc aacatcgtgg    540
ccgtggccag caacttcgcg accacggatc tcgatgctga ccgcgggaag ttgcccggca    600
agaagctgcc gctggaggtg ctcaaagaga tggaagccaa tgcccggaaa gctggctgca    660
ccaggggctg tctgatctgc ctgtcccaca tcaagtgcac gcccaagatg aagaagtggc    720
tcccaggacg ctgccacacc tacgaaggcg acaaagagtc cgcacagggc ggcataggcg    780
aggcgatcgt cgacattcct gagattcctg ggttcaagga cttggagccc atggagcagt    840
tcatcgcaca ggtcgatctg tgtgtggact gcacaactgg ctgcctcaaa gggcttgcca    900
acgtgcagtg ttctgacctg ctcaagaagt ggctgccgca acgctgtgcg acctttgcca    960
gcaagatcca gggccaggtg gacaagatca agggggccgg tggtgactaa gcggacgcaa   1020
aatcagcctc aatctttccc gggggtaccg tcgactgcgg ccgcgaattc gctagctcga   1080
caatcaacct ctggattaca aaatttgtga aagattgact ggtattctta actatgttgc   1140
tccttttacg ctatgtggat acgctgcttt aatgcctttg tatcatgcta ttgcttcccg   1200
tatggctttc attttctcct ccttgtataa atcctggttg ctgtctcttt atgaggagtt   1260
gtggcccgtt gtcaggcaac gtggcgtggt gtgcactgtg tttgctgacg caacccccac   1320
tggttggggc attgccacca cctgtcagct cctttccggg actttcgctt tccccctccc   1380
tattgccacg gcggaactca tcgccgcctg ccttgcccgc tgctggacag gggctcggct   1440
gttgggcact gacaattccg tggtgttgtc ggggaaatca tcgtcctttc cttggctgct   1500
cgcctgtgtt gccacctgga ttctgcgcgg gacgtccttc tgctacgtcc cttcggccct   1560
caatccagcg gaccttcctt cccgcggcct gctgccggct ctgcggcctc ttccgcgtct   1620
tcgccttcgc cctcagacga gtcggatctc cctttgggcc gcctccccgc ctggtacctt   1680
taagaccaat gacttacaag gcagctgtag atcttagcca ctttttaaaa gaaaaggggg   1740
gactggaagg gctaattcac tcccaacgaa gataagatct gctttttgct tgtactgggt   1800
ctctctggtt agaccagatc tgagcctggg agctctctgg ctaactaggg aacccactgc   1860
ttaagcctca ataaagcttg ccttgagtgc ttcaagtagt gtgtgcccgt ctgttgtgtg   1920
actctggtaa ctagagatcc ctcagaccct tttagtcagt gtggaaaatc tctagcagta   1980
gtagttcatg tcatcttatt attcagtatt tataacttgc aaagaaatga atatcagaga   2040
gtgagaggaa cttgtttatt gcagcttata atggttacaa ataaagcaat agcatcacaa   2100
atttcacaaa taaagcattt ttttcactgc attctagttg tggtttgtcc aaactcatca   2160
atgtatctta tcatgtctgg ctctagctat cccgccccta actccgccca tcccgcccct   2220
aactccgccc agttccgccc attctccgcc ccatggctga ctaatttttt ttatttatgc   2280
agaggccgag gccgcctcgg cctctgagct attccagaag tagtgaggag gcttttttgg   2340
aggcctagac ttttgcagat cgacccatgg gggcccgccc caactggggt aacct        2395
```